United States Patent [19]
Curtis et al.

[11] Patent Number: 6,071,928
[45] Date of Patent: Jun. 6, 2000

[54] SPIRO-PIPERIDINE DERIVATIVES AND THEIR USE AS THERAPEUTIC AGENTS

[75] Inventors: Neil Roy Curtis, Puckeridge; Ian Thomas Huscroft, Bishops Stortford; Janusz Jozef Kulagowski, Sawbridgeworth; Christopher John Swain, Duxford, all of United Kingdom

[73] Assignee: Merck Sharp & Dohme, Ltd., Hoddesdon, United Kingdom

[21] Appl. No.: 09/202,551

[22] PCT Filed: Jun. 24, 1997

[86] PCT No.: PCT/GB97/01710

§ 371 Date: Dec. 16, 1998

§ 102(e) Date: Dec. 16, 1998

[87] PCT Pub. No.: WO98/01450

PCT Pub. Date: Jan. 15, 1998

[30] Foreign Application Priority Data

Jul. 3, 1996 [GB] United Kingdom .................. 9613969

[51] Int. Cl.[7] ........................ A61K 31/44; C07D 221/00; C07D 251/00; C07D 239/00; C07D 403/00
[52] U.S. Cl. ........................ 514/278; 546/16; 544/224; 544/242; 544/359; 544/366; 544/367; 544/369
[58] Field of Search ............... 546/16; 514/278; 544/224, 242, 359, 366, 367, 369, 370, 371

[56] References Cited

FOREIGN PATENT DOCUMENTS

WO 94/20500  9/1994  WIPO .
WO 97/19084  5/1997  WIPO .

Primary Examiner—John Kight
Assistant Examiner—Binta Robinson
Attorney, Agent, or Firm—J. Eric Thies; David L. Rose

[57] ABSTRACT

The present invention relates to compounds of formula (I), wherein R is $C_{1-6}$alkyl, $C_{2-6}$alkenyl, $C_{2-6}$alkynyl, $C_{3-7}$cycloalkyl, $C_{3-7}$cycloalkyl$C_{1-4}$alkyl, which groups are optionally substituted by hydroxy, $C_{1-4}$alkoxy or $NR^aR^b$, where $R^a$ and $R^b$ each independently repesent hydrogen or $C_{1-4}$alkyl; or R is $C_{1-4}$alkyl substituted by Ar, and optionally further substituted by one or both of $R^4$ and $R^5$; $R^1$, $R^2$ and $R^3$ represent a variety of substituents; $R^9$ and $R^{10}$ are each hydrogen, halogen, $C_{1-6}$alkyl, $CH_2OR^c$, oxo, $CO_2R^a$ or $CONR^aR^b$ where $R^c$ represents hydrogen, $C_{1-6}$alkyl or phenyl; X is —$CH_2$, or —$CH_2CH_2$—; Y is —CH—, —$CH_2$—, —$CH_2CH$— or —$CH_2CH_2$—, with the proviso that the sum total of carbon atoms in X+Y is 2 or 3; and when Y is —CH— or —$CH_2CH$—, the broken line is a double bond; or a pharmaceutically acceptable salt thereof. The compounds are of particular use in the treatment or prevention of pain, inflammation, migraine, anesis and postherpetic neuralgia.

(I)

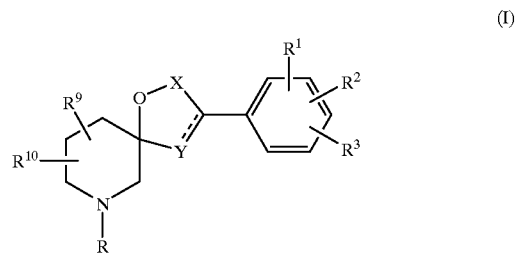

21 Claims, No Drawings

SPIRO-PIPERIDINE DERIVATIVES AND THEIR USE AS THERAPEUTIC AGENTS

This application is a 371 of PCT/GB97/01710, filed Jun. 24, 1997, which claims priority from Great Britain Application No. 9613969.6, filed Jul. 3, 1996.

This invention relates to a class of azacyclic compounds which are useful as tachykinin antagonists. More particularly, the compounds of the invention are spiro-substituted azacyclic derivatives.

International (PCT) patent specification no. WO 94/20500 (published Sep. 15, 1994) discloses spiroazacyclic derivatives as substance P antagonists. In particular, WO 94/20500 relates to spirocyclic piperidine derivatives containing a 1,8-diazaspiro[5.5]undecane core.

We have now found a further class of non-peptides which are potent antagonists of tachykinins, especially of substance P.

The present invention provides compounds of the formula (I):

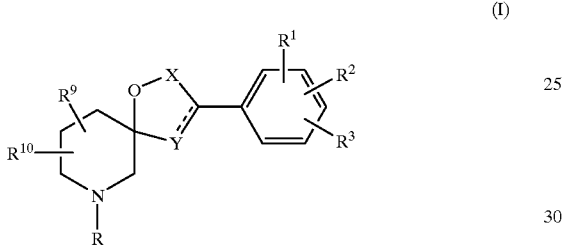

(I)

wherein

R represents $C_{1-6}$alkyl, $C_{2-6}$alkenyl, $C_{2-6}$alkynyl, $C_{3-7}$cycloalkyl, $C_{3-7}$cycloalkyl$C_{1-4}$alkyl, which groups are optionally substituted by a group selected from hydroxy, $C_{1-4}$alkoxy or $NR^aR^b$, where $R^a$ and $R^b$ each independently represent hydrogen or $C^{1-4}$alkyl;

or R represents a $C^{1-4}$alkyl group substituted by the group Ar, and optionally further substituted by one or both of the groups $R^4$ and $R^5$;

$R^1$ represents hydrogen, hydroxy, $C_{1-6}$alkyl, $C_{2-6}$alkenyl, $C_{2-6}$alkynyl, $C_{3-7}$cycloalkyl, $C_{3-7}$cycloalkyl$C_{1-4}$alkyl, $C_{1-6}$alkoxy, fluoro$C_{1-6}$alkyl, fluoro$C_{1-6}$alkoxy, hydroxy$C_{1-4}$alkyl, $C_{1-6}$alkoxy$C_{1-4}$alkyl, $C_{1-6}$alkoxy$C_{1-4}$alkoxy, fluoro$C_{1-6}$alkoxy$C_{1-4}$alkyl, $C_{2-6}$alkenyloxy, $C_{3-7}$cycloalkoxy, $C_{3-7}$cycloalkyl$C_{1-4}$alkoxy, phenoxy, benzyloxy, cyano, halogen, trimethylsilyl, nitro, $NR^aR^h$, $SR^a$, $SOR^a$, $SO_2R^a$, $OSO_2R^a$. $COR^a$, $CO_2R^a$, $CONR^aR^b$, $SO_2NR^aR^b$, or $OC_{1-4}$alkyl$NR^aR^b$. where $R^a$ and $R^b$ each independently represent hydrogen, $C_{1-4}$alkyl or fluoro$C_{1-4}$alkyl;

$R^2$ represents hydrogen, halogen, $C_{1-6}$alkyl or $C_{1-6}$alkoxy;

or when $R^2$ is adjacent to $R^1$, they may be joined together such that there is formed a 5- or 6-membered saturated or unsaturated ring containing one or two atoms selected from nitrogen, oxygen and sulphur, which ring is optionally substituted by a group selected from $C_{1-4}$alkyl, $CF_3$, =O or =S;

$R^3$ represents hydrogen, halogen, $C_{1-6}$alkyl, $C_{2-6}$alkenyl, $C_{2-6}$alkynyl, fluoro$C_{1-6}$alkyl, $C_{1-6}$alkoxy, fluoro$C_{1-6}$alkoxy, $C_{3-7}$cycloalkyl, $C_{3-7}$cycloalkyl$C_{1-4}$alkyl, hydroxy, phenoxy, benzyloxy, trimethylsilyl, nitro, cyano, $SR^a$, $SOR^a$, $SO_2R^a$, $NR^aR^b$, $COR^a$, $CO_2R^a$, $CONR^aR^b$, $SO_2NR^aR^b$, $OC_{1-4}$alkyl$NR^aR^b$, $NR^aCOR^d$, or $C_{1-4}$alkyl substituted by a $C^{1-4}$alkoxy, hydroxy, cyano or $CO_2R^a$ group, where $R^a$ and $R^b$ are as previously defined and $R^d$ is $C_{1-6}$alkyl, $C_{1-6}$alkoxy, fluoro$C_{1-6}$alkyl or phenyl;

or $R^3$ represents a 5- or 6-membered aromatic heterocyclic group containing 1, 2, 3 or 4 heteroatoms, selected from nitrogen, oxygen and sulphur, which group is optionally substituted by one or two groups selected from $C_{1-6}$alkyl, $C_{1-6}$alkoxy, $C_{3-7}$cycloalkyl, $C_{3-7}$cycloalkyl$C_{1-4}$alkyl, trifluoromethyl, $OCF_3$, $NO_2$, CN, $SR^a$, $SOR^a$, $SO_2R^a$, $COR^a$, $CO_2R^a$, phenyl, —$(CH_2)_rNR^aR^b$, —$(CH_2)_rNR^aCOR^b$, —$(CH_2)_rCONR^aR^b$, or $CH_2C(O)R^a$, where $R^a$ and $R^b$ are each independently hydrogen or $C_{1-4}$alkyl and r is zero, 1 or 2;

$R^4$ and $R^5$ each independently represent hydroxy, $C_{1-4}$alkyl, $C_{1-4}$alkoxy$C_{1-4}$alkyl, hydroxy$C_{1-4}$alkyl or $C_{1-4}$alkyl$NR^aR^b$ where $R^a$ and $R^b$ are each independently hydrogen or $C_{1-4}$alkyl, or together $R^4$ and $R^5$ represent an oxo group or when $R^4$ and $R^5$ are attached to the same carbon atom, they may be joined together to form a $C_{3-5}$cycloalkyl ring;

Ar represents phenyl optionally substituted by one or two substituents selected from halogen, $C_{1-6}$alkyl, $C_{1-6}$alkoxy, $CF_3$, $OCF_3$, $NO_2$, CN, $SR^a$, $SOR^a$, $SO_2R^a$, $COR^a$, $CO_2R^a$, $(CH_2)_rCONR^aR^b$, $(CH_2)_rNR^aR^b$ or $(CH_2)_rNR^aCOR^b$, where $R^a$ and $R^b$ are independently hydrogen or $C_{1-4}$alkyl and r is zero, 1 or 2;

or Ar represents a 5-membered or 6-membered heterocyclic ring containing 1, 2 or 3 nitrogen atoms optionally substituted by =O or =S and optionally substituted by a group of the formula $ZNR^7R^8$ where Z is $C_{1-6}$alkylene or $C_{3-6}$cycloalkyl;

$R^7$ is hydrogen or $C_{1-4}$alkyl, $C_{3-7}$cycloalkyl, $C_{3-7}$cycloalkyl$C_{1-4}$alkyl, or $C_{2-4}$alkyl substituted by $C_{1-4}$alkoxy or hydroxyl;

$R^8$ is hydrogen or $C_{1-4}$alkyl, $C_{3-7}$cycloalkyl, $C_{3-7}$cycloalkyl$C_{1-4}$alkyl, or $C_{2-4}$alkyl substituted by $C_{1-4}$alkoxy, hydroxyl or a 4, 5 or 6 membered heteroaliphatic ring containing one or two heteroatoms selected from N, O and S;

or $R^7$, $R^8$ and the nitrogen atom to which they are attached form a heteroaliphatic ring of 4 to 7 ring atoms, optionally substituted by one or two groups selected from hydroxy or $C_{1-4}$alkoxy optionally substituted by a $C_{1-4}$alkoxy or hydroxyl group, and optionally containing a double bond, which ring may optionally contain an oxygen or sulphur ring atom, a group S(O) or $S(O)_2$ or a second nitrogen atom which will be part of a NH or $NR^c$ moiety where $R^c$ is $C_{1-4}$alkyl optionally substituted by hydroxy or $C_{1-4}$alkoxy;

or $R^7$, $R^8$ and the nitrogen atom to which they are attached form a non-aromatic azabicyclic ring system of 6 to 12 ring atoms;

or Z, $R^7$ and the nitrogen atom to which they are attached form a heteroaliphatic ring to 4 to 7 ring atoms which may optionally contain an oxygen ring atom;

$R^9$ and $R^{10}$ each independently represent hydrogen, halogen, $C_{1-6}$alkyl, $CH_2OR^e$, oxo, $CO_2R^a$ or $CONR^aR^b$ where $R^a$ and $R^b$ are as previously defined and $R^e$ represents hydrogen, $C_{1-6}$alkyl or phenyl;

X represents —$CH_2$, or —$CH_2CH_2$—;

Y represents —CH=, —$CH_2$—, —$CH_2CH$= or —$CH_2CH_2$—, with the proviso that the sum total of carbon atoms in X+Y is 2 or 3; and when Y is —CH═ or —CH₂CH═, the broken line represents a double bond;

and pharmaceutically acceptable salts thereof.

A preferred sub-class of compounds of formula (I) is that wherein:

R$^1$ represents halogen, C$_{1-6}$alkyl, C$_{2-6}$alkenyl, C$_{2-6}$alkynyl, C$_{3-7}$cycloalkyl, C$_{3-7}$cycloalkylC$_{1-4}$alkyl, C$_{1-6}$alkoxy, fluoroC$_{1-6}$alkyl, fluoroC$_{1-6}$alkoxy, C$_{1-4}$alkyl substituted by a C$_{1-4}$alkoxy or hydroxy group, hydroxy, trimethylsilyl, nitro, CN, SR$^a$, SOR$^a$, SO$_2$R$^a$, COR$^a$, CO$_2$R$^a$, CONR$^a$R$^b$, NR$^a$R$^b$, SO$_2$NR$^a$R$^b$, or OC$_{1-4}$alkylNR$^a$R$^b$, where R$^a$ and R$^b$ are each independently hydrogen or C$_{1-4}$alkyl;

R$^2$ represents hydrogen, halogen, C$_{1-6}$alkyl or C$_{1-6}$alkoxy;

or when R$^2$ is adjacent to R$^1$, they may be joined together such that there is formed a 5- or 6-membered saturated or unsaturated ring containing one or two oxygen atoms;

R$^3$ represents hydrogen, halogen, C$_{1-6}$alkyl, C$_{2-6}$alkenyl, C$_{2-6}$alkynyl, C$_{3-7}$cycloalkyl, C$_{3-7}$cycloalkylC$_{1-4}$alkyl, C$_{1-6}$alkoxy, fluoroC$_{1-6}$alkyl, fluoroC$_{1-6}$alkoxy, C$_{1-4}$alkyl substituted by a C$_{1-4}$alkoxy or hydroxy group, hydroxy, phenoxy, trimethylsilyl, nitro, CN, SR$^a$, SOR$^a$, SO$_2$R$^a$, COR$^a$, CO$_2$R$^a$, CONR$^a$R$^b$, NR$^a$R$^b$, SO$_2$NR$^a$R$^b$, OC$_{1-4}$alkylNR$^a$R$^b$, or a 5- or 6-membered aromatic heterocyclic group containing 1, 2, 3 or 4 heteroatoms, selected from nitrogen, oxygen and sulphur, which group is optionally substituted by one or two groups selected from C$_{1-6}$alkyl, C$_{1-6}$alkoxy, C$_{3-7}$cycloalkyl, C$_{3-7}$cycloalkylC$_{1-4}$alkyl, trifluoromethyl, OCF$_3$, NO$_2$, CN, SR$^a$, SOR$^a$, SO$_2$R$^a$, COR$^a$, CO$_2$R$^a$, phenyl, —(CH$_2$)$_r$NR$^a$R$^b$, —(CH$_2$)$_r$NR$^a$COR$^b$, —(CH$_2$)$_r$CONR$^a$R$^b$, or CH$_2$C(O)R$^a$, where R$^a$ and R$^b$ are each independently hydrogen or C$_{1-4}$alkyl and r is zero, 1 or 2; and R$^4$ and R$^5$ each independently represent C$_{1-4}$alkyl, C$_{1-4}$alkoxyC$_{1-4}$alkyl, hydroxyC$_{1-4}$alkyl or C$_{1-4}$alkylNR$^a$R$^b$ where R$^a$ and R$^b$ are each independently hydrogen or C$_{1-4}$alkyl, or together R$^4$ and R$^5$ represent an oxo group or when R$^4$ and R$^5$ are attached to the same carbon atom, they may be joined together to form a C$_{3-5}$cycloalkyl ring.

A preferred class of compound of formula (I) is that wherein R$^1$ is hydrogen, C$_{1-6}$alkyl, C$_{1-6}$alkoxy, fluoroC$_{1-6}$alkoxy, C$_{3-7}$cycloalkoxy, halogen or NR$^a$R$^b$; in particular a hydrogen atom or a methyl, trifluoromethyl, methoxy, ethoxy, isopropoxy, trifluoromethoxy, 2,2,2-trifluoroethoxy, cyclopropoxy or cyclobutoxy group; and especially a hydrogen atom or a methoxy or cyclopropoxy group.

A particularly preferred class of compound of formula (I) is that wherein R$^1$ is a methyl, trifluoromethyl, methoxy, ethoxy, isopropoxy or trifluoromethoxy group, especially a methoxy group. R$^1$ is preferably in the 2'- (ortho) position on the phenyl ring drawn in formula (I).

Another preferred class of compound of formula (I) is that wherein R$^2$ is a hydrogen, fluorine or chlorine atom, especially a hydrogen atom.

Also preferred is the class of compound of formula (I) in which R$^3$ is halogen, C$_{1-6}$alkyl, fluoroC$_{1-6}$alkyl, C$_{1-6}$alkoxy, fluoroC$_{1-6}$alkoxy, cyano or a 5-membered aromatic heterocyclic group as previously defined.

Particularly preferred is the class of compound of formula (I) in which R$^3$ is halogen or fluoroC$_{1-6}$alkoxy, especially fluorine, trifluoromethoxy or 2.2.2-trifluoroethoxy, or a 5-membered aromatic heterocyclic group as previously defined.

A further preferred class of compound of formula (I) is that wherein R$^3$ is the group

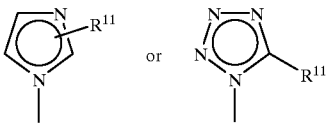

where R$^{11}$ is hydrogen, halogen, C$_{1-6}$alkyl, C$_{1-6}$alkoxy, CF$_3$, OCF$_3$, NO$_2$, CN, SR$^a$, SOR$^a$, SO$_2$R$^a$, COR$^a$, CO$_2$R$^a$, (CH$_2$)$_r$CONR$^a$R$^b$, (CH$_2$)$_r$NR$^a$R$^b$ or (CH$_2$)$_r$NR$^a$COR$^b$, where R$^a$ and R$^b$ are hydrogen or C$_{1-4}$alkyl, and r is zero, 1 or 2.

R$^{11}$ is preferably hydrogen, halogen, C$_{1-4}$alkyl, especially methyl, or CF$_3$. A particularly preferred group represented by R$^{11}$ is CF$_3$.

The group R$^3$ is preferably in the 5'-position on the phenyl ring drawn in formula (I) (i.e. R$^3$ is para to the group R$^1$).

Another preferred class of compound of formula (I) is that wherein R represents a C$_{1-4}$alkyl group (especially a C$_{1-2}$alkyl group) substituted by the group Ar, and optionally substituted by one or both of the groups R$^4$ and R$^5$.

Preferably, R$^4$ is C$_{1-4}$alkyl, especially methyl, or R$^4$ and R$^5$ together represent an oxo group.

Ar preferably represents a phenyl ring, optionally substituted by one or two halogen atoms, especially chlorine or fluorine, or C$_{1-4}$alkoxy, especially methoxy.

Another preferred class of compounds are those wherein Ar represents a pyridyl group.

R$^9$ and R$^{10}$ are preferably attached at the 8- and 9-positions. Preferably one of R$^9$ and R$^{10}$ is hydrogen and, more preferably, R$^9$ and R$^{10}$ are both hydrogen atoms.

Preferably X is —CH$_2$—.

Preferably Y is —CH$_2$— or —CH═, especially —CH$_2$—.

One favoured group of compounds of the present invention are of the formula (Ia) and pharmaceutically acceptable salts thereof.

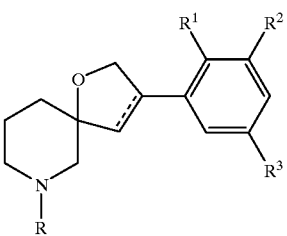

(Ia)

wherein R, R$^1$, R$^2$ and R$^3$ are as defined in relation to formula (I) and the broken line is an optional double bond.

Another favoured group of compounds of the present invention are of the formula (Ib) and pharmaceutically acceptable salts thereof:

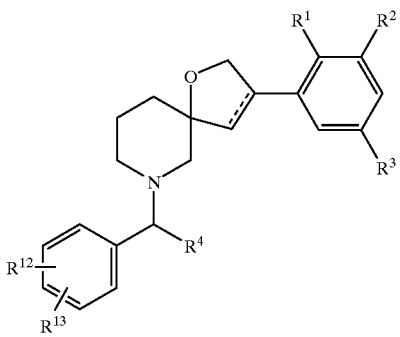

(Ib)

wherein $R^1$, $R^2$, $R^3$ and $R^4$ are as defined in relation to formula (I), the broken line is an optional double bond, and $R^{12}$ and $R^{13}$ are each independently hydrogen, halogen or $C_{1-6}$alkoxy.

Another favoured group of compounds of the present invention are of the formula (Ic) and pharmaceutically acceptable salts thereof:

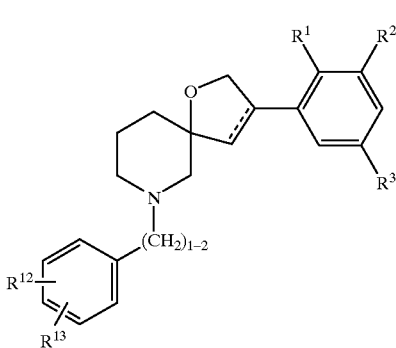

(Ic)

wherein $R^1$, $R^2$ and $R^3$ are defined in relation to formula (I), the broken line is an optional double bond, and $R^{12}$ and $R^{13}$ are each independently hydrogen, halogen or $C_{1-6}$alkoxy.

Where Ar represents an optionally substituted 5- or 6-membered heterocyclic ring containing 1 to 3 nitrogen atoms, suitable rings include: pyrrole, pyrazole, imidazole, 1,2,3-triazole, 1,2,4-triazole, pyridine, pyridazine. pyrimidine, pyrazine and 1,3,5-triazine.

With respect to compounds of the formula (I), Z (where present), may be a linear, branched or cyclic group. Favourably Z contains 1 to 4 carbon atoms and most favourably 1 or 2 carbon atoms. A particularly favourable group Z is $CH_2$.

With respect to compounds of the formula (I), $R^7$ may aptly be a $C_{1-4}$alkyl group or a $C_{2-4}$alkyl group substituted by a hydroxyl or $C_{1-2}$alkoxy group. $R^8$ may aptly be a $C_{1-4}$alkyl group or a $C_{2-4}$alkyl group substituted by a hydroxyl or $C_{1-2}$alkoxy group, or $R^7$ and $R^8$ may be linked so that, together with the nitrogen atom to which they are attached, they form an azetidinyl, pyrrolidinyl, piperidyl, morpholino, thiomorpholino, piperazino or piperazino group substituted on the nitrogen atom by a $C_{1-4}$alkyl group or a $C_{2-4}$alkyl group substituted by a hydroxy or $C_{1-2}$alkoxy group.

Where the group $NR^7R^8$ represents a heteroaliphatic ring of 4 to 7 ring atoms and said ring contains a double bond, a particularly preferred group is 3-pyrroline.

Where the group $NR^7R^8$ represents a non-aromatic azabicyclic ring system, such a system may contain between 6 and 12, and preferably between 7 and 10, ring atoms. Suitable rings include 5-azabicyclo[2.1.1]hexyl, 5-azabicyclo[2.2.1]heptyl, 6-azabicyclo[3.2.1]octyl, 2-azabicyclo[2.2.2]octyl, 6-azabicyclo[3.2.2]nonyl, 6-azabicyclo[3.3.1]nonyl, 6-azabicyclo[3.2.2]decyl. 7-azabicyclo[4.3.1]decyl, 7-azabicyclo[4.4.1]undecyl and 8-azabicyclo[5.4.1]dodecyl, especially 5-azabicyclo[2.2.1]heptyl and 6-azabicyclo[3.2.1]octyl.

Where $R^8$ represents a $C_{2-4}$alkyl group substituted by a 5 or 6 membered heteroaliphatic ring containing one or two heteroatoms selected from N, O and S, suitable rings include pyrrolidino, piperidino, piperazino, morpholino, or thiomorpholino. Particularly preferred are nitrogen containing heteroaliphatic rings, especially pyrrolidino and morpholino rings.

In the group $ZNR^7R^8$, Z is preferably $CH_2$ or $CH_2CH_2$, and especially $CH_2$.

The group $NR^7R^8$ preferably represents amino, methylamino, dimethylamino, diethylamino, azetidinyl, pyrrolidino and morpholino.

Where $R^1$ and $R^2$ are attached to adjacent carbon atoms and are joined together such that there is formed a 5- or 6-membered saturated or unsaturated ring containing one or two oxygen atoms, there is formed a fused ring moiety such as 2,3-dihydrobenzofuran, benzofuran, 3,4-dihydro-2H-1-benzopyran, 2H-1-benzopyran, 1,3-benzodioxole or 1,4-benzodioxan. Particularly preferred is 2,3-dihydrobenzofuran where the oxygen atom corresponds to the position of $R^1$.

Where $R^1$ and $R^2$ are attached to adjacent carbon atoms and are joined together such that there is formed a 5-membered saturated or unsaturated ring containing one nitrogen atom and optionally one oxygen atom, there is formed a fused ring moiety such as indole, indoline, benzoxazole, benzoxazoline, benzisoxazole or benzisoxazoline.

Certain particularly apt compounds of the present invention include those wherein $R^3$ is a group selected from pyrrole, furan, thiophene, pyridine, pyrazole, imidazole, oxazole, isoxazole, thiazole, isothiazole, pyrazine, pyrimidine, pyridazine, triazole, oxadiazole, thiadiazole, triazine, and tetrazole, each heteroaryl group being optionally substituted as previously defined.

Particularly preferred compounds of the present invention are those wherein $R^3$ is a group selected from furan, pyridine, pyrimidine, imidazole, triazole and tetrazole, each heteroaryl group being optionally substituted as previously defined.

As used herein, the term "alkyl" or "alkoxy" as a group or part of a group means that the group is straight or branched. Examples of suitable alkyl groups include methyl, ethyl, n-propyl, i-propyl, n-butyl, s-butyl and t-butyl. Examples of suitable alkoxy groups include methoxy, ethoxy, n-propoxy, i-propoxy, n-butoxy, s-butoxy and t-butoxy.

As used herein, the terms "fluoro$C_{1-6}$alkyl" and "fluoro$C_{1-6}$alkoxy" means a $C_{1-6}$alkyl or $C_{1-6}$alkoxy group in which one or more (in particular, 1 to 3) hvyrogen atoms have been replaced by fluorine atoms. Similarly, the term "fluoro$C_{1-4}$alkyl" means a $C_{1-4}$alkyl group in which one or more (in particular 1 to 3) hydrogen atoms have been replaced by fluorine atoms. Particularly preferred are fluoro$C_{1-3}$alkyl and fluoro$C_{1-3}$alkoxy groups, for example, $CF_3$, $CH_2CH_2F$, $CH_2CHF_2$, $CH_2CF_3$, $OCF_3$, $OCH_2CH_2F$, $OCH_2CHF_2$ or $OCH_2CF_3$, and most especially $CF_3$, $OCF_3$ and $OCH_2CF_3$.

As used herein, the term "hydroxy$C_{1-4}$alkyl" means a $C_{1-4}$alkyl group in which one or more (in particular 1 or 2, especially 1) hydrogen atoms have been replaced by hydroxy groups, for example CH$_2$OH or CH$_2$CH$_2$OH.

The cycloalkyl groups referred to herein may represent, for example, cyclopropyl, cyclobutyl, cyclopentyl or cyclohexyl. A suitable cycloalkylalkyl group may be, for example, cyclopropylmethyl.

Similarly cycloalkoxy groups referred to herein may represent, for example, cyclopropoxy or cyclobutoxy. A suitably cycloalkylalkoxy group may be, for example, cyclopropylmethoxy.

As used herein, the terms "alkenyl" and "alkynyl" as a group or part of a group means that the group is straight or branched. Examples of suitable alkenyl groups include vinyl and allyl. A suitable alkynyl group is propargyl.

When used herein the term "halogen" means fluorine, chlorine, bromine and iodine. The most apt halogens are fluorine and chlorine of which fluorine is preferred, unless otherwise stated.

Specific compounds within the scope of this invention include:

7-benzyl-3-(2-methoxyphenyl)-1-oxa-7-azaspiro[4,5] dec-3-ene;

7-benzyl-3-(2-methoxy-5-(5-trifluoromethyl-1H-tetrazol-1-yl)phenyl)-1-oxa-7-azaspiro [4,5]dec-3-ene;

7-benzyl-3-(2-methoxy-5-(1H-tetrazol-1-yl)phenyl)-1oxa-7-azaspiro[4,5]dec-3-ene;

7-benzyl-3-(2-methoxy-5-(4-pyridyl)phenyl)-1-oxa-7-azaspiro[4,5]dec-3-ene;

7-benzyl-3-(2-methoxy-5-cyanophenyl)-1-oxa-7-azaspiro[4,5]dec-3-ene:

7-benzyl-3-(2-methoxy-5-trifluoromethoxypheny)-1oxa-7-azaspiro[4,5]dec-3-ene:

7-benzyl-3-(2-methoxy-5-(3-trifluoromethyl-4H-1,2,4-triazol-4-yl)phenyl)-1-oxa-7-azaspiro [4,5]-dec-3-ene;

7-benzyl-3-(2-methoxy-5-(2-trifluoromethyl-1H-imidazol-1-yl)phenyl)-1-oxa-7-azaspiro [4,5]-dec-3-ene;

7-benzyl-3-(2-methoxy-5-benzyloxyphenyl)-1-oxa-7-azaspiro[4,5]dec-3-ene;

7-benzoyl-3-(2-methoxy-5-(5-trifluoromethyl-1H-tetrazol-1-yl)phenyl)-1-oxa-7-azaspiro [4,5]dec-3-ene;

7-(3,4-dichlorobenzyl)-3-(2-methoxy-5-(5-trifluoromethyl-1H-tetrazol-1-yl)phenyl)-1-oxa-7-azaspiro [4,5]dec-3-ene;

7-(4-pyridyl)-3-(2-methoxy-5-(5-trifluoromethyl-1H-tetrazol-1-yl)phenyl)-1-oxa-7-azaspiro [4,5]dec-3-ene;

7-(3-pyridyl)-3-(2-methoxy-5-(5-trifluoromethyl-1H-tetrazol-1-yl)phenyl)-1-oxa-7-azaspiro [4,5]dec-3-ene;

7-(2-pyridyl)-3-(2-methoxy-5-(5-trifluoromethyl-1H-tetrazol-1-yl)phenyl)-1-oxa-7-azaspiro [4,5]dec-3-ene;

7-(2-methoxybenzyl)-3-(2-methoxy-5-(5-trifluoromethyl-1H-tetrazol-1-yl)phenyl)-1-oxa-7-azaspiro [4,5]dec-3-ene;

7-(1-phenylethyl)-3-(2-methoxy-5-(5-trifluoromethyl-1H-tetrazol-1-yl)phenyl)-1-oxa-7-spiro [4,5]dec-3-ene;

7-(2-phenylethyl)-3-(2-methoxy-5-(5-trifluoromethyl-1H-tetrazol-1-yl)phenyl)-1-oxa-7-azaspiro [4,5]dec-3-ene;

cyclohexylmethyl-3-(2-methoxy-5-(5-trifluoromethyl-1H-tetrazol-1-yl)phenyl)-1-oxa-7-azaspiro [4,5]dec-3-ene;

7-(5-dimethylaminomethyl-1H-1,2,3-triazol-4-yl)methyl-3-(2-methoxy-5-(5-trifluoromethyl-1H-tetrazol-1-yl) phenyl)-1-oxa-7-azaspiro [4,5]dec-3-ene;

(±)-(3R*, 5R*)-7-benzyl-3-(2-methoxy-5-(5-trifluoromethyl-1H-tetrazol-1-yl)phenyl)-1-oxa-7-azaspiro [4,5]decane;

(±)-(3S*, 5R*)-7-benzyl-3-(2-methoxy-5-(5-trifluoromethyl-1H-tetrazol-1-yl)phenyl)-1-oxa-7-azaspiro [4,5]decane;

(±)-(3R*, 5R*)-7-benzoyl-3-(2-methoxy-5-(5-trifluoromethyl-1H-tetrazol-1-yl)phenyl)-1-oxa-7-azaspiro [4,5]decane;

(±)-(3R*, 5R*)-7-(2-phenylethyl)-3-(2-methoxy-5-(5-trifluoromethyl-1H-tetrazol-1-yl)phenyl)-1-oxa-7-azasphiro [4,5]decane; and pharmaceutically acceptable salts thereof.

In a further aspect of the present invention, the compounds of formula (I) may be prepared in the form of a pharmaceutically acceptable salt, especially an acid addition salt.

For use in medicine, the salts of the compounds of formula (I) will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, fumaric acid, p-toluenesulphonic acid, maleic acid, succinic acid, acetic acid, citric acid, tartaric acid, carbonic acid, phosphoric acid or sulphuric acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bundgaard, Elsevier, 1985.

A prodrug may be a pharmacologically inactive derivative of a biologically active substance (the "parent drug" or "parent molecule") that requires transformation within the body in order to release the active drug, and that has improved delivery properties over the parent drug molecule. The transformation in vivo may be, for example, as the result of some metabolic process, such as chemical or enzymatic hydrolysis of a carboxylic, phosphoric or sulphate ester, or reduction or oxidation of a susceptible functionality.

The present invention includes within its scope solvates of the compounds of formula (I) and salts thereof, for example, hydrates.

The compounds according to the invention may have at least two asymmetric centres, and may accordingly exist both as enantiomers and as diastereoisomers. It is to be understood that all such isomers and mixtures thereof are encompassed within the scope of the present invention.

The compounds of the formula (I), (Ia), (Ib), (Ic) and (Id) will have the preferred stereochemistry of the 5-position that is possessed by the late eluting enantiomer of Example 2.

According to a yet further preference, the compounds of the formula (I), (Ia), (Ib), (Ic) and (Id), in which Y is —$CH_2$— or —$CH_2CH_2$—, will have the relative stereochemistry of the 3- and 5-positions that is possessed by the compound of Example 22 (i.e. 3-(R),5-(R) or 3-(S),5-(S)):

It will be appreciated that the preferred definitions of the various substituents recited herein may be taken alone or in combination, and apply to the generic formula for compounds of the present invention as well as to the preferred classes of compound represented by formulae (Ia), (Ib), (Ic) and (Id).

The present invention further provides pharmaceutical compositions comprising one or more compounds of formula (I) in association with a pharmaceutically acceptable carrier or excipient.

Preferably the compositions according to the invention are in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Preferred compositions for administration by injection include those comprising a compound of formula (I), as the active ingredient, in association with a surface-active agent (or wetting agent or surfactant) or in the form of an emulsion (as a water-in-oil or oil-in-water emulsion).

Suitable surface-active agents include, in particular, non-ionic agents, such as polyoxyethylenesorbitans (e.g. Tween™ 20, 40, 60, 80 or 85) and other sorbitans (e.g. Span™ 20, 40, 60, 80 or 85). Compositions with a surface-active agent will conveniently comprise between 0.05 and 5% surface-active agent, and preferably between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion will preferably comprise fat droplets between 0.1 and 1.0 μm, particularly 0.1 and 0.5 μm, and have a pH in the range of 5.5 to 8.0.

Particularly preferred emulsion compositions are those prepared by mixing a compound of formula (I) with Intralipid™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulised by use of inert gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

The present invention futher provides a process for the preparation of a pharmaceutical composition comprising a compound of formula (I), which process comprises bringing a compound of formula (I) into association with a pharmaceutically acceptable carrier or excilient.

The compounds of formula (I) are of value in the treatment of a wide variety of clinical conditions which are characterised by the presence of an excess of tachykinin, in particular substance P, activity.

Thus, for example, an excess of tachykinin, and in particular substance P, activity is implicated in a variety of disorders of the central nervous system. Such disorders include mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder; anxiety disorders, such as panic disorder with or without agoraphobia, agoraphobia without history of panic disorder, specific phobias, for example, specific animal phobias, social phobias, obsessive-compulsive disorder, stress disorders including post-traumatic stress disorder and acute stress disorder, and generalised anxiety disorders; chizophrenia and other psychotic disorders, for example, schizophreniform disorders, schizoaffective disorders, delusional disorders, brief psychotic disorders, shared psychotic disorders and psychotic disorders with delusions or hallucinations: delerium, dementia, and amnestic and other cognitive or neurodegenerative disorders, such as Alzheimer's disease, senile dementia, dementia of the Alzheimer's type, vascular dementia, and other dementias, for example, due to HIV disease, head trauma, Parkinson's disease, Huntington's disease, Pick's disease, Creutzfeldt-Jakob disease, or due to multiple aetiologies; Parkinson's disease and other extra-pyramidal movement disorders such as medication-induced movement disorders, for example, neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremour; substance-related disorders arising from the use of alcohol, amphetamines (or amphetamine-like substances) caffeine, cannabis, cocaine, hallucinogens, inhalants and aerosol propellants, nicotine, opioids, phenylglycidine derivatives, sedatives, hypnotics, and anxiolytics, which substance-related disorders include dependence and abuse, intoxication, withdrawal, intoxication delerium, withdrawal delerium, persisting dementia, psychotic disorders, mood disorders, anxiety disorders, sexual dysfunction and sleep disorders; epilepsy; Down's syndrome; demyelinating diseases such as MS and ALS and other neuropathological disorders such as peripheral neuropathy, for example diabetic and chemotherapy-induced neuropathy; and postherpetic neuralgia, trigeminal neuralgia, segmental or intercostal neuralgia and other neuralgias; and cerebral vascular disorders due to acute or chronic cerebrovascular damage such as cerebral infarction, subarachnoid haemorrhage or cerebral oedema.

Tachykinin, and in particular substance P, activity is also involved in nociception and pain. The compounds of the present invention will therefore be of use in the prevention or treatment of diseases and conditions in which pain predominates, including soft tissue and peripheral damage, such as acute trauma, osteoarthritis, rheumatoid arthritis, musculo-skeletal pain, particularly after trauma, spinal pain, dental pain, myofascial pain syndromes, headache, episiotomy pain, and burns, deep and visceral pain, such as heart pain, muscle pain, eye pain, orofacial pain, for example, odontalgia, abdominal pain, gynaecological pain, for example, dysmenorrhoea, and labour pain; pain associated with nerve and root damage, such as pain associated with peripheral nerve disorders, for example, nerve entrapment and brachial plexus avulsions, amputation, peripheral neuropathies, tic douloureux, atypical facial pain, nerve root damage, and arachnoiditis; pain associated with carcinoma, often referred to as cancer pain; central nervous system pain, such as pain due to spinal cord or brain stem damage; low back pain; sciatica; ankylosing spondylitis, gout; and scar pain.

Tachykinin, and in particular substance P. antagonists may also be of use in the treatment of respiratory diseases, particularly those associated with excess mucus secretion, such as chronic obstructive airways disease, bronchopneumonia, chronic bronchitis, cystic fibrosis and asthma, adult respiratory distress syndrome, and bronchospasm; inflammatory diseases such as inflammatory bowel disease, psoriasis, fibrositis, osteoarthritis, rheumatoid arthritis, pruritis and sunburn; allergies such as eczema and rhinitis; hypersensitivity disorders such as poison ivy; ophthalmic diseases such as conjunctivitis, vernal conjunctivitis, and the like; ophthalmic conditions associated with cell proliferation such as proliferative vitreoretinopathy; cutaneous diseases such as contact dermatitis, atopic dermatitis, urticaria, and other eczematoid dermatitis.

Tachykinin, and in particular substance P. antagonists may also be of use in the treatment of neoplasms, including breast tumours, neuroganglioblastomas and small cell carcinomas such as small cell lung cancer.

Tachykinin, and in particular substance P. antagonists may also be of use in the treatment of gastrointestinal (GI) disorders, including inflammatory disorders and diseases of the GI tract such as gastritis, gastroduodenal ulcers, gastric carcinomas, gastric lymphomas, disorders associated with the neuronal control of viscera, ulcerative colitis, Crohn's disease, irritable bowel syndrome and emesis, including acute, delayed or anticipatory emesis such as emesis induced by chemotherapy, radiation, toxins, viral or bacterial infections, pregnancy, vestibular disorders, for example, motion sickness, vertigo, dizziness and Meniere's disease, surgery, migraine, variations in intercranial pressure, gastro-oesophageal reflux disease, acid indigestion, over indulgence in food or drink, acid stomach, waterbrash or regurgitation, heartburn, for example, episodic, nocturnal or meal-induced heartburn, and dyspepsia.

Tachykinin, and in particular substance P. antagonists may also be of use in the treatment of a variety of other conditions including stress related somatic disorders; reflex sympathetic dystrophy such as shoulder/hand syndrome; adverse immunological reactions such as rejection of transplanted tissues and disorders related to immune enhancement or suppression such as systemic lupus erythematosus; plasma extravasation resulting from cytokine chemotherapy, disorders of bladder function such as cystitis, bladder detrusor hyper-reflexia and incontinence; fibrosing and collagen diseases such as scleroderma and eosinophilic fascioliasis; disorders of blood flow caused by vasodilation and vasospastic diseases such as angina, vascular headache, migraine and Reynaud's disease; and pain or nociception attributable to or associated with any of the foregoing conditions, especially the transmission of pain in migraine.

The compounds of formula (I) are also of value in the treatment of a combination of the above conditions, in particular in the treatment of combined post-operative pain and post-operative nausea and vomiting.

The compounds of formula (I) are particularly useful in the treatment of emesis, including acute, delayed or anticipatory emesis, such as emesis induced by chemotherapy, radiation, toxins, pregnancy, vestibular disorders, motion, surgery, migraine, and variations in intercranial pressure. Most especially, the compounds of formula (I) are of use in the treatment of emesis induced by antineoplastic (cytotoxic) agents including those routinely used in cancer chemotherapy, and emesis induced by other pharmacological agents. For example, rolipram.

Examples of such chemotherapeutic agents include alkylating agents, for example, nitrogen mustards, ethyleneimine compounds, alkyl sulphonates and other compounds with an alkylating action such as nitrosoureas, cisplatin and dacarbazine; antimetabolites, for example, folic acid, purine or pyrimidine antagonists; mitotic inhibitors, for example, vinca alkaloids and derivatives of podophyllotoxin; and cytotoxic antibiotics.

Particular examples of chemotherapeutic agents are described, for instance, by D. J. Stewart in *Nausea and*

*Vomiting: Recent Research and Clinical Advances,* Eds. J. Kucharczyk et al, CRC Press Inc., Boca Raton, Fla., USA (1991) pages 177–203, especially page 188. Commonly used chemotherapeutic agents include cisplatin, dacarbazine (DTIC), dactinomycin, mechlorethamine (nitrogen mustard), streptozocin, cyclophosphamide, carmustine (BCNU), lomustine (CCNU), doxorubicin (adriamycin), daunorubicin, procarbazine, mitomycin, cytarabine, etoposide, methotrexate, 5-fluorouracil, vinblastine, vincristine, bleomycin and chlorambucil [R. J. Gralla et at in *Cancer Treatment Reports* (1984) 68(1), 163–172].

The compounds of formula (I) are also of use in the treatment of emesis induced by radiation including radiation therapy such as in the treatment of cancer, or radiation sickness; and in the treatment of post-operative nausea and vomiting.

It will be appreciated that the compounds of formula (I) may be presented together with another therapeutic agent as a combined preparation for simultaneous, separate or sequential use for the relief of emesis. Such combined preparations may be, for example, in the form of a twin pack.

A further aspect of the present invention comprises the compounds of formula (I) in combination with a 5-$HT_3$ antagonist, such as ondansetron, granisetron or tropisetron, or other anti-emetic medicaments, for example, a dopamine antagonist such as metoclopramide or domperidone, or GABAs receptor agonists such as baclofen. Additionally, a compound of formula (I) either alone or in combination with one or more other anti-emetic therapeutic agents, may be administered in combination with an anti-inflammatory corticosteroid, such as dexamethasone, betamethasone, triamcinolone, triamcinolone acetonide, flunisolide, budesolide, or others such as those disclosed in U.S. Pat. Nos. 2,789,118, 2,990,401, 3,048,581, 3,126,375, 3,929,768, 3,996,359, 3,928,326 and 3,749,712. Dexamethasone (Decadron™) is particularly preferred. Furthermore, a compound of formula (I) may be administered in combination with a chemotherapeutic agent such as an alkylating agent, antimetabolite, mitotic inhibitor or cytotoxic antibiotic, as described above. In general, the currently available dosage forms of the known therapeutic agents for use in such combinations will be suitable.

When tested in the ferret model of cisplatin-induced emesis described by F. D. Tattersall et al, in *Eur. J. pharmacol.,* (1993) 250 R5-R6, the compounds of the present invention were found to attenuate the retching and vomiting induced by cisplatin.

The compounds of formula (I) are also particularly useful in the treatment of pain or nociception and/or inflammation and disorders associated therewith such as, for example, neuropathy, such as diabetic and chemotherapy-induced neuropathy, postherpetic and other neuralgias, asthma, osteroarthritis, rheumatoid arthritis and headache including migraine, acute or chronic tension headache, cluster headache, temporomandibular pain and maxillary sinus pain.

The compounds of formula (I) are also particularly useful in the treatment of depression including depressive disorders, for example, single episodic or recurrent major depressive disorders, and dysthymic disorders, depressive neurosis, and neurotic depression; melancholic depression including anorexia, weight loss, insomnia and early morning waking, and psychomotor retardation; atypical depression (or reactive depression) including increased appetite, hypersomnia, psychomotor agitation or irritability, anxiety and phobias; seasonal affective disorder; or bipolar disorders or manic depression, for example, bipolar I disorder, bipolar II disorder and cyclothymic disorder.

The present invention further provides a compound of formula (I) for use in therapy.

According to a further or alternative aspect, the present invention provides a compound of formula (I) for use in the manufacture of a medicament for the treatment of physiological disorders associated with an excess of tachykinins, especially substance P.

The present invention also provides a method for the the treatment or prevention of physiological disorders associated with an excess of tachykinins, especially substance P. which method comprises administration to a patient in need thereof of a tachykinin reducing amount of a compound of formula (I) or a composition comprising a compound of formula (I).

According to a further aspect of the present invention, it may be desirable to treat any of the aforementioned conditions with a combination of a compound according to the present invention and one or more other pharmacologically active agents suitable for the treatment of the specific condition. The compound of formula (I) and the other pharmacologically active agent(s) may be administered to a patient simultaneously, sequentially or in combination.

Thus, for example, for the treatment of respiratory diseases such as asthma, a compound of formula (I) may be used in conjunction with a bronchodilator, such as a β2-adrenergic receptor agonist or tachykinin antagonist which acts at NK-2 receptors. The compound of formula (I) and the bronchodilator may be administered to a patient simultaneously, sequentially or in combination.

Likewise, a compound of the present invention may be employed with a leukotriene antagonists, such as a leukotriene $D_4$ antagonist such as a compound selected from those disclosed in European patent specification nos. 0 480 717 and 0 604 114 and in U.S. Pat. Nos. 4,859,692 and 5,270,324. This combination is particularly useful in the treatment of respiratory diseases such as asthma, chronic bronchitis and cough.

The present invention accordingly provides a method for the treatment of a respiratory disease, such as asthma, which method comprises administration to a patient in need thereof of an effective amount of a compound of formula (I) and an effective amount of a bronchodilator.

The present invention also provides a composition comprising a compound of formula (I), a bronchodilator, and a pharmaceutically acceptable carrier.

It will be appreciated that for the treatment or prevention of migraine, a compound of the present invention may be used in conjunction with other anti-migraine agents, such as ergotamines or 5-$HT_1$ agonists, especially sumatriptan, naratriptan, zolmatriptan or rizatriptan.

Likewise, for the treatment of behavioural hyperalgesia, a compound of the present invention may be used in conjunction with an antagonist of N-methyl D-aspartate (NMDA), such as dizocilpine.

For the treatment or prevention of inflammatory conditions in the lower urinary tract, especially cystitis, a compound of the present invention may be used in conjunction with an antiinflammatory agent such as a bradykinin receptor antagonist.

It will be appreciated that for the treatment or prevention of pain or nociception, a compound of the present invention may be used in conjunction with other analgesics, such as acetaminophen (paracetamol), aspirin and other NSAIDs and, in particular, opioid analgesics, especially morphine. Specific anti-inflammatory agents include diclofenac, ibuprofen, indomethacin, ketoprofen, naproxen, piroxicam and sulindac. Suitable opioid analgesics of use in conjunction with a compound of the present invention include morphine, codeine, dihydrocodeine, diacetylmorphine, hydrocodone, hydromorphone, levorphanol, oxymorphone, alfentanil, buprenorphine, butorphanol, fentanyl, sufentanyl, meperidine, methadone, nalbuphine, propoxyphene and pentazocine; or a pharmaceutically acceptable salt thereof. Preferred salts of these opioid analgesics include morphine sulphate, morphine hydrochloride, morphine tartrate, codeine phosphate, codeine sulphate, dihydrocodeine bitartrate, diacetylmorphine hydrochloride, hydrocodone bitartrate, hydromorphone hydrochloride, levorphanol tartrate, oxymorphone hydrochloride, alfentanil hydrochloride, buprenorphine hydrochloride, butorphanol tartrate, fentanyl citrate, meperidine hydrochloride, methadone hydrochloride, nalbuphine hydrochloride, propoxyphene hydrochloride, propoxyphene napsylate (2-naphthalenesulphonic acid (1:1) monohydrate), and pentazocine hydrochloride.

Therefore, in a further aspect of the present invention, there is provided a pharmaceutical composition comprising a compound of the present invention and an analgesic, together with at least one pharmaceutically acceptable carrier or excipient.

In a further or alternative aspect of the present invention, there is provided a product comprising a compound of the present invention and an analgesic as a combined preparation for simultaneous, separate or sequential use in the treatment or prevention of pain or nociception.

It will be appreciated that for the treatment of depression or anxiety, a compound of the present invention may be used in conjunction with other anti-depressant or anti-anxiety agents.

Suitable classes of anti-depressant agent include norepinephrine reuptake inhibitors, selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists and atypical anti-depressants.

Suitable norepinephrine reuptake inhibitors include tertiary amine tricyclics and secondary amine tricyclics. Suitable examples of tertiary amine tricyclics include: amitriptyline, clomipramine, doxepin, imipramine and trimipramine, and pharmaceutically acceptable salts thereof. Suitable examples of secondary amine tricyclics include: amoxapine, desipramine, maprotiline, nortriptyline and protriptyline, and pharmaceutically acceptable salts thereof.

Suitable selective serotonin reuptake inhibitors include: fluoxetine, fluvoxamine, paroxetine and sertraline, and pharmaceutically acceptable salts thereof.

Suitable monoamine oxidase inhibitors include: isocarboxazid, phenelzine, tranylcypromine and selegiline, and pharmaceutically acceptable salts thereof.

Suitable reversible inhibitors of monoamine oxidase include: moclobemide, and pharmaceutically acceptable salts thereof.

Suitable serotonin and noradrenaline reuptake inhibitors of use in the present invention include: venlafaxine, and pharmaceutically acceptable salts thereof.

Suitable CRF antagonists include those compounds described in International Patent Specification Nos. WO 94/13643, WO 94/13644, WO 94/13661, WO 94/13676 and WO 94/13677.

Suitable atypical anti-depressants include: bupropion, lithium, nefazodone, trazodone and viloxazine, and pharmaceutically acceptable salts thereof.

Suitable classes of anti-anxiety agent include benzodiazepines and $5\text{-HT}_{1A}$ agonists or antagonists, especially $5\text{-HT}_{1A}$ partial agonists, and corticotropin releasing factor (CRF) antagonists.

Suitable benzodiazepines include: alprazolam, chlordiazepoxide, clonazepam, chlorazepate, diazepam, halazepam, lorazepam, oxazepam and prazepam, and pharmaceutically acceptable salts thereof.

Suitable $5\text{-HT}_{1A}$ receptor agonists or antagonists include, in particular, the $5\text{-HT}_{1A}$ receptor partial agonists buspirone, flesinoxan, gepirone and ipsapirone, and pharmaceutically acceptable salts thereof.

Therefore, in a further aspect of the present invention, there is provided a pharmaceutical composition comprising a compound of the present invention and an anti-depressant or anti-anxiety agent, together with at least one pharmaceutically acceptable carrier or excipient.

In a further or alternative aspect of the present invention, there is provided a product comprising a compound of the present invention and an anti-depressant or anti-anxiety agent as a combined preparation for simultaneous, separate or sequential use for the treatment or prevention of depression and/or anxiety.

It will be appreciated that for the treatment or prevention of eating disorders, including obesity, bulimia nervosa and compulsive eating disorders, a compound of the present invention may be used in conjunction with other anorectic agents.

The present invention accordingly provides the use of a compound of formula (I) and an anorectic agent for the manufacture of a medicament for the treatment or prevention of eating disorders.

The present invention also provides a method for the treatment or prevention of eating disorders, which method comprises administration to a patient in need of such treatment an amount of a compound of formula (I) and an amount of an anorectic agent, such that together they give effective relief.

In a further aspect of the present invention, there is provided a pharmaceutical composition comprising a compound of formula (I) and an anorectic agent, together with at least one pharmaceutically acceptable carrier or excipient.

It will be appreciated that the compound of formula (I) and anorectic agent may be present as a combined preparation for simultaneous, separate or sequential use for the treatment or prevention of eating disorders. Such combined preparations may be, for example, in the form of a twin pack.

In a further or alternative aspect of the present invention, there is therefore provided a product comprising a compound of formula (I) and an anorectic agent as a combined preparation for simultaneous, separate or sequential use in the treatment or prevention of eating disorders.

In a further embodiment of the present invention there is provided the use of a compound of formula (I) and an anorectic agent for the manufacture of a medicament for the treatment or prevention of obesity.

The present invention also provides a method for the treatment or prevention of obesity, which method comprises administration to a patient in need of such treatment an amount of a compound of formula (I) and an amount of an anorectic agent, such that together they give effective relief.

In an alternative embodiment of the present invention there is provided the use of a compound of formula (I) and an anorectic agent for the manufacture of a medicament for the treatment or prevention of bulimia nervosa.

The present invention also provides a method for the treatment or prevention of bulimia nervosa, which method comprises administration to a patient in need of such treatment an amount of a compound of formula (I) and an amount of an anorectic agent, such that together they give effective relief.

In a further embodiment of the present invention there is provided the use of a compound of formula (I) and an anorectic agent for the manufacture of a medicament for the treatment or prevention of compulsive eating disorders.

The present invention also provides a method for the treatment or prevention of compulsive eating disorders, which method comprises administration to a patient in need of such treatment an amount of a compound of formula (I) and an amount of an anorectic agent, such that together they give effective relief.

In an alternative embodiment of the present invention there is provided the use of a compound of formula (I) and an anorectic agent for the manufacture of a medicament for reducing the total body fat mass in an obese mammal, especially a human.

The present invention also provides a method for reducing the total body fat mass in an obese mammal, especially a human, which method comprises administration to a patient in need of such treatment an amount of a compound of formula (I) and an amount of an anorectic agent, such that together they give effective relief.

Suitable anoretic agents of use in combination with a compound of the present invention include but are not limited to, aminorex, amphechloral amphetamine, benzphetamine, chlorphentermine, clobenzorex, cloforex clominorex, clortermine, cyclexedrine, dexfenfluramine, dextroamphetamine diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudophedrine, pentorex, phendimetrazine, phenmetrazine, phentermine, phenylpropanolamine, picilorex and sibutramine; and pharmaceutically acceptable salts thereof.

Particularly preferred anorectic agents include amphetamine and derivatives thereof such as amphetamine, benzphetamine, chlorphentermine, clominorex, clortermine, cyclexedrine, dexfenfluramine, dextroamphetamine diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudophedrine, pentorex, phendimetrazine, phenmetrazine, phentermine, phenylpropanolamine, picilorex and sibutramine; and pharmaceutically acceptable salts thereof.

A particularly suitable class of anorectic agent are the halogenated amphetamine derivatives, including cloforex, clortermine, dexfenfluramine, fenfluramine, picilorex and sibutramine, and pharmaceutically acceptable salts thereof.

Particularly preferred halogenated amphetamine derivatives of use in combination with a compound of the present invention include, fenfluramine and dexfenfluramine, and pharmaceutically acceptable salts thereof.

It will be appreciated that for the treatment or prevention of obesity, the compounds of the present invention may also be used in combination with a selective serotonin reuptake inhibitor (SSRI)

The present invention accordingly provides the use of a compound of formula (I) and an SSRI for the manufacture of a medicament for the treatment or prevention of obesity.

The present invention also provides a method for the treatment or prevention of obesity, which method comprises administration to a patient in need of such treatment an amount of a compound of formula (I) and an amount of an SSRI, such that together they give effective relief.

In a further aspect of the present invention, there is provided a pharmaceutical composition for the treatment or prevention of obesity comprising pharmaceutically acceptable carrier or excipient.

It will be appreciated that the compound of formula (I) and SSRI may be prevent as a cobine preparation for simultaneous, separate or sequential use for the treatment or prevention of obesity. Such combined preparation may be for example, in the form of a twin pack.

In a further or alternative embodiment of the present invention, there is therefore provided a product comprising a compound of formula (I) and an SSRI as a combined preparation for simultaneous, separate or sequential use in the treatment or prevention of obesity.

In an alternative embodiment of the present invention, there is provided the use of a compound of formula (I) and an SSRI for the manufacture of a medicament for reducing the total body fat mass in an obese mammal, especially a human.

The present invention also provides a method for reducing the total body fat mass in an obese mammal, especially a human, which method comprises administration to the mammal an amount of a compound of formula (I) and an amount of an SSRI, such that together they give effective relief.

In a further aspect of the present invention, there is provided a pharmaceutical composition for reducing the total body fat mass in an obese mammal, especially a human, comprising a compound of formula (I) and an SSRI, together with at least one pharmaceutically acceptable carrier or excipient.

Suitable selective serotonin reuptake inhibitors of use in combination with a compound of the present invention include: fluoxetine, fluvoxamine, paroxetine and sertraline, and pharmaceutically acceptable salts thereof.

As used herein "obesity" refers to a condition whereby a mammal has a Body Mass Index (BMI), which is calculated as weight per height squared ($kg/m^2$), of at least 25.9. Conventionally, those persons with normal weight, have a BMI of 19.9 to less than 25.9.

The obesity herein may be due to any cause, whether genetic or environmental. Examples of disorders that may result in obesity or be the cause of obesity include overeating and bulimia, polycystic ovarian disease, craniopharyngioma, the Prader-Willi Syndrome, Frohlich's syndrome, Type II diabetes, GH-deficient subjects, normal variant short stature. Turner's syndrome, and other pathological conditions showing reduced metabolic activity or a decrease in resting energy expenditure as a percentage of total fat-free mass, e.g. children with acute lymphoblastic leukemia.

"Treatment" (of obesity) refers to reducing the BMI of the mammal to less than about 25.9 and maintaining that weight for at least 6 months. The treatment suitably results in a reduction in food or calorie intake by the mammal.

"Prevention" (of obesity) refers to preventing obesity from occurring if the treatment is administered prior to the onset of the obese condition. Moreover, if treatment is commenced in already obese subjects, such treatment is expected to prevent, or to prevent the progression of, the medical sequelae of obesity, such as e.g., arteriosclerosis, Type II diabetes, polycycstic ovarian disease, cardiovascular diseases, osteoarthritis, dermatological disorders, hypertension, insulin resistance, hypercholesterolemia, hypertriglyceridemia, and cholelithiasis.

Thus, in one aspect, this invention relates to the inhibition and/or complete suppression of lipogenesis in obese mammals, i.e., the excessive accumulation of lipids in fat cells, which is one of the major features of human and animal obesity, as well as loss of total body weight. In another aspect, the invention ameliorates the conditions that are a consequence of the disease, such as preventing or arresting the progression of polycystic ovarian disease so that the patient is no longer infertile, and increasing the insulin sensitivity and/or decreasing or eliminating the need or usage of insulin in a diabetic patient, e.g., one with adult-onset diabetes or Type II diabetes.

A further aspect of the present invention comprises the use of a compound of formula (I) for achieving a chronobiologic (circadian rhythm phase-shifting) effect and alleviating circadian rhythm disorders in a mammal. The present invention is further directed to the use of a compound of formula (I) for blocking the phase-shifting effects of light in a mammal.

The present invention further relates to the use of a compound of formula (I) for enhancing or improving sleep quality, in particular by increasing sleep efficiency and augmenting sleep maintenance, as well as for preventing and treating sleep disorders and sleep disturbances, in a mammal.

In a preferred embodiment, the present invention provides a method for the phase advance or phase delay in the circadian rhythm of a subject which comprises administering to the subject an appropriate amount of a compound of formula (I) or a pharmaceutically acceptable salt thereof.

The administration to a subject of an appropriate amount of a compound of formula (I) is useful, for example, in the prevention or treatment of the following conditions to achieve chronobiologic effects and/or to alleviate circadian rhythm phase disturbances: disorders of the sleep-wake schedule; jet lag; shift work; people who have a maladaption to work and off-work schedules; medical residents, nurses, firemen, policemen, or those whose duties require alertness and wakefulness at evening or nighttime hours, or those deprived of sleep for various periods because of their duties or responsibilities; animal workers; the infantry, or other members of the armed forces whose duties require extreme levels of alertness and wakefulness, and those who may be sleep deprived in the performance of these duties; submariners, or people confined for research, exploration or industrial purposes below the seas; miners, spelunkers, researchers or those confined beneath the Earth; astronauts in orbit around the Earth, on missions in space to the Earth's moon or to the planets or out of the solar system, or in training for such missions; the blind or sight-impaired or those persons whose ability to distinguish differences in light and dark may be permanently or temporarily impaired; psychiatric patients; insomniacs; the comatose, or those who need to maintained in a state of unconsciousness for medical, psychiatric or other reasons; residents of the far North or Antartica, or those persons who live in a climate or climates which possess abnormal amounts of light or darkness; those suffering from seasonal affective disorder (SAD), winter depression, or other forms of depression; the aged; Alzheimer's disease patients, or those suffering from other forms of dementia; patients who require dosages of medication at appropriate times in the circadian cycles; patients suffering from delayed sleep phase syndrome, advanced sleep phase syndrome, or non-24 hour sleep phase syndrome; and patients suffering from primary or secondary insomnia or circadian rhythm-related insomnia. The present invention is useful, for example, in the prevention or treatment of conditions associated with circadian rhythmicity as well as mental and physical disorders associated with travel across time zones and with rotating shift-work schedules.

In a preferred embodiment, this present invention provides a method for the prevention or treatment of a circadian rhythm disorder in a mammal, including time-zone change (jet-lag) syndrome, shift-work sleep disorder, delayed sleep-phase syndrome, advanced sleep-phase syndrome, and non-24-hour sleep-wake disorder, which comprises administering to the mammal an effective amount of a compound of formula (I) or a pharmaceutically acceptable salt thereof.

In another preferred embodiment, the present invention provides a method for shortening the time of retrainment of circadian rhythms in a subject following a shift in the sleep-wake cycle which comprises administering to the subject an appropriate amount of a compound of formula (I) or a pharmaceutically acceptable salt thereof.

In a more preferred embodiment, the present invention provides a method for alleviating the effects of jet lag in a traveller, especially a mammal, which comprises administering to the traveller an alertness increasing amount of a compound of formula (I) or a pharmaceutically acceptable salt thereof. The purpose of this embodiment is to assist the body to adjust physiologically to the changes in sleep and feeding patterns when crossing several time zones.

In another more preferred embodiment, the present invention provides a method for resetting the internal circadian clock in a subject, for example shift workers changing from a day to a night shift or vice versa, which comprises administering to the subject an appropriate amount of a compound of formula (I) or a pharmaceutically acceptable salt thereof.

The present invention is further directed to the use of a compound of formula (I) or a pharmaceutically acceptable salt thereof, for enhancing or improving sleep quality as well as preventing and treating sleep disorders and sleep disturbances in a mammal. In particular, the present invention provides a method for enhancing or improving sleep quality by increasing sleep efficiency and augmenting sleep maintenance. In addition, the present invention provides a method for preventing and treating sleep disorders and sleep disturbances in a mammal which comprising the administration of a compound of formula (I) or a pharmaceutically acceptable salt thereof. The present invention is useful for the treatment of sleep disorders, including Disorders of Initiating and Maintaining Sleep (insomnia) ("DIMS") which can arise from psychophysiological causes, as a consequence of psychiatric disorders (particularly related to anxiety), from drugs and alcohol use and abuse (particularly during withdrawal stages), childhood onset DIMS, nocturnal myocionus and restless legs and non specific REM disturbances as seen in ageing.

The following outcomes in a subject which are provided by the present invention may be correlated to enhancement in sleep quality: an increase in the value which is calculated from the time that a subject sleeps divided by the time that a subject is attempting to sleep; a decrease in sleep latency (the time it takes to fall asleep); a decrease in the number of awakenings during sleep; a decrease in the time spent awake following the initial onset of sleep; an increase in the total amount of sleep; an increase the amount and percentage of REM sleep; an increase in the duration and occurrence of REM sleep; a reduction in the fragmentation of REM sleep; an increase in the amount and percentage of slow-wave (i.e. stage 3 or 4) sleep; an increase in the amount and percentage of stage 2 sleep; a decrease in the number of awakenings, especially in the early morning; an increase in daytime alertness; and increased sleep maintenance. Secondary outcomes which may be provided by the present invention included enhanced cognitive function and increased memory retention.

The present invention is further useful for the prevention and treatment of sleep disorders and sleep disturbances including sleep problems associated with insomnia, hypersomnia, sleep apnea, narcolepsy, nocturnal myoclonus, REM sleep interruptions, jet-lag, shift workers' sleep disturbances, dysomnias, nigh terror, insomnias associated with depression or with emotional/mood disorders, dysfunctions associated with sleep (parasomnias), as well as sleep walking and enuresis, as well as sleep disorders which accompany aging. Sleep disorders and sleep disturbances are generally characterized by difficulty in initiating or maintaining sleep or in obtaining restful or enough sleep.

In addition, certain drugs may also cause reductions in REM sleep as a side effect and the present invention may be used to correct those types of sleeping disorders as well. The present invention would also be of benefit in the treatment of syndromes such as fibromyalgia which are manifested by non-resotrative sleep and muscle pain or sleep apnoea which is associated with respiratory disturbances during sleep. It will be clear to one skilled in the art that the present invention is not limited to just sleep disorders and sleep disturbances, but is applicable to a wide variety of conditions which result from a diminished quality of sleep.

This compounds of formula (I) may be used alone or in combination with other agents which are known to be beneficial in altering circadian rhythms or in the enhancement of sleep efficiency. For example, the compounds of formula (I) may be administered in conjunction with other compounds which are known in the art to be useful for suppressing or stimulating melatonin production including melatonergic agents, nonadrenergic and serotonergic re-uptakes blockers, alpha-1-noradrenergic agonists, monamine oxidase inhibitors, beta-adrenergic blockers and benzodiazepines, such as atenolol; or with other compounds which are known in the art to be useful for stimulating melatonin production including tricyclic antidepressants and alpha-2-adrenergic antagonists; or with melatonin precursors such as tryptophan, 5-hydroxytryptophan, serotonin and N-acetylserotonin; as well as melatonin analogues, melatonin agonists and melatonin antagonists. In addition, the compounds of formula (I) may be administered in conjunction with other compounds which are known in the art to be useful for enhancing sleep quality and preventing and treating sleep disorders and sleep disturbances, including e.g., sedatives, hypnotics, anxiolytics, antipsychotics, antianxiety agents, minor tranquilizers, melatonin agonists and antagonists, melatonin, melatonergic agents, benzodiazepines, barbituates, 5HT-2 antagonists, and the like, such as adinazolam, aliobarbital, alonimid, alprazolam, amitriptyline, amobarbital, amoxapine, bentazepam, benzoctamine, brotizolam, bupropion, busprione, butabarbital, butalbital, capuride, carbocloral, chloral betaine, chloral hydrate, chlordiazepoxide, clomipramine, cloperidone, clorazepate, clorethate, clozapine, cyprazepam, desipramine, dexclamol, diazepam, dichloralphenazone, divalproex, diphenhydramine, doxepin, estazolam, ethchlorvynol, etomidate, fenobam, flunitrazepam, flurazepam, fluvoxamine, fluoxetine, fosazepam, glutethimide, halazepam, hydroxyzine, imipramine, lithium, lorazepam, lormetazepam, maprotiline, mecloqualone, melatonin, mephobarbitoal, meprobamate, mthaqualone, midaflur, midazolam, nefazodone, nnisobamate, nitrazepam, nortripyline, oxazepam, paraldehyde, paroxetine, pentobarbital, periapine, perphenazine, phenelzine, phenobarbital, prazepam, promethiazine, propofol, protriptyline, quazepam, reclazepam, roletamide, secobarbital, sertraline, suproclone, temazepam, thioridazine, tracazolate, tranylcypromaine, trazodone, triazolam, trepipam, tricetamide, triclofos, trifluoperazine, trimetozine, trimipramine, uldazepam, valproate, venlafaxine, zaleplon, zolazepam, zolpidem, and salts thereof, and combinations thereof, and the like.

The compounds of formula (I) may be administered in conjunction with the use of physical methods such as with light therapy or electrical stimulation. In particular, the compounds of formula (I) may be administered in conjunction with scheduling bright light administration, ordinary-intensity light exposure, or exposure to dim-light or darkness (or even sleep). In one embodiment of the present invention, the compound of formula (I) is administered accompanied by having an individual wear dark or red goggles at the time of administration to provide additive effects of the treatment plus darkness. In another embodiment of the present invention, the individual wears dark goggles at times other than the time of administration of the compound of formula (I) to avoid the ocurrence of an external zeitgeber with respect to the phase shift resulting from the compound of formula (I). Similarly, bright light exposure can be used in conjunction with administration of a compound of formula (I).

Accordingly, the present invention further includes within its scope the use of a compoundof formula (I), alone or in combination with other agents, for altering circadian rhythms or for the prevention or treatment of sleep disorders and sleep disturbances in a mammal.

As used herein the term "mammals" includes animals of economic importances such as bovine, ovine, and porcine animals, especially those that produce meat, as well as domestic animals, sports animals, zoo animals, and humans, the latter being preferred.

It will be appreciated that when using any combination described herein, both the compound of formula (I) and the other active agent(s) will be administered to a patient, within a reasonable period of time. The compounds may be in the same pharmaceutically acceptable carrier and therefore administered simultaneously. They may be in separate pharmaceutical carriers such as conventional oral dosage forms which are taken simultaneously. The term "combination" also refers to the case where the compounds are provided in separate dosage forms and are administered sequentially. Therefore, by way of example, one active compound may be administered as a tablet and then, within a reasonable period of time, the second active component may be administered either as an oral dosage form such as a tablet or a fast-dissolving oral dosage form. By a "fast dissolving oral formulation" is meant, an oral delivery from which when placed on the tongue of a patient, dissolves within about 10 seconds.

By "reasonable period of time" is meant a time period that is not in excess of about b 1hour. That is, for example, if the first active component is provided as a tablet, then within one hour, the second active component should be administered, either in the same type of dosage form, or another dosage form which provides effective delivery of the medicament.

The excellent pharmacological profile of the compounds of the present invention offers the opportunity for their use in therapy at low doses thereby minimising the risk of unwanted side effects.

In the treatment of the conditions associated with an excess of tackykins, a suitable dosage level is about 0.001 to 50 mg/kg per day, in particular, about 0.01 to about 25 mg/kg, such as from about 0.05 to about 10 mg/kg per day.

For example, in the treatment of conditions involving the neurotransmission of pain sensations, a suitable dosage level is about 0.001 to 25 mg/kg per day, preferably about 0.005 to 10 mg/kg per day, and especially about 0.005 to 5 mg/kg per day. The compounds may be administered on a regimen of 1 to 4 times per day, preferably once or twice per day.

In the treatment of emesis using an injectable formulation, a suitable dosage level is about 0.001 to 10 mg/kg per day. The compounds may be administered on a regimen of 1 to 4 times per day, preferably once or twice per day.

It will be appreciated that the amount of a compound of formula (I) required for use in any treatment will vary not only with the particular compounds or composition selected but also with the route of administration, the nature of the condition being treated, and the age and condition of the patient and will ultimately be at the discretion of the attendant physician.

According to a general process (A.1), the compounds according to the invention in which X is —CH$_2$—and Y is —CH$_2$ or —CH$_2$CH$_2$—, may be prepared by the reduction of a corresponding compound of formula (I) in which the broken line represents a double bond, hereinafter referred to as a compound of formula (IA)

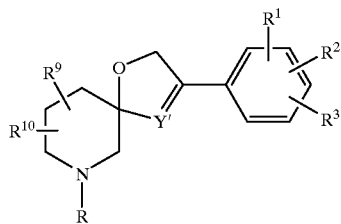

(IIA)

wherein Y' is —CH= or —CH$_2$CH=

Suitable reducing conditions include: catalytic hydrogenation using a metal catalyst such as palladium or platinum or hydroxides or oxides thereof, preferably in a suitable solvent such as alcohol, e.g. methanol or ethanol, or an ester, e.g. ethyl acetate, or an organic acid e.g. acetic acid, or a mixture thereof; or reduction using trifluoroacetic acid and triethylsilane.

Similarly, according to a general process (A.2), compounds of formula (I), in which X is —CH$_2$— and Y is —CH$_2$CH$_2$—, may be prepared by the reduction of a compound of formula (IIB)

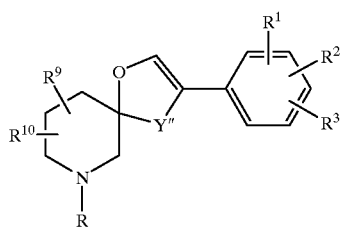

(IIB)

wherein Y" is —CH$_2$—or —CH$_2$CH$_2$—, using the reaction conditions described in process (A.1) above.

According to another general process (B), compounds of formula (I), in which X is —CH$_2$— and Y is —CH= or—CH$_2$CH= and the broken line is a double bond (i.e. compounds of formula (IIA) may be prepared by the reaction of a compound of formula (III)

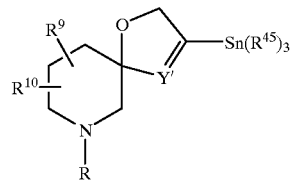

(III)

wherein Y' is —CH= or —CH$_2$CH= and each R$^{45}$ is a C$_1$-alkyl group, preferably methyl or n-butyl groups, with a compound of formula (IV)

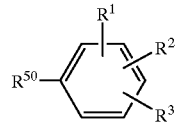

(IV)

wherein R$^{50}$ is a leaving group such as triflate (OSO$_2$CF$_3$) or a halogen atom for example, chlorine, bromine or iodine, especially triflate, bromine or iodine.

The reaction is conveniently effected in the presence of lithium chloride and a transition metal catalyst such as tetrakis(triphenylphosphine) palladium (O). Suitable solvents for the reaction include aromatic hydrocarbon, for example, toluene, polar aprotic solvents, for example, dimethylformamide or ethers, for example, dioxan, the reaction being effected at a temperature between 80° C. and the reflux temperature of the solvent.

According to another general process (C), compounds of formula (I) may be prepared from a compound of formula (V)

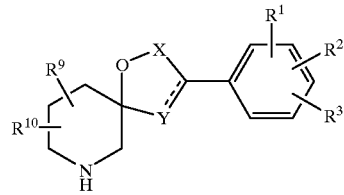

(V)

wherein R$^1$, R$^2$, R$^3$, X, Y and the broken line are as defined in relation to formula (I) by reaction with a compound of formula (VI):

LG—R$^z$  (VI)

where R$^z$ is a group of the formula R as defined in relation to formula (I) or a precursor therefor and LG is a leaving group such as an alkyl- or arylsulphonyloxy group (e.g. mesylate or tosylate) or a halogen atom (e.g. bromine, chlorine or iodine); and, if R$^z$ is a precursor group, converting it to a group R (in which process any reactive group may be protected and thereafter deprotected if desired).

This reaction may be performed in conventional manner, for example in an organic solvent such as dimethylformamide in the presence of an acid acceptor such as potassium carbonate.

Suitable alternative methods for introducing the group R$^6$ are described, for instance, in International Patent Specification No. WO 95/18124.

According to another process (D), compounds of formula (I) may be prepared by further interconversion processes from other compounds of formula (I) using suitable procedures. In particular, processes may be used to vary the group R. For example, compounds of formula (I) herein R is a $C_1$-alkyl group substituted by the group Ar may be prepared from the corresponding compounds of formula (I) wherein R is a $C_{1-4}$ alkyl group substituted by the group Ar and further substituted by $R^4$ and $R^5$ where $R^4$ and $R^5$ together represent an oxo group, by reduction using, for example, borane or a borohydride such as sodium cyanoborohydride.

According to another general process (E), compounds of formula (I) wherein $R^3$ is a terazol-1-yl group may be prepared by reaction of an intermediate of formula (VII)

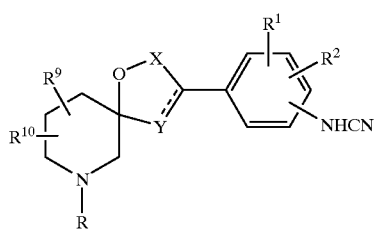

(VII)

with ammonium chloride and sodium azide at elevated temperature, conveniently in a solvent such as dimethylformamide.

According to another general process (F), compounds of formula (I) may be prepared by a coupling reaction between a compound of formula (VIII) and (IX)

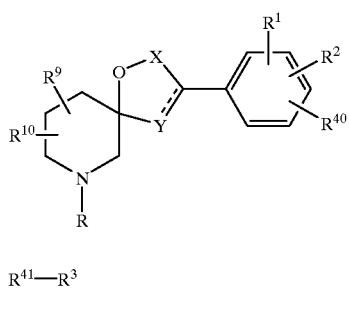

(VIII)

$R^{41}-R^3$ (IX)

wherein one of $R^{40}$ and $R^{41}$ is $B(OH)_3$ or $Sn(alkyl)_3$ or a derivative thereof, and the other is a leaving group such as a halogen atom e.g. bromine or iodine, or $-OSO_2CF_3$. Where one of $R^{40}$ and $R^{41}$ is $B(OH)_2$, the reaction is conveniently effected in the presence of a palladium (O) catalyst such as tetrakis(triphenylphosphine)palladium (O) in a suitable solvent such as an ether, for example, dimethoxyethane at an elevated temperature. Where one of $R^{40}$ and $R^{41}$ is $Sn(alkyl)_3$, the reaction is conveniently effected in the presence of palladium (II) catalyst such as bis(triphenylphosphine) palladium (H) chloride, in a suitable solvent such as an aromatic hydrocarbon, for example, toluene, at an elevated temperature.

According to another general process (G), compounds of formula (I) may be prepared from a compound of formula (X)

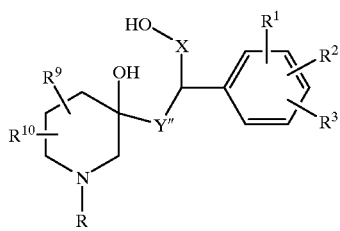

(X)

wherein Y" is $-CH_3-$or $-CH_2CH_2-$, by an acid catalysed intramolecular cyclisation reaction or by a dehydration reaction.

Suitable acids of use in the reaction include mineral acids such as hydrochloric acid. The reaction is conveniently effected in a suitable organic solvent, such as an alcohol, e.g. methanol, at an elevated temperature, for example, at the reflux temperature of the chosen solvent.

Suitable dehydrating reagents of use in the reaction include, for example, methanesulphonyl chloride or benzensulphonyl chloride in pyidine or triethylamine. The reaction is conveniently effected at a temperature between 0° C. and 100° C., preferably at between room temperature and 80° C. using a suitable organic solvent such as dichloromethane, where necessary.

Intermediates of formula (X) are particularly preferred for controlling the stereochemistry of the 3-position in compounds of formula (I), especially where the 3(R) epimer is desired.

According to another general process (H), compounds of formula (I) may be prepared by the reaction of a compound of formula (XX)

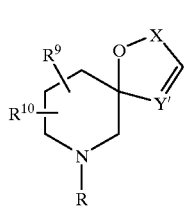

(XX)

with a compound of formula (IV), under the conditions of a reductive Heck reaction using a palladium catalyst such as palladium acetate with, for example, dimethylformamide and tetrabutylammonium chloride, and a reducing agent, preferably formic acid or a salt thereof, such as potassium formate.

According to another general process (J), compounds of formula (I) in which $R^1$ is $C_{1-6}$-alkoxy, fluoro$C_{1-6}$alkenoxy, $C_{3-7}$cycloalkoxy, $C_{3-7}$cycloalkyl$C_{1-1}$alkoxy or benzyloxy, may be prepared by the interconversion of a compound of formula (I) wherein R' is hydroxy, hereinafter referred to as formula (XXVI)

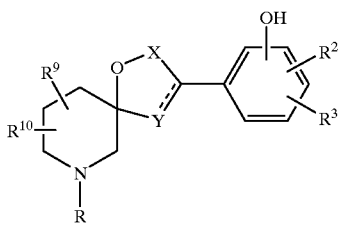

(XXVI)

by reaction with an appropriate alkyl—, fluoroalkyl—, alkenyl—, cycloalkyl—, cycloalkylalkyl— or aralkyl-halide, especially the iodide, in the presence of a base.

Suitable bases include alkali metal hydrides, such as sodium hydride, in a suitable solvent such as dimethylformamide. The reaction is conveniently effected at about room temperature.

According to a further general process (K), compounds of formula (I) in which Y is —CH═ or a —CH$_2$CH═ (i.e. a compound of formula (HA), above), may be prepared by the dehydration of a compound of formula (XXVII)

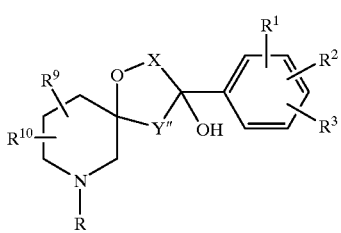

(XXVII)

using an acid such as trifluoroacetic acid. The reaction is conveniently effected at a temperature between 0° C. and room temperature, using a suitable organic solvent such as dichloromethane.

According to another general process (L), compounds of formula (I) may be prepared from a compound of formula (XXVIII)

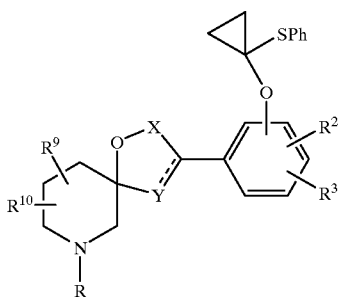

(XXVIII)

by reaction with lithium naphthalenide in tetrahydrofuran. The reaction is preferably effected at reduced temperature, for example at about −78° C.

Further details of suitable procedures will be found in the accompanying Examples.

Compounds of formula (IIB) may be prepared using the method of general process (K) described above.

Intermediates of formula (V) may be prepared in a similar manner to the methods of the processes described above, preferably with an amino protecting group on any unprotected nitrogen atom. Suitable amino protecting groups include alkoxycarbonyl groups such as tert-butoxycarbonyl and tricholorethoxycarbonyl, aralkyloxycarbonyl groups such as benzyloxycarbonyl, or aralkyl groups such as benyl. Removal of the protecting group is effected by conventional procedures thus, for example, tert-butoxycarbonyl groups may be removed under acidic conditions using, for example, trifluoroacetic acid; tert-butoxycarbonyl groups, together with benzyloxycarbonly and benzyl groups, may also be removed by hydrogenolysis in the presence of a catalyst, for example, palladium; and trichloroethoxycarbonyl groups may be removed with zinc dust.

Compounds of formula (III) may be prepared from a compound of formula (XI)

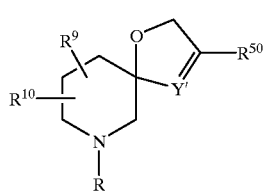

(XI)

wherein $R^{50}$ is as previously defined (and is preferably a triflate group or a bromine or iodine atom), by reaction with a compound of the formula $(R^{45})_3Sn-Sn(R^{45})_3$, for example, hexamethyl distannane. The reaction is conveniently effected in the presence of a base, for example, lithium carbonate, and a catalyst such as triphenylphosphine palladium(O). Suitable solvents for the reaction include ethers such as tetrahydrofuran, the reaction being effected at a temperature between room temperature and 100° C., for example, at about 60° C.

Compounds of formula (XI) may be prepared from a compound of formula (XII)

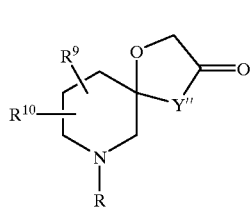

(XII)

by enolisation of the ketone in the presence of a base, for example, sodium hexamethyldisilazide, followed by reaction with a reagent capable of introducing a suitable leaving group, for instance, where $R^{50}$ is —OSO$_2$CF$_3$, using 2-[N, N-bis(trifluoromthylsulphonyl)amino]-5-chloropyridine or triflic anhydride. The reaction is conveniently effected in a suitable solvent such as an ether, for example, tetrahydrofuran at a reduced temperature, for instance, −80° C.

Compounds of formula (XII) may be prepared from a compound of formula (XIII) by the following reaction sequence (Scheme A) or by methods analogous thereto (with the proviso that $R^9$ and $R^{10}$ are not oxo):

Scheme A

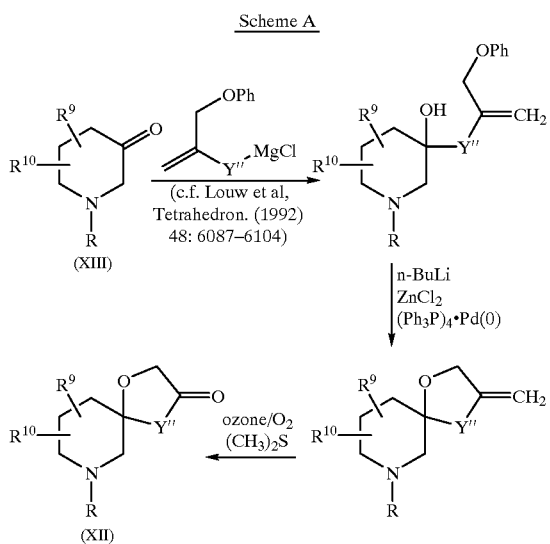

Compounds of formula (III), wherein Y' is —CH=, may also be prepared from a compound of formula (XIII) by the following reaction sequence (Scheme B) or by methods analogous thereto (with the proviso that $R^9$ and $R^{10}$ are not oxo):

Scheme B

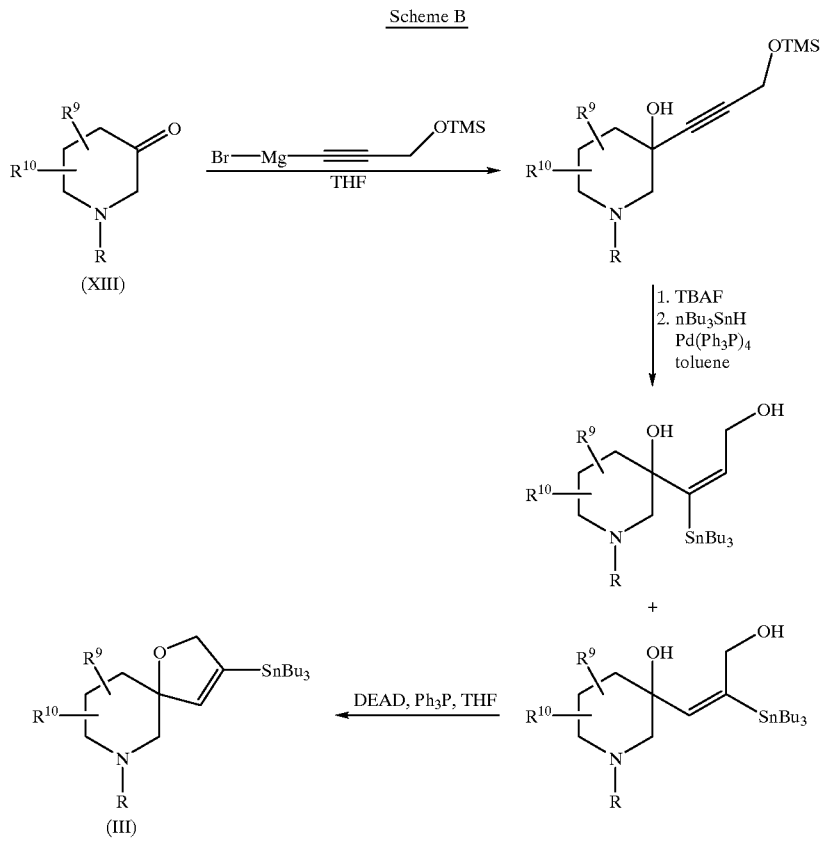

In another preferred embodiment of the aforementioned processes, R is a benzyl group. The reduction reaction described as process (A) above for the preparation of compounds of formula (I) may conveniently replace the benzyl group with a hydrogen atom (i.e. forming a compound of formula (V)).

Compounds of formula (IV) in which $R^3$ is an N-linked heterocyclic group may be prepared by conventional methodology, for example, from a compound of formula (XIV)

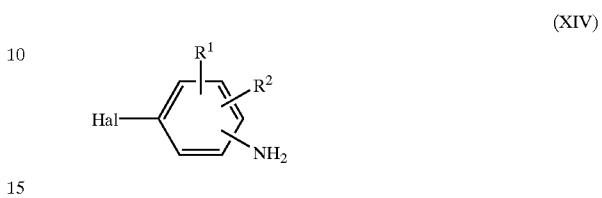

(XIV)

by reaction with a suitable anhydride of the formula $(R^{60}CO)_2O$, where $R^{60}$ is hydrogen or a desired substituent for the heterocycle, followed by reaction with triphenylphosphine in carbon tetrachloride, followed by the further step of (i) reaction with an azide such as sodium azide to effect the formation of a tetrazole ring; or (ii) reaction with hydrazine hydrate to effect the formation of a 1,2,4-triazole ring; or (iii) reaction with aminoacetaldehyde diethyl acetal to effect the formation of an imidazole ring.

Components of formula (XIV) may be prepared from the corresponding nitro compound by reduction using, for example, iron powder, or Raney nickel in a conventional manner.

The compounds of formula (XIV) or their nitro precursors are either known compounds or may be prepared using conventional methodology.

Compounds of formula (VII) may be prepared by reacting a compound of formula (XV)

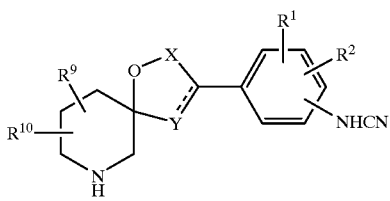

(XV)

with any suitable reagent for completing the R moiety as described in the preceding processes.

Compounds of formula (VII) may also be prepared by reaction of a compound of formula (III) with a compound of formula (XVI)

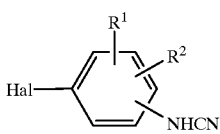

(XVI)

according to the method described in process (B), above.

Intermediates of formula (X) wherein Y" is —CH$_2$CH$_3$— may be prepared by the reduction of a compound of formula (XVII)

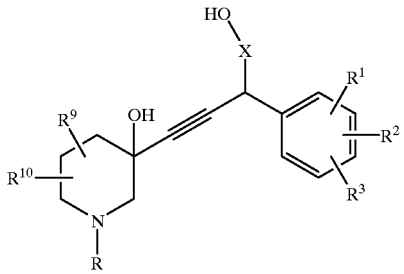

(XVII)

or a protected derivative thereof, using conventional methodology, for instance, by catalytic hydrogenation using a metal catalyst such as palladium or platinum or oxides thereof, preferably in a solvent such as an alcohol, e.g. ethanol, or an ester, e.g. ethyl acetate.

A particularly preferred hydroxyl protecting group is the trimethylsilyl group.

Compounds of formula (XVII) may be prepared by the reaction of a compound of formula (XIII) with a compound of formulae (XVIII)

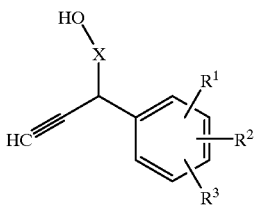

(XVIII)

or a protected derivative thereof, by lithiation using n-butyl lithium followed by quenching with, for example, sodium dihydrogen orthophosphate. The reaction is conveniently effected in a solvent such as an ether, e.g. tetrahydrofuran, at a reduced temperature, for example, at −78° C.

Compounds of formula (XIII) may be prepared by methods described in European Patent Specification No. 0 577 394-A, or by analogous methods.

Compounds of formula (XVIII) are known compounds (see *Chemische Berichte,* (1988) 121, 1315–1320) or may be prepared by methods analogous to those described therein.

Compounds of formula (IX) and (XVI) are known compounds or may be prepared by conventional methods or using techniques analogous to those taught herein.

In an alternative method, compounds of formula (X) may be prepared by the reduction of a compound of formula (XXI)

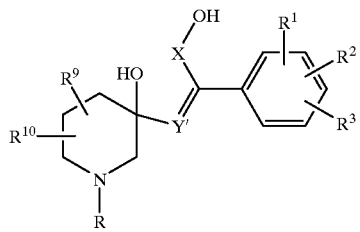

(XXI)

using, for example, catalytic hydrogenation in the presence of a metal catalyst such as palladium or platinum or hydroxides or oxides thereof, preferably in a suitable solvent such as an alcohol, e.g. methanol, an ester, e.g. ethyl acetate, or an organic acid, e.g. acetic acid, or a mixture thereof.

Compounds of formula (XXI) wherein Y' is —CH═ may be prepared from a compound of formula (XXII)

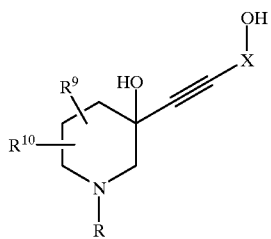

(XXII)

by reaction with a compound of formula (IV) using reductive Heck conditions as described in A. Arcadi et al, *Tetrahedron,* 1988, 44, 481.

Compounds of formula (XXII) may be prepared from compounds of formula (XIII) and, for example, a Grignard reagent prepared from O-trimethylsilylpropargyl alcohol using conventional methodology, followed by removal of the hydroxy protecting group.

According to another method, compounds of formula (X) may be prepared from a compound of formula (XXIII)

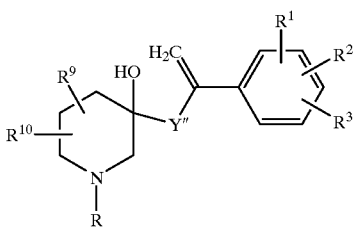

(XXIII)

by reaction with borane in tetrahydrofuran, followed by an oxidative work-up using, for example, hydrogen peroxide and sodium hydroxide.

Compounds of formula (XXIII) may be prepared from a compound of formula (XIII) and, for example, a Grigard reagent prepared from a 2-aryl-3-bromo-1-propene using conventional methodology.

Compounds of formula (XX) may be prepared, for example, by the conversion of a stannane of formula (III) to the corresponding iodide by treatment with iodine at reduced temperature, for example, at about −78° C., in a suitable solvent such as dichloromethane. The iodine may then be displaced to give the compound of formula (XX) by treatment with, for example, α, α'-azo-isobutyronitrile and tributyronitrile and tributyltin hydride in a suitable solvent, for example, toluene, at an elevated temperature, for example, at about 100° C.

Alternatively, compounds of formula (XX) may be prepared by the cyclisation of a compound of formula (XXIV)

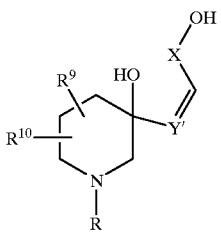

(XXIV)

using the dehydrating conditions described above for general process (G) or using triphenylphosphine and diethylazodiacarboxylate in a suitable solvent such as tetrahydrofuran.

Compounds of formula (XXIV) wherein Y' is —CH═ may be prepared by the partial reduction of an acetylene compound of formula (XXII). The reaction is conveniently effected by catalytic hydrogenation using a metal catalyst such as palladium on calcium carbonate in the presence of a lead poison (e.g. Lindlar catalyst). Other suitable methods will be readily apparent to a person of ordinary skill in the art.

Further useful methodology for the preparation of compounds in which Ar is a heterocyclic group is described, for example, in International Patent Specification No. WO 95/18124.

Compounds of formula (XXVI) may be prepared from the appropriate phenolic precursor for a protected (e.g. benzyloxy) derivative thereof) using for example, the methods of precursor (A), (B), or (C).

Compounds of formula (XXVII) may be prepared by the reaction of a compound of formula (XII) with Grignard reagent prepared from a compound of formula (IV), preferably using magnesium and a bromide of formula (IV). the coupling reaction is conveniently effected at reduced temperature, for example at about 0° C., using a suitable solvent such as an ether, for example, diethyl ether.

Compounds of formula (XXVIII) may be prepared from a compound of formula (XXVI) by reaction with (1-iodocycloprop-1-yl)phenylsulfide.

It will be appreciated that compounds of the formula (I) wherein Ar contains an ═O or ═S substituent can exist in tautomeric forms. All such tautomeric forms and mixtures thereof are included within this invention. Most aptly the ═O or ═S substituent in Ar is the ═O substituent.

Where they are not commercially available, the intermediates of formula (VI) above may be prepared by the procedures described in the accompanying Examples or by alternative procedures which will be readily apparent to one skilled in the art.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wuts, *Protective Groups in Organic Synthesis*, John Wiley & Sons, 1991. The protecting groups may be removed at a convenient subsequent stage using methods known from the art.

The exemplified compounds of this invention were tested by the methods set out at pages 36 to 39 of International Patent Specification No. WO 93/01165. The compounds were found to be active with $IC_{50}$ at the $NK_1$ receptor of less than 1 μM on said test method.

For the avoidance of doubt, the nomenclature adhered to throughout this specification follows the general principles illustrated below.

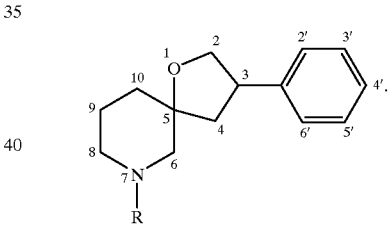

As used herein, (±)-(3R*,5R*) refers to a racemic mixture of (3R,5R) and (3S,5S).

The following non-limiting Examples serve to illustrate the preparation of compounds of the present invention:

DESCRIPTION 1

1-Benzyl-3-(3-hydroxy-1-propyn-1-yl)piperidin-3-ol

O-Trimethylsilylpropargyl alcohol (15.4 ml, 100 mmol) was added slowly at 0 to 5° C. to a cooled (0° C.) solution of ethylmagnesium bromide (1 M in tetrahydrofuran, 100 ml, 100 mmmol) in tetrahydrofuran. The reaction mixture was stirred at 0° C. for 15 minutes and then allowed to warm to room temperature over 30 minutes (exotherm and gas evolution observed), before recooling to 0° C. To this was added a solution of 1-benzyl-3-piperidone (15.16 g, 80.1 mmol) in tetrahydrofuran (30 ml), keeping the temperature below 5° C. The reaction mixture was stirred at room temperature overnight, quenched by addition of water/ saturated aqueous ammonium chloride (50 ml/50 ml) and extracted with ethyl acatate (2×100 ml). The organic phases were washed with brine (100 ml), combined, dried (MgSO₄) and evaporated to an amber oil (25.55 g). This oil was dissolved in tetrahydrofuran (50 ml), the solution cooled to 0° C. and treated with a solution of tetrabutylammonium fluoride (1.1 M in tetrahydrofuran, 100 ml, 110 mmol). After stirring at room temperature for 20 minutes the solution was concentrated in vacuo, diluted with water (250 ml) and extracted with ethyl acatate (2×100 ml). The extracts were washed with brine (100 ml), combined, dried (MgSO$_4$) and evaporated to give the title product as an oil (18.65 g, 95%); m/z (ES$^+$) 246 ([M+H]$^+$).

DESCRIPTION 2

1-Benzyl-3-(3-hydroxy-2-tributylstannyl-1-propen-1-yl)piperidin-3-ol

Tributyltin hydride (7.8 ml, 29 mmol) was added dropwise to a degassed solution of 1-benzyl-3-(3-hydroxy-1-propyn-1-yl)piperidin-3-ol (Desc. 1; 5.91 g, 24.1 mmol) and tetrakis(trisphenylphosphine)palladium(0) (0.52 g, 0.45 mmol) in toluene (100 ml) at −5° C. The reaction mixture was stirred at −5° C. for 2 hours, allowed to warm up and concentrated in vacuo to afford an approximately 2.5:1 mixture of the title compound and isomeric 1-benzyl-3-(3-hydroxy-1-tributylstannyl-1-propen-1-yl)piperidin-3-ol. The mixture was purified by flash chromatography, eluting with ethyl acetate/hexane (1:2), to give the title compound (8.82 g, 68%; $\delta_H$(250 MHz, CDCl$_3$) 0.88 (15 H, m), 1.24–1.53 (14H, m), 1.78 (2H, m), 1.98 (1H, m), 2.11 (1H, d, J 11.1Hz), 2.69–2.80 (2H, m), 3.51 (1H, d, J. 13.2Hz, NCH$_A$CH$_B$Ph), 3.57 (1H, d, J 13.2Hz, NCH$_A$CH$_B$Ph), 4.44 (2H, br s, CH$_2$OH), 5.38 (1H, br s, CH=C), 7.26–7.34 (5H, m ArH).

DESCRIPTION 3

7-Benzyl-3-tributylstannyl-1-oxa-7-azaspiro[4.5]dec-3-ene

Diethyl azodicaboxylate (3.1 ml, 19.7 mmol) was added dropwise to a solution of 1-benzyl-3-(3-hydroxy-2-tributylstannyl-1-propen-1-yl)piperidin-3-ol (Desc. 2; 8.72 g, 16.26 mmol) and triphenylphosphine (5.12 g, 19.5 mmol) in tetrahydrofuran (100 ml) at −5° C. The cooling bath was removed and the reaction mixture stirred for 45 minutes. The solvent was evaporated, the residue dissolved in acetonitrile (300 ml) and extracted with hexane (3×150 ml). The combined hexane extracts were evaporated and the residue chromatographed on silica, eluting with ethyl acetate/hexane (1:9 then 1:4), to afford the title compound as a colourless oil (5.00 g, 59%); $\delta_H$ (250 MHz, CDCl$_3$) 0.87–0.96 (15 H, m), 1.25–1.35 (6H, m), 1.45–1.60 (11H, m), 1.79 (1H, m), 2.29–2.48 (4H, m), 3.48 (1H, d, J 13.3Hz, NCH$_Z$CH$_B$Ph), 3.59 (1H, d, J 13.3Hz, NCH$_A$CH$_B$Ph), 4.67 (2H, m, 2-CH$_2$), 6.03 (1H, br s, 4-CH=), 7.22–7.30 (5H, m ArH).

DESCRIPTION 4

2-Bromo-4-(5-trifluoromethyl-1H-tetrazol-1-yl)anisole (a) 4-amino-2-bromoanisole A mixture 2-bromo-4-nitroanisole (15 g, 64.6 mmol) and iron powder (27.3 g, 0.49 mol) in water (100 ml) and glacial acetic acid (25 ml) was stirred at reflux for 2 hours. The mixture was allowed to cool to ambient temperature and filtered through a pad of Hyflo™ (washed with 25% acetic acid/water). The filtrate was extracted with ethyl acetate (2×250 ml) and the organic layer was dried over sodium sulphate. Removal of the solvent in vacuo left an oil which was chromatographed on silica eluting with 40% ethyl acetate/hexane to give the title compound as a brown solid (10.32 g, 79%); m/z (ES$^+$) 202 ([M+H]$^+$).

(b) 2-Bromo-4-(trifluoroacetamido)anisole

4-Amino-2-bromoanisole (5 g, 24.7 mmol) was dissolved in dichloromethane (50 ml) containing triethylamine (3.44 ml, 24.7 mmol). The solution was cooled to 0° C. and trifluoracetic anhydride (3.5 ml, 24.7 mmol) was added slowly. The reaction was stirred at ambient temperature for 2 hours, diluted with dichloromethane (200 ml) and washed with water (2×200 ml). The organic layer was dried over sodium sulphate and the solvent was removed in vacuo leaving an oil. Chromatography on silica eluting with 15–25% ethyl acetate/hexane gave the title compound as white solid (4.4 g); $\delta_H$ (250 MHz, CDCl$_3$) 7.79 (1H, d, J 2.6Hz, 3-H), 7.58 (1H, dd, J 8.9, 2.6 Hz, 5-H), 6.90 (1H, d J 8.9Hz, 6-H), 3.90 (3H, s, ArOCH$_3$).

(c) 2-Bromo-4-(5-trifluoromethyl-1H-tetrazol-1-yl)anisole

2-Bromo-4-(trifluoroacetamido)anisole (4.3 g, 14.4 mmol) was suspended in carbon tetrachloride (80 ml). The suspension was heated to 80° C. and triphenylphosphine (4.54 g, 17.3 mmol) was added in portions over 4 hours. The reaction was stirred at 80° C. for 16 hours. The solvent was removed in vacuo and hexane (100 ml) was added to the residue and heated to reflux temperature. The suspension was allowed to cool to ambient temperature and filtered (triphenylphosphine oxide). The solvent was removed from the filtrate in vacuo leaving an oil (4.6 g). The oil in N,N-dimethylformamide (20 ml) was added to a suspension of sodium azide (1.24 g, 19.1 mmol) in N,N-dimethylformamide (20 ml) at ambient temperature. The mixture was stirred for 2 hours and poured into water (200 ml). The mixture was extracted with ethyl acetate (2×200 ml) and the combined organics were washed with water (200 ml), dried over sodium sulphate and the solvent was removed in vacuo leaving a yellow oil. Chromatography on silica eluting with 25% ethyl acetate/hexane gave the title compound as a clear oil (4.9 g); 67 $_H$ (250 MHz, CDCl$_3$) 7.72 (1H, d J 2.6 Hz, 3-H), 7.44 (1H, dd, J 8.9, 2.6Hz, 5-H), 7.08 (1H, d, J8.9 Hz, 6-H), 4.02 (3H, s, ArOCH$_3$).

DESCRIPTION 5

2-Bromo-4-(1H-tetrazol-1-yl)anisole

4-Amino-2-bromoanisole (Desc. 4(a); 4.7 g) was dissolved in triethylorthoformate (50 ml), trifluoroacetic acid (1.8 ml) was added and the mixture heated at reflux for 48 hours. The solvent was removed in vacuo to afford a brown solid. Sodium azide (2.25 g) and acetic acid (25 ml) were added and the mixture heated at reflux for 6 hours. The product was purified on flash silica eluting with dichloromethane containing increasing proportions of methanol (0.25%, 0.5 and 0.75%) to give the title compound as a brown solid (3.98 g, 67% yield); $\delta_H$ (250MHz, DMSO-d$_6$) 4.07 (3H, s, ArOCH$_3$), 7.50 (1H, d, J 9Hz, 6-H), 8.03 (1H, dd, J 3, 9Hz, 5-H), 8.32 (1H, d, J 3Hz, 3-H), 10.16 (1H, s, 5'-H).

DESCRIPTION 6

2-Bromo4-(4'-pyridyl)anisole a) 4-(4'-Pyridyl)anisole

4-Methoxybenzene boronic acid (2 g, 13.15 mmol) and 4-bromo-pyridine hydrochloride were suspended in dimethyoxyethane (50 ml). A 2M solution of sodium carbonate (30 ml) was added followed by diphenylphosphinobutanepalladium(II) chloride (100 mg). The mixture was stirred at 85° C. for 1.5 hours under an atmosphere of nitrogen. The reaction mixture was allowed to cool to ambient temperature, was diluted with ethyl acetate (150 ml) and washed with water (2×50 ml). The aqueous layer was extracted with ethyl acetate (2×100 ml) and the combined organic layers were dried over sodium sulphate. Removal of the solvent in vacuo gave an off white solid which was chromatographed on silica gel in 70–100% ethyl acetate/hexane as eluent. The title compound was obtained as a white solid (1.95, 80%); $\delta_H$ (250MHz, CDCl$_3$) 8.62–8.60 (2H, dd, J 6.2, 1.6Hz), 7.03–7.57 (2H, dd, J 9.0, 2.2Hz), 7.50–7.47 (2H, dd, J 6.2, 1.6Hz), 7.04—6.98 (2H, dd, J 9.0, 2.2Hz), 3.87 (3H, s); m/z (ES$^+$) 186 ([M+Hυ$^+$).

b) 2-Bromo-4-(4'-pyridyl)anisole 4-(4'-Pyridyl)anisole (1 g, 5.4 mmol) was dissolved in acetic acid (6 ml) with stirring. Iron powder (30 mg, 0.54 mmol) was added. Bromine (0.33 ml, 6.33 mmol) in acetic acid (4 ml) was added dropwise over 5 min. at ambient temperature. The reaction was then stirred at 60° C. for one hour. Bromine (0.16 ml, 3.1 mmol) in acetic acid (2 ml) was added and the solution was stirred at 60° C. for a further 1.5 hours and then allowed to cool to ambient temperature. Water (25 ml) was added and excess bromine was destroyed by adding solid sodium bisulphate until the colour disappeared. Solid sodium carbonate was added to basify the solution which was then extracted with ethyl acetate (2×30 ml). The combined organic layers were dried over sodium sulphate and removal of the solvent in vacuo gave an oil which was chromatographed on silica in diethyl ether as eluent giving the title compound as a white solid (772 mg, 54%); $\delta_H$ (250 MHz, CDCl$_3$) 8.64—8.62 (2H, dd, J 6.2, 1.7Hz), 7.85 (1H, d J 2.2Hz), 7.61—7.56 (1H, dd, J 8.6, 2.2Hz), 7.48—7.46 (2H, dd, J 6.2, 1.7Hz), 7.02—6.99 (1H, d, J 8.6Hz); m/z (ES$^+$) 266/264 ([M+H]$^+$).

DESCRIPTION 7
2-Bromo-4-trifluoromethoxyanisole (a) 2-Bromo-4-trifluoromethoxyphenol To a cooled (0° C.) solution of 4-trifluoromethoxyphenol (35.6 g, 0.2 mol) in chloroform (280 ml) was added dropwise a solution of bromine (32 g, 0.2 mol) in chloroform (50 ml). The solution was stirred at 0° C. for 1 hour and at room temperature for 2 hours. Dichloromethane (200 ml) and water (400 ml) were added and the organic phase was washed with water (400 ml), brine (200 ml) and dried (MgSO$_4$). The solvent was removed and the residue purified by distillation at reduced pressure to give the title compound; $\delta_H$ (250MHz, CDCl$_3$) 7.38 (1H, d, J 2.1Hz, 3-H), 7.13 (1H, dd, J 9.1, 2.1Hz, 5-H), 7.03 (1H, d, J 9.1Hz, 6-H), 5.53 (1H, s, ArOH).

(b) 2-Bromo-4-trifluoromethoxyanisole

To a solution of 2-bromo-4-trifluoromethoxyphenol (7.2 g) and potassium carbonate (11.6 g, 0.084 mol) in dimethylformamide (60 ml) was added methyl iodide (14.94 ml, 0.24 mol). The solution was stirred for 15 hours at room temperature under nitrogen whereupon water (400 ml) and diethyl ether (200 ml) were added. The organic phase was washed with water (4×200 ml), saturated NaHCO3 (2×200 ml), brine (200 ml), and the solvent removed in vacuo. The residue was purified by chromatography on silica gel eluting with ethyl acetate in hexane (0–2%) to give the title compound; $\delta_H$ (250 MHz, CDCl$_3$) 7.45 (1H, d, J 2.8Hz, 3-H), 7.16 (1H, dd, J 9.0, 2.8Hz, 5-H), 6.88 (1H, d, J 9.0Hz, 6-H), 3.90 (3H, s, ArOCH$_3$).

DESCRIPTION 8
2-Bromo-4-(3-trifluoromethyl-4H-1,2,4-triazol-4-yl)anisole

2-Bromo-4-(trifluoroacetamido)anisole (Desc. 4(b); 4.3 g, 14.4 mmol) was suspended in carbon tetrachloride (80 ml). The suspension was heated to 80° C. and triphenylphosphine (4.54 g, 17.3 mmol) was added in portions over 4 hours. The reaction was stirred at 80° C. for 16 hours. The solvent was removed in vacuo and hexane (100 ml) was added to the residue and heated to reflux temperature. The suspension was allowed to cool to ambient temperature and filtered (triphenylphosphine oxide). The solvent was removed from the filtrate in vacuo leaving an oil (4.6 g). A portion of this oil (2.04 g) was dissolved in tetrahydrofuran (25 ml), cooled to 0° C. and treated with hydrazine hydrate (1.0 ml, 21 mmol). The mixture was stirred at 0° C. for 30 minutes then concentrated in vacuo. The residue was dissolved in acetic acid (100 ml) containing triethyl orthoformate (25 ml) and the solution heated at reflux for 4 hours. The mixture was evaporated, treated with 1M sodium hydroxide solution (100 ml) and extracted with ethyl acetate (2×50 ml). The extracts were washed with brine (50 ml), combined, dried (MgSO$_4$) and evaporated to a orange solid which was purified by trituration with diethyl ether/hexane to afford the title compound as a pale cream solid (2.21 g); $\delta_H$ (250MHz, CDCl$_3$) 3.99 (3H, s, ArOCH$_3$), 7.02 (1H, d, J 8.8Hz, 6-H), 7.32 (1H, dd, J 8.8, 2.6Hz, 5-H), 7.58 (1H, d, J 2.6Hz, 3-H), 8.32 (1H, s, 5'-H).

DESCRIPTION 9
2-Bromo-4-(2-trifluoromethyl-1H-imidazol-1-yl)anisole

2Bromo-4-(trifluoroacetamido)anisole (Desc. 4(b); 4.3 g, 14.4 mmol) was suspended in carbon tetrachloride (80 ml). The suspension was heated to 80° C. and triphenylphosphine (4.54 g, 17.3 mmol) was added in portions over 4 hours. The reaction was stirred at 80° C. for 16 hours. The solvent was removed in vacuo and hexane (100 ml) was added to the residue and heated to reflux temperature. The suspension was allowed to cool to ambient temperature and filtered (triphenylphosphine oxide). The solvent was removed from the filtrate in vacuo leaving an oil (4.6 g). A portion of this oil (3.63 g) was dissolved in tetrahydrofuran (40 ml) and treated with aminoacetaldehyde diethyl acetal (5.0 ml, 34 mmol). The mixture was stirred at room temperature for 3 hours, concentrated in vacuo, redissolved in acetic acid (100 ml) and heated at reflux for 1 hour. The mixture was evaporated, treated with 1M sodium hydroxide solution (250 ml) and extracted with ethyl acetate (2×100 ml). The extracts were washed with brine (100 ml), combined, dried (MgSO$_4$) and evaporated to an amber oil. Purification by flash chromatography, eluting with ethyl acetate/hexane (1:2 then 2:3), gave the title compound (2.60 g); $\delta_H$ (250MHz, CDCl$_3$) 3.97 (3H, s, ArOCH$_3$), 6.98 (1H, d, J 8.7Hz, 6-H), 7.12 (1H, d, J 1.1Hz), 7.21 (1H, d, J 1.1Hz), 7.31 (1H, dd, J 8.7, 2.6Hz, 5-H), 7.58 (1H, d, J 2.6Hz, 3-H).

DESCRIPTION 10
4-Benzyloxy-2-bromoanisole a) 4-Benzyloxy-2-bromophenol

To a suspension of 4-benzyloxyphenol (30 g, 150 mmol) in chloroform (400 ml) was added, dropwise, a solution of bromine (24 g, 150 mmol) in chloroform (150 ml). After stirring for 1 hour the mixture was washed with 0.1M NaHSO$_3$ (500 ml), then water (500 ml). The chloroform layer was separated, dried (MgSO$_4$), filtered and concentrated. The residue was purified by flash column chromatography on silica gel eluting with 5, 10, 20% ethyl acetate/hexane. Recrystallisation from hexane afforded the title compound (20.5 g, 49%); $\delta_H$ (250MHz, CDCl$_3$) 4.98 (2H, s, OCH$_2$), 6.82—6.99 (2H, m, ArH), 7.09–7.12 (1H, d, J 2.75Hz, ArH), 7.30–7.42 (5H, m).

b) 4-Benzyloxy-2-bromoanisole

To a solution of 4-benzyloxy-2-bromophenol (20 g, 71.6 mmol) in N,N-dimethylformamide (65 ml) was added potassium carbonate (12.4 g, 89.6 mmol) and methyl iodide (12.7 g, 89.6 mmol). The mixture was stirred at room temperature for 18 hours, poured into water (250 ml) and extracted with ethyl acetate (2×100 ml). The organic layer was separated, dried (MgSO$_4$), filtered and concentrated in vacuo to give the title compound (20.15 g, 96%), $\delta_H$ (250 MHz, CDCl$_3$) 3.84 (3H, s, ArOCH$_3$), 4.99 (2H, s, OCH$_2$), 6.80–6.94 (2H, m ArH), 7.21 (1H, d, J 2.75Hz, ArH), 7.28–7.43 (5H, m).

DESCRIPTION 11
3-(2-Methoxy-5-(5-trifluoromethyl-1H-tetrazol-1-yl)phenyl)-1-oxa-7-azaspiro[4,5]dec-3-ene hydrochloride 1-Chloroethyl chloroformate (1.9 ml, 17.6 mmol) was added dropwise at 4° C. to a solution of 7-benzyl-3-(2-methoxy-5-(5-trifluoromethyl-1H-tetrazol-1-yl)phenyl)-1-oxa-7-azaspiro[4,5]dec-3-ene (free base of Ex. 2; 6.16 g, 13.07 mmol) in dichloromethane (60 ml). The reaction mixture was stirred at −4° C. for 30 minutes, allowed to warm to room temperature over 30 minutes and stirred at room temperature for 15 minutes. The reaction mixture was concentrated in vacuo, the residual red oil dissolved in methanol (60 ml) and heated at reflux for 40 minutes. The mixture was allowed to cool, concentrated in vacuo and the residue triturated with ether to give a title compound in two crops (3.54 g, 65%), m.p. 203°–205° C.; (Found: C, 48.33; H, 4.44; N, 16.31. $C_{17}H_{19}ClF_3N_5O_2$. $0.25H_2O$ requires C, 48.35; H, 4.65; N, 16.58%); $\delta_H$ (360MHz, DMSO-$d_6$) 1.72–1.96 (4H, m), 2.85 (1H, m), 3.11 (3H, m), 4.00 (3H, s, ArOCH$_3$), 4.99 (2H, m, 2-CH$_2$, 6.64 (1H, br s, 4-CH=), 7.38 (1H, d, J 8.9Hz, 3'-H), 7.65 (1H, d, J 2.5Hz, 6'-H), 7.76 (1H, dd, J 8.9, 2.5Hz, 4'-H); m/z (ES$^+$) 382 ([M+H]$^+$).

DESCRIPTION 12
(±)-(3R*,5R*)-3-(2-Methoxy-5-(5-trifluoromethyl-1H-tetrazol-1-yl)phenyl)-1-oxa-7-azaspiro[4,5]decane and (±)-(3S*,5R*)-3-(2-methoxy-5-(5-trifluoromethyl-1H-tetrazol-1-yl)phenyl)-1-oxa-7-azaspiro[4,5]decane A mixture of 7-benzyl-3-(2-methoxy-5-(5-trifluoromethyl-1H-tetrazol-1-yl)phenyl)-1-oxa-7-azaspiro[4,5]dec-3-ene (free base of Ex. 2; 1.73 g, 3.67 mmol), 20% palladium hydroxide on carbon (0.39 g), and acetic acid (5 ml) in methanol (45 ml) was hydrogenated at 50 psi for 5 hours, during which time two further portions of catalyst were added (0.35 g and 0.39 g). The catalyst was filtered off and replaced by fresh catalyst (0.98 g) and the mixture hydrogenated at 50 psi overnight (14 hours). The reaction mixture was filtered, concentrated in vacuo, treated with saturated sodium hydrogen carbonate (250 ml) and extracted with dichloromethane (100 ml then 2×50 ml). The combined extracts were dried (MgSO$_4$) and concentrated in vacuo to afford the title products as an approximately 7:1 mixture (1.26 g, 90%). The structure of the major diasterisomer [(3R*,5R*)] was assigned on the basis of 500MHz 1D proton, COSY and NOESY NMR experiments; proton data for major isomer, $\delta_H$ (DMSO-$d_6$) 1.35 (1H, m, 9-H$_{eq}$), 1.58 (2H, m, 9-H$_{ax}$, 10-H$_{ax}$), 1.66 (2H, m, 4-H$_{eq}$, 10-H$_{eq}$), 2.35 (1H, dd, J 12.5, 8.1Hz, 4-H$_{ax}$), 2.53 (2H, m, 6H$_{ax}$, 8-H$_{ax}$), 2.65 (2H, m, 6-H$_{eq}$, 8-H$_{eq}$), 3.59 (1H, t, 8.4Hz, 2-H$_{eq}$), 3.72 (1H, m, 3-H), 3.91 (3H, s, ArOCH$_3$), 4.10 (1H, m, 2-H$_{ax}$), 7.24 (1H, d, J 8.7Hz, 3'-H), 7.61 (1H, dd, J 8.7, 2.5Hz, 4'-H). 7.70 (1H. d, J 2.5Hz, 6'H).

DESCRIPTION 13
(±)·(3R*,5R*)-3-(2-Methoxy-5-(5-trifluoromethyl-1H-tetrazol-1-yl)phenyl)-1-oxa-7-azaspiro[4,5]decane hydrochloride 3-(2-Methoxy-5-(5-trifluoromethyl-1H-tetrazol-1-yl)phenyl)-1-oxa-7-azaspiro[4,5]dec-3-ene hydrochloride (Desc. 11; 2.23 g, 5.34 mmol) was hydrogenated in analogous fashion to Description 12, followed by recrystallisation from isopropanol/diethyl ether to afford the title compound (1.04 g, 46%); $\delta_H$(360MHz, D$_2$O) 1.85 (3H, m), 2.01 (2H, m), 2.38 (1H, m), 2.98 –3.09 (2H, m), 3.38 (1H, m), 3.44 (1H, d, J 12.8Hz), 3.94 (2H, m), 3.97 (3H, s, ArOCH$_3$), 4.32 (1H, m), 7.26 (1H, d, J 8.8Hz, 3'-H), 7.53–7.58 (2H, m, ArH); m/z (ES$^+$) 384 ([M+H]$^+$).

DESCRIPTION 14
3-Bromo-4-methoxyphenylhydrazine

A solution of sodium nitrite (3.16 g, 45.8 mmol) in water 30 ml was added dropwise over 30 minutes to a stirred suspension of 4-amino-2-bromoanisole (Desc. 4(a); 7.31 g, 36.2 mmol) in concentrated hydrochloric acid (50 ml), maintaining the temperature below 0° C. The mixture was stirred at ca. 0° C. for 30 minutes then added portionwise to a suspension of tin(II) chloride dihydrate (36.87 g, 163 mmol) in concentrated hydrochloric acid (50 ml) at −10° C. The resulting thick paste was stirred at −2° C. for 15 minutes, allowed to warm to room temperature over 20 minutes and stirred at room temperature for a further 20 minutes. The reaction mixture was recooled, basified with 10M sodium hydroxide solution and extracted with ethyl acetate (2×250 ml). The extracts were washed with brine (250 ml), combined, dried (MgSO$_4$) and concentrated in vacuo to afford 3-bromo-4-methoxyphenylhydrazine (7.27 g, 93%); $\delta_H$ (250MHz, CDCl$_3$) 3.84 (3H, s, ArOCH$_3$), 6.75 (1H, dd, 8.8, 2.6Hz, 6-H), 6.83 (1H, d, 8.8Hz, 5-H), 7.11 (1H, d, 2.6Hz, 2-H).

DESCRIPTION 15
2-Bromo-4-(5-methyl-1H-1,2,4-triazol-1-yl)anisole

Acetamide (6.07 g, 0.103 mol) and dimethylformamide dimethyl acetal (20 ml, 0.15 mol) were stirred at 80° C. in dioxane (20 ml) for 2 hours. The reaction mixture was concentrated in vacuo, ether (50 ml) added, the solution refridgerated for 30 minutes then triturated to give an orange solid. The solid was collected under suction and the fitrate concentrated in vacuo to a red oil (4.63 g). A portion of this oil (1.20 g) was added to a solution of 3-bromo-4-methoxyphenylhydrazine (Desc. 14; 2.12 g, 9.77 mmol) in acetic acid (20 ml) and the mixture stirred at 90° C. for 2 hours. The reaction mixture was concentrated, treated with saturated sodium hydrogen carbonate (150 ml) and extracted with dichloromethane (2×50 ml). The combined extracts were dried (MgSO$_4$), evaporated and the residue purified by flash chromatography, eluting with 1:1 then 3:1 ethyl acetate/hexane then ethyl acetate, to give the title compound (0.33 g, 13%); $\delta_H$ (250MHz, CDCl$_3$) 2.51 (3H, s, 5'—CH$_3$), 3.97 (3H, s, ArOCH$_3$), 7.00 (1H, d J 8.7Hz, 6-H), 7.37 (1H, dd, J8.7, 2.6Hz, 5-H), 7.67 (1H, d, J 2.6Hz, 3-H), 7.92 (1H, s, 3'-H).

DESCRIPTION 16
2-Bromo-4-(5-trifluoromethyl-1H-1,2,4-triazol-1-yl)anisole

Trifluoroacetamide (5.87 g, 51.9 mmol) and dimethylformamide dimethyl acetal (3.3 ml, 62 mmol) were stirred at 80° C. in dioxane (20 ml) for 30 minutes. The reaction mixture was concentrated in vacuo to give a dark yellow oil (7.71 g). A portion of this oil (5.04 g) was added to a solution of 3-bromo-4-methoxyphenylhydrazine (Desc. 14; 4.29 g, 19.8 mmol) in acetic acid (40 ml) and the mixture stirred at 90° C. overnight. The reaction mixture was concentrated in vacuo, the residue dissolved in ethyl acetate (50 ml) and stirred with saturated sodium hydrogen carbonate solution (150 ml) for 15 minutes. The phases were separated and the aqueous phase extracted with ethyl acetate (2×50 ml). The extracts were washed with brine (50 ml), combined and dried (MgSO$_4$). The residue after evaporation was purified by flash chromatography (gradient elution with 1:4, 1:2, 2:1 then 3:1 ethyl acetate/hexane) to afford 2-bromo-4-(5-trifluoromethyl-1H-triazol-1-yl)anisole (0.19 g, 3%), $\delta_H$ (360MHz, CDCl$_3$) 3.98 (3H, s, ArOCH$_3$), 7.00 (1H, d, J 8.8Hz, 6-H), 7.40 (1H, dd, J 8.8, 2.6Hz, 5-H), 7.69 (1H, d, J 2.6Hz, 3-H), 8.11 (1H, s, 3'-H).

DESCRIPTION 17
2-Bromo-4-(N-methyltrifluoroacetamido)anisole

Sodium hydride (60% dispersion in mineral oil, 0.48 g, 12 mmol) was added to a stirred, cooled (0° C.) solution of 2-bromo-4-(trifluoroacetamido)anisole (Description 4(b); 2.98 g, 10 mmol) in dimethylformamide (30 ml). The mixture was stirred at 0° C. for 30 minutes, then methyl iodide (0.75 ml, 1.70 g, 12 mmol) was added. The mixture was stirred at 0° C. for 30 minutes, then at room temperature for 3 hours. Water (50 ml) was added and the mixture was extracted with ethyl acetate (3×50 ml). The combined organic extracts were washed with water (4×50 ml) then brine (50 ml), dried (MgSO$_4$) and the solvent evaporated under reduced pressure. The residue was purified by flash chromatography, eluting with hexane/CH$_2$Cl$_2$ (50:50 increasing to 30:70), to give the title compound as a colorless solid (2.72 g, 87%); $\delta_H$ (250MHz, CDCl$_3$) 3.32 (3H, s, N—CH$_3$), 3.94 (3H, s, ArOCH$_3$), 6.91 (1H, d, J 8.7Hz, 6-H), 7.18 (1H, dd, J 8.7, 2.4Hz, 5-H), 7.46 (1H, d, J 2.4Hz, 3-H).

DESCRIPTION 18
1-(3-Bromo-4-isopropoxyphenyl)-2-trifluoromethyl-1H-imidazole (a) 2-Bromo-4-nitrophenol Bromine (27 ml) was added dropwise to a solution of 4-nitrophenol (50 g) in glacial acetic acid (400 ml) and the mixture stirred at room temperature for 18 hours. The solvent was evaporated under reduced pressure and the residue was crystallised from dichloromethane/hexane. The solid was collected and dried in vacuo to give the title compound as a colorless solid (67 g); $\delta_H$ (250MHz, CDCl$_3$) 7.13 (1H, d, J 8.9 Hz, 6-H), 8.16 (1H, dd, J 2.6, 8.9 Hz, 5-H), 8.44 (1H, d, J 2.6 Hz, 3-H).

(b) 2-Isopropoxy-5-nitrobromobenzene

2-Iodopropane (2.2 g) was added to a mixture of 2-bromo-4-nitrophenol (2.5 g) and potassium carbonate (5 g) in acetone (30 ml) and the mixture heated under reflux for 18 hours. The mixture was cooled and the solvent was evaporated under reduced pressure. Water was added and the mixture was extracted with ethyl acetate. The organic layer was washed with water and brine, dried (MgSO$_4$) and the solvent evaporated under reduced pressure. The residue was purified by flash chromatography, eluting with hexane/EtOAc (90:10), to give the title compound (2.8 g, 94%); $\delta_H$ (250MHz, CDCl$_3$) 1.42 (6H, d, J 5.7Hz, OCH(CH$_3$)$_2$), 4.75 (1H, m, OCH(CH$_3$)$_2$), 6.93 (1H, m, ArH), 8.20 (1H, m, ArH), 8.46 (1H, s, ArH).

(c) 3-Bromo-4isopropoxyaniline

Platinum oxide (50 mg) was added to a solution of 2-isopropoxy-5-nitrobromobenzene (1.7 g, 6.5 mmol) in ethyl acetate (50 ml) and the mixture was stirred under hydrogen (50 psi) for 1 hour. The mixture was filtered, further platinum oxide (50 mg) was added and the mixture was stirred under hydrogen (50 psi) for 1 hour. The mixture was filtered and the solvent was evaporated under reduced pressure. The residue was purified by flash chromatography, eluting with hexane/EtOAc (80:20), to give the title compound (0.92 g, 62%); $\delta_H$ (360MHz, CDCl$_3$) 1.32 (3H, d, J 5.6Hz, OCH(CH$_3$)$_2$), 4.33 (1H, m, OCH(CH$_3$)$_2$), 6.57 (1H, dd, J 8.7, 2.8Hz, 6-H), 6.78 (1H, d, J 8.7Hz, 5-H), 6.91 (1H, d, J 2.8 Hz, 2-H).

(d) N-(3-Bromo-4-isopropoxyphenyl)trifluoroacetamide

Trifluoroacetic anhydride (1.1 ml, 1.64 g, 8 mmol) was added slowly to a stirred, cooled (0° C.) solution of 2-isopropoxy-5-amino-bromobenzene (0.92 g, 4 mmol) and triethylamine (1.1 ml, 0.90 g, 8 mmol) in dichloromethane (10 ml) and the mixture stirred at room temperature for 2 hours. The mixture was diluted with dichloromethane (30 ml) and washed with water (30 ml) and brine (30 ml), dried (MgSO$_4$) and the solvent evaporated under reduced pressure to give the title compound as a beige solid (1.28 g, 100%); $\delta_H$ (360MHz, CDCl$_3$) 1.37 (3H, d, J 5.6Hz, OCH(CH$_3$)$_2$), 4.54 (1H, m OCH(CH$_3$)$_2$), 6.91 (1H, d, J 8.9Hz, 5'-H), 7.46 (1H, dd, J 8.9, 2.7Hz, 6'-H), 7.74 (1H, d, J 2.7Hz, 2'-H).

(e) 1-(3-Bromo-4-isopropoxyphenyl)-2-trifluoromethyl-1H-imidazole

Triphenylphosphine (7.7 g, 29.4 mmol) was added in portions to a stirred, heated (80° C.) suspension of N-(3-bromo-4-isopropoxyphenyl)trifluoroacetamide (8.5 g, 19 mmol) in carbon tetrachloride (100 ml). The mixture was stirred at 80° C. for 2 days, then further triphenylphosphine (2.5 g, 9.5 mmol) was added. The mixture was stirred at 80° C. for 5 hours, cooled and the solvent evaporated under reduced pressure. The residue was triturated with hexane, filtered and the solvent evaporated under reduced pressure to give a yellow oil (6.7 g). A portion (3 g) was dissolved in tetrahydrofuran (40 ml), cooled in ice and aminoacetaldehyde diethyl acetal (3.9 ml, 27 mmol) was added. The mixture was stirred at 0° C. for 30 minutes, the solvent was evaporated under reduced pressure and the residue was dissolved in acetic acid (50 ml). The mixture was heated under reflux for 3 hours, cooled and the solvent evaporated under reduced pressure. Aqueous sodium hydroxide solution (1M, 2×150 ml) was added and the mixture extracted with ethyl acetate (2×150 ml). The combined organic extracts were washed with brine (100 ml), dried (MgSO$_4$) and the solvent evaporated under reduced pressure. The residue was purified by flash chromatography, eluting with hexane/EtOAc (80:20), to give the title compound as an oil (1.3 g); $\delta_H$ (360MHz, CDCl$_3$) 1.43 (6H, d, J 6.0Hz, OCH(CH$_3$)$_2$), 4.63 (1H, sept, J 6.0 Hz, OCH(CH$_3$)$_2$), 6.96 (1H, d J 8.7Hz, 5'-H), 7.10 (1H, d, J 1.1Hz, 4-H or 5-H), 7.20 (1H, d, J 1.1Hz, 5-H or 4-H), 7.25 (1H, dd, J 8.7, 2.6Hz, 6'-H), 7.56 (1H, d, J 2.6Hz, 2'-H); m/z (ES$^+$) 349, 351 ([M+H]$^+$).

DESCRIPTION 19
2-Bromo-4-(5-trifluoromethyl-1H-tetrazol-1-yl)methylanisole a) 2-Bromo-4-aminomethylanisole Borane-tetrahydrofuran complex (1.0 M solution in tetrahydrofuran. 250 ml) was added to a solution of 2-bromo-4-cyanoanisole (17 g) in tetrahydrofuran (150 ml). The mixture was heated at reflux for 2 hours then cooled to −10° C. and carefully quenched with 6N HCl (130 ml). The mixture was basified with 4N NaOH then extracted with ethyl acetate. The organic layer was separated, dried (MgSO$_4$), filtered and concentrated in vacuo. The residue was purified by flash chromatography, eluting with 120:8:1 dichloromethane:methanol:ammonia, to give the title compound (12.3 g, 71%); $\delta_H$ (250MHz, CDCl$_3$) 3.80 (2H, s, CH$_2$NH$_2$), 3.92 (3H, s, ArOCH$_3$), 6.85 (1H, d, J 8.4Hz, 6-H), 7.20 (1H, dd, J 8.4, 2.1Hz, 5-H), 7.51 (1H, d, J 2.1Hz, 3-H).

b) 2-Bromo-4-(trifluoroacetamido)methylanisole

Triethylamine (14.4 g, 142 mmol) was added to a solution of 2-bromo-4-methylaminoanisole (12.3 g, 57 mmol) in dichloromethane (300 ml). The solution was cooled with an ice-acetone bath and trifluoroacetic anhydride (11.9 g, 57 mmol) was added slowly. The mixture was stirred at ambient temperature for 18 hours then washed with water (2×100 ml). The organic layer was separated, dried (MgSO$_4$), filtered and concentrated in vacuo. Chromatography on silica gel, eluting with 30% ethyl acetate in hexane, gave the title compound (12.2 g, 69%); $\delta_H$(250HHz, CDCl$_3$) 3.88 (3H, s, ArOCH$_3$), 4.42 (2H, d, J 5.9Hz, CH$_2$), 6.87 (1H, d, J 8.4Hz, 6-H), 7.21 (1H, dd, J 8.4, 2.1Hz, 5-H), 7.47 (1H, d, J 2.1Hz, 3-H).

c) 2-Bromo-4-(5-trifluoromethyl-1H-tetrazol-1-yl)methylanisole 2-bromo-4-(trifluoroacetamido)methylanisole (5 g, 16 mmol) was suspended in carbon tetrachloride (125 ml).

Triphenylphosphine (8 g, 30.5 mmol) was added and the mixture stirred at 80° C. for 16 hours. Solvent was removed in vacuo and the residue poured into hexane (100 ml) and stirred at reflux for 30 minutes. The suspension was filtered through Hyflo™ and the filtrate concentrated to an oil. The oil in N,N-dimethylformamide (15 ml) was added to a stirred solution of sodium azide (1 g, 15 mmol) in N,N-dimethylformamide at 0° C. The mixture was stirred at ambient temperature for 2 hours then poured into water (200 ml) and extracted with ethyl acetate (2×100 ml). The combined organics were washed with water (3×200 ml), dried over sodium sulfate and the solvent was removed in vacuo leaving a yellow oil. Chromatography on silica gel, eluting with 10–50% ethyl acetate in hexane, gave the title compound as a yellow oil (230 mg, 5%, $\delta_H$ (360MHz, CDCl$_3$) 4.90 (1H, d, J 7.6Hz, NCH$_A$H$_B$Ar), 4.95 (1H, d, J 7.6 Hz, NCH$_A$H$_B$Ar), 7.00 (1H, d, J 8.6Hz, 6-H), 7.52 (1H, dd, J 2.2, 8.5Hz, 5-H), 7.80 (1H, d, 2.2Hz, 3-H); m/z (ES$^+$) 337, 339 ([M+H]$^+$).

DESCRIPTION 20
(±)-(3R*,5R*)-3-(2-Methoxy-5-(2-trifluoromethyl-1H-imidazol-1-yl)phenyl)-1-oxa-7-azaspiro[4.5]decane oxalate 7-Benzyl-3-(2-methoxy-5-(2-trifluoromethyl-1H-imidazol-yl)phenyl)-1-oxa-7-azaspiro[4.5]-dec-3-ene (4.2 g), 20% palladium hydroxide on carbon (0.5 g) in methanol (40 ml) was hydrogenated at 50 psi for 5 days during which time the catalyst was filtered off and replaced by fresh twice. The reaction mixture was filtered through Hyflo™ then concentrated in vacuo. The residue was purified by flash chromatography eluting with 90:8:1 dichloromethane:methanol:ammonia. Treatment with oxalic acid afforded the oxalate salt which was recrystallised from isopropanol/diethyl ether (1.97 g, 49%); $\delta_H$ (360MHz, D$_2$O) 1.77–1.99 (5H, m), 2.31–2.36 (1H, m), 2.97–3.07 (2H, m), 3.35–3.43 (2H, m), 3.88–3.93 (5H, m), 4.25–4.32 (1H, m), 7.12–7.14 (1H, d, J 9.5Hz, 3'-H), 7.24–7.25 (1H, d, J 1.2Hz, imidzole H), 7.35–7.36 (2H, m), 7.37–7.38 (1H, d, J 1.2Hz, imidazole H); m/z (ES$^+$382 ([M+H]$^+$).

DESCRIPTION 21
(2R)-1-Phenyl-2-(p-toluenesulfonyloxy)propane (2R)-1-Phenyl-2-propanol (0.5 ml, 3.65 mmol) was added dropwise to a solution of p-toluenesulfonyl chloride (0.73 g, 3.83 mmol) in pyridine) (3 ml) at 0° C. The mixture was stirred at 0° C. under nitrogen for 30 minutes then at room temperature overnight. The reaction mixture was poured into 2M hydrochloric acid (75 ml) and extracted with diethyl ether (2×50 ml). The extracts were washed with 2M hydrochloric acid (50 ml), saturated sodium hydrogen carbonate (50 ml) and brine (50 ml), combined, dried (MgSO$_4$) and concentrated in vacuo to give the title compound as a white solid (0.95 g, 90%); $\delta_H$ (250MHz, CDCl$_3$) 1.30 (3H, d, J 6.2Hz, CHCH$_3$), 2.42 (3H, s, ArCH$_3$), 2.77 (1H, dd, J 13.8, 6.6Hz, CH(OTs)CH$_A$H$_B$Ph), 2.92 (1H, dd, J 13.8, 6.6Hz, CH(OTs)CH$_A$H$_B$Ph), 4.74 (1H, m, CHOTs), 7.03 (2H, m, ArH), 7.20 (5H, m, ArH), 7.62 (1H, m. ArH).

EXAMPLE 1
7-Benzyl-3-(2-methoxyphenyl)-1-oxa-7-azaspiro[4,5]dec-3-ene hydrochloride A mixture of 7-benzyl-3-tributylstannyl-1-oxa-7-azaspiro [4,5]dec-3-ene (Desc. 3; 1.68 g, 3.24 mmol), 2-bromoanisole (0.80 ml, 6.42 mmol), lithium chloride (0.94 g, 22 mmol) and tetrakis(triphenylphosphine)palladium(0) (0.37 g, 0.32 mmol) in toluene (40 ml) was degassed then heated at reflux overnight (17 hours). The mixture was allowed to cool, filtered and concentrated in vacuo. The residue was dissolved in ether (100 ml) and extracted with 2M hydrochloric acid (100 ml then 25 ml). The aqueous phases were washed with more ether (100 ml), combined, basified with 4 M sodium hydroxide (70 ml) and extracted with ethyl acetate (2×50 ml). The organic phases were washed with brine (50 ml), dried (MgSO$_4$) and concentrated. The residue was purified by flash chromatography, eluting with ethyl acetate/hexane (1:2 then 1:1), to give 7-benzyl-3-(2-methoxyphenyl)-1-oxa-7-azaspiro[4,5]dec-3-ene (0.67 g, 62%. This oil was dissolved in isopropanol and treated with excess ethereal hydrogen chloride. The mixture was concentrated in vacuo and recrystallised from isopropanol/diethyl ether to afford the title compound, m.p. 198°–201° C.; (Found: C, 69.61; H, 6.85; N, 3.62. C$_{22}$H$_{26}$ClNO$_2$0.4H$_2$O requires C, 69.70; H, 7.13; N, 3.69%); $\delta_H$(360MHz, D$_2$O) 1.78–2.22 (4H, m), 2.98–3.26 (3H, m), 3.58 (1H, m), 3.89 (3H, s, ArOCH$_3$), 4.29 (1H, br d, NCH$_A$H$_B$Ph), 4.43 (1H, d, J 13.1Hz, NCH$_A$H$_B$Ph), 5.00 (2H, m, 2-CH$_2$), 6.33 (1H, br, s, 4-H), 7.02 (1H, t, J 7.5Hz, ArH), 7.11 (1H, d, J 8.4Hz, ArH), 7.16 (1H, m, ArH), 7.39 (1H, m, ArH), 7.53 (5H, m, PhH); m/z (ES$^+$) 336 ([M+H]$^+$).

EXAMPLE 2
7-Benzyl-3-(2-methoxy-5-(5-trifluoromethyl-1H-tetrazol-1-yl)phenyl)-1-oxa-7-azaspiro[4,5]dec-3-ene hydrochloride Prepared in an analogous fashion to Example 1 using the bromide of Description 4.

M.p. 221°–223° C. (IPA/Et$_2$O); (Found: C,56.35; H, 4.83; N, 13.33. C$_{24}$H$_{25}$ClF$_3$N$_5$O$_2$.0.2H$_2$O requires C, 56.35; H, 5.01; N, 13.69%); $\delta_H$(360MHz, D$_2$O) 1.80–2.12 (4H, m), 3.03 (1H, m), 3.15 (1H, br d), 3.24 (1H, br d), 3.56 (1H, m), 3.96 (3H, s, ArOCH$_3$), 4.32 (1H, br d, NCH$_A$H$_B$Ph), 4.42 (1H, d. J 13.1Hz, NCH$_a$H$_B$Ph), 4.97 (2H, m, 2—CH$_2$), 6.45 (1H, br s, 4—CH=). 7.25 (1H, d, J 9.0Hz, 3'-H), 7.33 (1H, br s, 6'-H), 7.49 (5H, br s, PhH), 7.54 (1H, m, 4'-H); m/z (ES$^+$) 472 ([M+H]$^+$).

Separation of the enantiomers of the title compound was carried out by chiral HPLC on a Chiralcel OD-H 5 µm column (250×4 mm i.d.), eluting with 5% ethanol in hexane (1.5 ml/min). Peaks observed for enantiomers at 10.8 and 16.8 minutes.

EXAMPLE 3
7-Benzyl-3-(2-methoxy-5(1H-tetrazol-1-yl)phenyl)-1-oxa-7-azaspiro[4,5]dec-3-ene hydrochloride Prepared in an analogous fashion to Example 1 using the bromide of Description 5.

$\delta_H$ (360MHz, DMSO-d$_6$) 1.60–1.92 (4H, m), 2.58–2.96 (4H, m), 3.98 (3H, s, ArOCH$_3$), 4.02–4.10 (2H, br d, NCH$_2$Ph), 4.96–5.04 (2H, m, 2—CH$_2$), 6.59 (1H, s, 4—CH=), 7.32–7.43 (7H, m), 7.65 (1H, m) 7.83 (1H, d, J 6.55Hz, ArH), 10.00 (1H, s, tetrazole H); m/z (ES$^+$) 404 ([M+H]$^+$).

EXAMPLE 4
7-Benzyl-3-(2-methoxy-5-(4-pyridyl)phenyl)-1-oxa-7-azaspiro[4.5]dec-3-ene dihydrochloride Prepared in an analogous fashion to Example 1 using 2-bromo-4-(4'-pyridyl)anisole (Description 6).

$\delta_H$(360MHz, D$_2$O) 1.78–2.09 (4H, m), 3.01–3.26 (3H, m), 3.56–3.61 (1H, m), 3.88 (3H, s, ArOCH$_3$), 4.22–4.50 (2H, m), 5.00–5.10 (2H, m), 6.38 (1H, s), 7.22 (1H, m), 7.38–7.56 (6H, m), 7.91 (1H, m), 8.06 (2H, m), 8.62 (2H, m); m/z (ES$^+$) 414 ([M+H]$^+$).

EXAMPLE 5
7-Benzyl-3-(2-methoxy-5-cyanophenyl)-1-oxa-7-azaspiro [4,5]dec-3-ene hydrogen oxalate Prepared in an analogous fashion to Example 1 using 2-bromo-4-cyanoanisole.

$\delta_H$(360MHz, DMSO-$d_6$) 1.63–1.87 (4H, m), 2.62–2.87 (4H, m), 3.94 (3H, s, ArOCH$_3$), 3.97 (2H, s, NCH$_2$Ph), 4.95 (2H, m), 6.55 (1H, s), 7.26 (1H, d, J 8.75Hz, ArH), 7.38–7.43 (5H, m), 7.63 (1H, d, J 1.9Hz), 7.77–7.80 (1H, m); m/z (ES$^+$) 360 ([M+H]$^+$).

EXAMPLE 6

7-Benzyl-3-(2-methoxy-5-trifluoromethoxyphenyl)-1-oxa-7-azaspiro[4,5]dec-3-ene hydrochloride Prepared in an analogous fashion to Example 1 using the bromide of Description 7.

$\delta_H$(360MHz, DMSO-$d_6$) 1.69–1.85 (3H, m), 2.02–2.18 (1H, m), 2.87–2.94 (1H, m), 3.05 (2H, s), 3.35–3.45 (1H, m), 3.78 (3H, s, ArOCH$_3$), 4.15–4.32 (2H, M), 4.86–4.95 (2H, m), 7.11–7.13 (1H, m), 7.37–7.42 (5H, m); m/z (ES$^+$) 420 ([M+H]$^+$).

EXAMPLE 7

7-Benzyl-3-(2-methoxy-5-(3-trifluoromethyl-4H-1,2,4-triazol-4-yl)phenyl)-1-oxa-7-azaspiro[4,5]-dec-3-ene hydrochloride Prepared in an analogous fashion to Example 1 using the bromide of Description 8.

M.p. 221°–224° C. (IPA/Et$_2$O); (Found: C, 57.21; H, 5.02; N, 10.27. C$_{25}$H$_{26}$ClF$_3$N$_4$O$_2$, 1.0H$_2$O requires C, 57.20; H, 5.38; N, 10.67%); $\delta_H$(360MHz, D$_2$O) 1.84–2.16 (4H, m), 3.04–3.30 (3H, m), 3.58 (1H, m), 3.98 (3H, s, ArOCH$_3$), 4.35 (1H, br d, NCH$_A$H$_B$Ph), 4.45 (1H, d, J 13.1Hz, NCH$_A$H$_B$Ph), 5.00 (2H, m, 2—CH$_2$), 6.48 (1H, br s, 4—CH↑), 7.26 (1H, d, J 9.0Hz, 3'-H), 7.30 (1H, d, J 2.5Hz, 6'-H), 7.49–7.53 (6H, m, ArH); m/z (ES$^+$) 471 ([M+H]$^+$).

EXAMPLE 8

7-Benzyl-3-(2-methoxy-5-(2-trifluoromethyl-1H-imidazol-1-yl)phenyl)-1-oxa-7-azaspiro[4,5]-dec-3-ene hydrochloride Prepared in an analogous fashion to Example 1 using the bromide of Description 9.

(Found: C, 57.43; H, 5.60; N, 7.39. C$_{26}$H$_{27}$ClF$_3$N$_3$O$_2$, 2H$_2$O requires C, 57.62; H, 5.77; n, 7.75%); $\delta_H$ (360MHz, D$_2$O) 1.78–2.14 (4H, m), 3.05 (1H, m), 3.18 (2H, m), 3.60 (1H, m), 3.93 (3H, s, ArOCH$_3$), 4.29 (1H, d, J 13.2Hz, NCH$_A$H$_B$Ph), 4.45 (1H, d, J 13.1Hz, NCH$_A$H$_B$Ph), 4.94 (2H, m, 2—CH$_2$), 6.42 (1H, s, 4—CH=), 7.15 (1H, d, J 8.9Hz, 3'-H), 7.19 (1H, d, J 2.5Hz, 6'-H), 7.26 (1H, d, J 1.2Hz, imidazole H), 7.37 (2H, m, imidazole H and 4'-H) 7.49 (5H, br s, PhH); m/z (ES$^+$) 470 ([M+H]$^+$).

EXAMPLE 9

7-Benzyl-3-(2-methoxy-5-benzyloxyphenyl)-1-oxa-7-azaspiro[4,5]dec-3-ene

Prepared in an analogous fashion to Example 1 using 4-benzyloxy-2-bromoanisole (Description 10).

$\delta_H$ (250MHz, CDCl$_3$) 1.60–1.75 (3H, m), 1.79–1.91 (1H, m), 2.38–2.59 (4H, m), 3.57 (2H, s), 3.83 (3H, s), 4.91–5.03 (4H, m), 6.60 (1H, s), 6.73–6.86 (3H, m), 7.20–7.45 (10H, m); m/z (ES$^+$) 442 ([M+H]$^+$).

EXAMPLE 10

7-Benzoyl-3-(2-methoxy-5-(5-trifluoromethyl-1H-tetrazol-1-yl)phenyl)-1-oxa-7-azaspiro[4,5]dec-3-ene Benzoyl chloride (0.10 ml, 0.86 mmol) was added to a solution of 3-(2-methoxy-5-(5-trifluoromethyl-1H-tetrazol-1-yl)phenyl)-1-oxa-7-azaspiro[4,5]dec-3-ene hydrochloride (Desc. 11; 0.33 g, 0.79 mmol) in pyridine (5 ml) at 0° C. The mixture was stirred at 0° C. for 1½ hours, allowed to warm to room temperature and concentrated in vacuo. 1M Hydrochloric acid (50 ml) was added to the residue and the mixture extracted with dichloromethane (2×25 ml). The combined extracts were dried (MgSO$_4$), concentrated and the residue purified by flash chromatography, eluting with 2½% methanol in dichloromethane, to afford the title compound as a white foam (0.26 g, 68%), which was recrystallised from ethyl acetate/hexane, m.p. 154°–156° C.; (Found: C, 59.29; H, 4.45; N, 14.15, C$_{24}$H$_{33}$F$_3$N$_5$O$_3$ requires C, 59.38; H, 4.57; N, 14.43%); $\delta_H$(360MHz, DMSO-$d_6$, 353K) 1.62 (1H, m), 1.75–1.85 (3H, m), 3.19 (1H, m), 3.39 (1H, br d, J 12Hz), 3.49 (1H, m), 3.80 (1H, m), 3.94 (3H, s, ArOCH$_3$), 4.74 (1H, m, 2-CH$_A$H$_B$), 4.89 (1H, dd, J 12.6, 1.9Hz, 2—CH$_A$H$_B$), 6.52 (1H, br s, 4—CH=), 7.30 (1H, d, J 8.8Hz, 3'-H), 7.37 (5H, m, PhH), 7.55 (1H, d, J 2.6Hz, 6'-H), 7.63 (1H, dd, J 8.8, 2.6Hz, 4'-H); m/z (ES$^+$) 486 ([M+H]$^+$).

EXAMPLE 11

7-(3,4-Dichlorobenzyl)-3-(2-methoxy-5-(5-trifluoromethyl-1H-tetrazol-1-yl)phenyl)-1-oxa-7-azaspiro[4,5]dec-3-ene hydrochloride 3,4-Dichlorobenzyl bromide was added to a mixture of 3-(2-methoxy-5-(5-trifluoromethyl-1H-tetrazol-1-yl)phenyl)-1-oxa-7-azaspiro[4,5]dec-3-ene hydrochloride (Desc. 11; 200 mg, 0.48 mmol) and potassium carbonate (200 mg, 1.44 mmol) in dimethylformamide (10 ml) at room temperature. After stirring for one hour the mixture was poured into water (100 ml) and extracted with ethyl acetate (2×50 ml). The organic layer was separated, dried (MgSO$_4$), filtered and concentrated in vacuo. The residue was purified by flash column chromatography on silica gel eluting with 2, 2.5 and 5% methanol/dichloromethane. Treatment with ethereal hydrogen chloride afforded the hydrochloride salt which was recrystallised from isopropanol/diethyl ether (58 mg, 22%); $\delta_H$ (360MHz, MeOD), 1.81–2.05 (3H, m), 2.17–2.30 (1H, m), 3.04–3.58 (4H, m), 4.05 (3H, s, ArOCH$_3$), 4.37 (2H, m), 5.11 (2H, s), 6.52 (1H, s), 7.35 (1H, m), 7.50 (2H, m), 7.60 (1H, m), 7.68 (1H, m), 7.81 (1H, m); m/z (ES$^+$) 540 ([M+H]$^+$).

EXAMPLE 12

7-(4-Pyridyl)-3-(2-methoxy-5-(5-trifluoromethyl-1H-tetrazol-1-yl)phenyl)-1-oxa-7-azaspiro[4,5]dec-3-ene dihydrochloride Prepared in an analogous fashion to Example 11 using 4-picolyl chloride.

$\delta_H$ (360MHz, D$_2$O) 1.82–2.24 (4H, m), 3.18–3.24 (1H, m), 3.30–3.42 (2H, m), 3.59–3.63 (1H, m), 4.01 (3H, s, ArOCH$_3$), 4.68–4.82 (2H, m), 5.07 (2H, s, NCH$_2$Py), 6.52 (1H, s), 7.31 (1H, d, J 9.0Hz, 3'-H), 7.41 (1H, d, J 2.6Hz, 5'-H), 7.62 (1H, m), 8.16 (2H, d, J 6.5Hz), 8.90 (2H, d, J 6.35Hz); m/z (ES$^+$) 473 ([M+H]$^+$).

EXAMPLE 13

7-(3-Pyridyl)-3-(2-methoxy-5-(5-trifluoromethyl-1H-tetrazol-1-yl)phenyl)-1-oxa-7-azaspiro[4,5]dec-3-ene dihydrochloride Prepared in an analogous fashion to Example 11 using 3-picolyl chloride.

$\delta_H$(360MHz, D$_2$O) 1.88–2.20 (4H, m), 3.07–3.60 (4H, m), 4.00 (3H, s, ArOCH$_3$), 4.65 (2H, s), 5.05 (2H, s), 6.52 (1H, s), 7.32 (1H, d, J 9.0Hz, 3'-H), 7.43 (1H, m, ArH), 7.61 (1H, m, ArH), 8.11 (1H, m), 8.65 (1H, m), 8.89 (1H, m), 8.98 (1H, m); m/z (ES$^+$) 473 ([M+H]$^+$).

EXAMPLE 14

7-(2-Pyridyl)-3-(2-methoxy-5-(5-trifluoromethyl-1H-tetrazol-1-yl)phenyl)-1-oxa-7-azaspiro[4,5]dec-3-ene dihydrochloride Prepared in an analogous fashion to Example 11 using 2-picolyl chloride.

M.p. 119°–122° C.; (Found: C, 50.40; H, 4.91; N, 14.95. $C_{23}H_{25}Cl_2F_3N_6O_2$ requires C, 50.65; H, 4.62; N, 15.41%); $\delta_H$(360MHz, $D_2O$) 1.84–2.22 (4H, m), 3.16–3.22 (1H, m), 3.28–3.41 (2H, m), 3.58–3.61 (1H, m), 4.00 (3H, s, ArOCH$_3$), 4.54 (2H, q, J 13.8Hz, N—CH$_2$), 5.05 (2H, s, O—CH$_2$), 6.53 (1H, s), 7.29 (1H, d, J 9.1Hz), 7.41 (1H, d, J 2.6Hz), 7.58–7.60 (2H, m), 7.67 (1H, d, J 7.8Hz), 8.00–8.04 (1H, m), 8.68 (1H, m); m/z (ES$^+$) 473 ([M+H]$^+$).

EXAMPLE 15

7-(2-Methoxybenzyl)-3-(2-methoxy-5-(5-trifluoromethyl-1H-tetrazol-1-yl)phenyl)-1-oxa-7-azaspiro[4,5]dec-3-ene hydrochloride Prepared in an analogous fashion to Example 11 using 2-methoxybenzyl chloride.

M.p. 210°–214° C.; (Found: C, 56.07; H, 4.84; N, 12.90. $C_{25}H_{27}ClF_3N_5O_3$ requires C, 55.82; H, 5.06; N, 13.02%); $\delta_H$(360MHz, $D_2O$), 1.82–2.20 (4H, m), 3.01–3.10 (1H, m), 3.21 (2H, m), 3.60–3.64 (1H, m), 3.93 (3H, s), 3.95 (3H, s), 4.40 (2H, q, J 13.4Hz), 5.00–5.08 (2H, m), 6.49 (1H, s), 7.06–7.10 (1H, m), 7.12–7.14 (1H, m), 7.26–7.28 (1H, m), 7.36–7.37 (1H, m), 7.37–7.40 (1H, m), 7.48–7.57 (2H, m); m/z (ES$^+$) 520 ([M+H]$^+$).

EXAMPLE 16

7-(1-Phenylethyl)-3-(2-methoxy-5-(5-trifluoromethyl-1H-tetrazol-1-yl)phenyl)-1-oxa-7-spiro[4,5]dec-3-ene diastereoisomers A and B Prepared in an analogous fashion to Example 11 using (1-bromoethyl)benzene. Separation of the diastereoisomers was accomplished by flash chromatography followed by preparative layer chromatography eluting with methanol/dichloromethane.

Diastereoisomer A: $\delta_H$(360MHz, CDCl$_3$) 1.38 (3H, d, J 6.8Hz, NCH(Ph)CH$_3$), 1.56–1.78 (4H, m), 2.30–2.42 (2H, m), 2.50–2.58 (2H, m), 3.55 (1H, q, J 6.8Hz, NCH(Ph)CH$_3$), 4.00 (3H, s, ArOCH$_3$), 4.98 (2H, m, 2—CH$_2$), 6.74 (1H, br, s, 4—CH=), 7.08 (1H, d J 8.9Hz, 3'-H), 7.22–7.37 (7H, m, ArH); m/z (ES$^+$) 468 ([M+H]$^+$).

Diastereoisomer B: $\delta_H$ (360MHz, CDCl$_3$) 1.37 (3H, d, J 6.8 Hz, NCH(Ph)CH$_3$), 1.56–1.68 (3H, m), 1.82 (1H, m), 2.46 (4H, m), 3.35 (1H, q, J 6.8Hz, NCH(Ph)CH$_3$), 3.99 (3H, s, ArOCH$_3$), 4.98 (2H, m, 2—CH$_2$), 6.69 (1H, br s, 4—CH=), 7.07 (1H, d, J 8.9Hz, 3'-H), 7.21–7.36 (7H, m, ArH); m/z (ES$^+$) 486 ([M+H]$^+$).

EXAMPLE 17

7-(2-Phenylethyl)-3-(2-methoxy-5-(5-trifluoromethyl-1-H-tetrazol-1-yl)phenyl)-1-oxa-7-azaspiro[4,5]dec-3-ene hydrochloride Prepared in an analogous fashion to Example 11 using (2-bromoethyl)benzene.

(Found: C, 55.62; H, 5.20; N, 12.60. $C_{25}H_{27}ClF_3N_5O_2$. 1.0H$_2$O requires C, 55.61; H, 5.41; N, 12.97%); $\delta_H$(360MHz, $D_2O$) 1.88–2.10 (4H, m), 3.02–3.13 (3H, m), 3.20 (1H, d, J 12.6Hz), 3.45 (3H, m), 3.60 (1H, m), 4.02 (3H, s, ArOCH$_3$), 5.07 (2H, m, 2—CH$_2$), 6.52 (1H, br s 4—CH=), 7.32–7.35 (4H, m, ArH), 7.40–7.44 (3H, m, ArH), 7.62 (1H, m, ArH); m/z (ES$^+$) 486 ([M+H]$^+$).

EXAMPLE 18

7-Cyclohexylmethyl-3-(2-methoxy-5-(5-trifluoromethyl-1H-tetrazol-1-yl)phenyl)-1-oxa-7-azaspiro[4,5dec-3-ene hydrochloride Prepared in an analogous fashion to Example 11 using bromomethylcyclohexane.

M.p. 213°–215° C. (IPA/Et$_2$O); $\delta_H$ (360MHz, MeOD) 1.06–1.39 (5H, m), 1.61–1.98 (8H, m), 2.16–2.34 (1H, m), 2.84–3.08 (3H, m), 3.10–3.20 (1H, m), 3.36–3.45 (2H, m), 4.02 (3H, s, ArOCH$_3$), 5.11 (2H, s, OCH$_2$), 6.51 (1H, s), 7.30–7.38 (1H, m, ArH), 7.49 (1H, m, ArH), 756–7.61 (1H, m, ArH); m/z (ES$^+$) 478 (M+H)$^+$.

EXAMPLE 19

7-(5-Dimethylaminomethyl-1H-1,2,3-triazol-4-yl)methyl-3-(2-methoxy-5-(5-trifluoromethyl-1H-tetrazol-1-yl)phenyl)-1-oxa-7-azaspiro[4,5]dec-3-ene dihydrochloride 3-(2-Methoxy-5-(5-trifluoromethyl-1H-tetrazol-1-yl)phenyl)-1-oxa-7-azaspiro[4,5]dec-3-ene hydrochloride (Desc. 11; 322.0 mg, 0.795 mmol) in dimethylformamide (5 ml) was added dropwise over 15 minutes to a mixture of 1,4-dichloro-2-butyne (0.41 ml, 4.1 mmol) and potassium carbonate (0.88 g, 6.4 mmol) in dimethylformamide (5 ml) at 65° C. The reaction mixture was stirred at 65° C. for 2 hours, allowed to cool and poured into water (100 ml). The mixture was extracted with ethyl acetate (2×50 ml), the extracts washed with brine (50 ml), combined and dried (MgSO$_4$). The residue after evaporated was purified by flash chromatography, eluting with ethyl acetate/hexane (1:1, 2:1 then 3:1) to give an oil (151.2 mg). This oil (145.3 mg) was dissolved in dimethylsulfoxide (3 ml), sodium azide (27.9 mg) was added and the mixture stirred at room temperature overnight (16 hours). The reaction mixture was diluted with saturated ammonium chloride solution (40 ml) and extracted with ethyl acetate (2×20 ml). The extracts were washed with brine (20 ml), combined, dried (MgSO$_4$) and evaporated under high vacuum at room temperature. The residual brown oil (145.6 mg) was dissolved in 1,4-dioxane (2 ml) and added to dimethylamine (1.5 ml) at −78° C. The mixture was sealed in a tube and heated at 85° C. overnight (18 hours). The reaction was concentrated in vacuo and the residue purified by flash chromatography eluting with dichloromethane/methanol/ammonia (90:8:1, 60:8:1 then 45:8:1) to give a pale brown foam (94.6 mg, 24% over 3 steps). The foam was dissolved in methanol/diethyl ether and treated with 1M ethereal hydrogen chloride (0.4 ml). The mixture was concentrated in vacuo and triturated with diethyl ether to give a solid which was recrystallised from isopropanol/diethyl ether to afford the title compound as a buff solid, m.p. >170° C.; (Found: C, 45.25; H, 5.31; N, 20.34. $C_{33}H_{30}Cl_2F_3N_9O_2$. 1.0H$_2$O requires C, 45.25; H, 5.28; N, 20.65%); $\delta_H$ (360MHz, $D_2O$) 1.82–2.12 (4H, m), 2.96 (6H, s, NMe$_2$), 3.09 (1H, m), 3.26 (1H, br, d, J 12.4Hz), 3.45 (1H, m), 3.56 (1H, m), 4.02 (3H, s, ArOCH$_3$), 4.56 (2H, s, CH$_2$N), 4.58 (2H, s, CH$_2$N), 5.07 (2H, m, 2—CH$_2$), 5.54 (1H, br s, 4—CH=), 7.33 (1H, d, J 9.0Hz, 3'-H), 7.43 (1H, d, J 2.6Hz, 6'-H), 7.63 (1H, dd, J 9.0, 2.6Hz, 4'-H); m/z (ES$^+$) 520 ([M+H]$^+$).

EXAMPLE 20

(±)-(3R*,5R*)-7-Benzyl-3-(2-methoxy-5-(5-trifluoromethyl-1H-tetrazol-1-yl)phenyl)-1-oxa-7-azaspiro[4,5]decane hydrochloride and (±)-(3S*,5R*)-7-Benzyl-3-(2-methoxy-5-(5-trifluoromethyl-1H-tetrazol-1-yl)phenyl-1-oxa-7-azaspiro[4,5]decane hydrochloride Prepared in an analogous fashion to Example 11, using the mixture of diastereoisomers of Description 12 and benzyl bromide. The diastereoisomers were separated by flash chromatography, eluting with ethyl acetate/hexane (1:2, 2:3 then 1:1), to afford pure major diastereomer [(3R*, 5R*)] followed by preparative layer chromatography, eluting three times with 1:4 ethyl acetate/hexane, to affect purification of the minor diastereoisomer [(3S*,5R*)]. Hydrochloride salts were prepared as before.

Data for (±)-(3R*,5R*)-7-benzyl-3-(2-methoxy-5-(5-trifluoromethyl-1H-tetrazol-1-yl)phenyl)-1-oxa-7-azaspiro[4,5]decane hydrochloride:

$\delta_H$(500MHz, MeOD) 1.66 (1H, m, 10-H$_{ax}$), 1.85 (2H, m, 9-H$_{eq}$, 10-H$_{eq}$), 1.98 (1H, dd, J 13.9Hz, 4-H$_{ax}$), 2.17 (1H, m, 9-H$_{ax}$), 2.28 (1H, m, 4-H$_{eq}$), 2.97 (2H, m, 8-H$_{ax}$, 6-H$_{ax}$), 3.33 (1H, m, 6-H$_{eq}$), 3.47 (1H, m, 8-H$_{eq}$), 3.80 (1H, m, 3-H), 3.89 (1H, m, 2-H$_{ax}$), 3.95 (3H, s, ArOCH$_3$), 4.19 (1H, t, J 7.8Hz, 2-H$_{eq}$), 4.27 (1H, d, J 13Hz, NCH$_A$H$_B$Ph), 4.39 (1H, d, J 13Hz, NCH$_A$H$_B$Ph), 7.22 (1H, d, J 8.4Hz, 3'-H), 7.55 (7H, m, ArH); m/z (ES$^+$) 474 ([M+H]$^+$).

Data for (±)-(3S*,5R*)-7-benzyl-3-(2-methoxy-5-(5-trifluoromethyl-1H-tetrazol-1-yl)phenyl)-1-oxa-7-azaspiro[4,5]decane hydrochloride:

$\delta_H$ (500MHz, MeOD) 1.64 (1H, dt, J 4, 13.5Hz, 10-H$_{ax}$), 1.90 (1H, m, 9-H$_{eq}$), 1.94 (1H, m, 4-H$_{ax}$), 2.01 (1H, m, 10-H$_{eq}$), 2.17 (1H, m, 9-H$_{eq}$), 2.22 (1H, m, 4-H$_{eq}$), 3.01 (2H, m, 8-H$_{ax}$, 6-H$_{ax}$), 3.50 (1H, m, 8-H$_{eq}$), 3.71 (1H, t, J 9.0Hz, 2-H$_{ax}$), 3.87 (3H, s, ArOCH$_3$), 3.89 (1H, m, 3-H), 4.24 (2H, m, NCH$_A$H$_B$Ph, 2-H$_{eq}$), 4.40 (1H, d, J 13.1Hz, NCH$_A$H$_B$Ph), 7.20 (1H, d, J 8.4Hz, 3'-H), 7.42 (1H, d, J 2.5Hz, 6'-H), 7.50(6H, m, ArH); m/z (ES$^+$)474 ([M+H]$^+$).

EXAMPLE 21

(±)-(3R*,5R*)-7-Benzoyl-3-(2-methoxy-5-(5-trifluoromethyl-1H-tetrazol-1-yl)phenyl)-1-oxa-7-azaspiro[4,5]decane Prepared in an analogous fashion to Example 10 using the piperidine of Description 13.

$\delta_H$ (360MHz, DMSO-d$_6$, 353K) 1.49 (1H, m), 1.75 (4H, m), 2.19 (1H, m), 3.28 (1H, m), 3.44 (2H, m), 3.65 (3H, m), 3.92 (3H, s, ArOCH$_3$), 4.03 (2H, m), 7.23 (1H, d, J 8.7Hz, 3'-H), 7.37 (2H, m, PhH), 7.44 (3H, m, PhH), 7.57 (1H, dd, J 8.7, 2.6Hz, 4'-H), 7.62 (1H, d, J 2.6Hz, 6'-H); m/z (ES$^+$) 488 ([M+H]$^+$).

EXAMPLE 22

(±)-(3R*,5R*)-7-(2-Phenylethyl)-3-(2-methoxy-5-(5-trifluoromethyl-1H-tetrazol-1-yl)phenyl)-1-oxa-7-azaspiro[4,5]decane hydrochloride Prepared in an analogous fashion to Example 11 using the piperidine of Description 13 and (2-bromoethyl)benzene.

M.p. 187°–189° C. (IPA/Et$_2$O); $\delta_H$(360MHz, D$_2$O) 1.75–2.10 (5H, m), 2.28–2.39 (1H, m), 3.00–3.09 (2H, m), 3.10–3.22 (2H, m), 3.41–3.49 (2H, m), 3.50–3.59 (2H, m), 3.81–3.99 (2H, m), 3.99 (3H, s, ArOCH$_3$), 4.20–4.33 (1H, m), 7.25 (1H, d, J 8.8Hz, 3'-H), 7.37–7.56 (7H, m); m/z (ES$^+$) 488 ([M+H]$^+$).

EXAMPLE 23

7-Benzyl-3-(2-methoxy-5-(5-methyl-1H-1,2,4-triazol-1-yl)phenyl)-1-oxa-7-azaspiro[4,5]-dec-3-ene hydrochloride Prepared in an analogous fashion to Example 1 using the bromide of Description 15

M.p. >130° C.(amorphous solid); $\delta_H$(360MHz, D$_2$O) 1.82–2.10 (4H, m), 2.38 (3H, s, 5"—CH$_3$), 3.00–3.26 (3H, m), 3.54 (1H, m), 3.93 (3H, s, ArOCH$_3$), 4.30 (1H, br d, NCH$_A$H$_B$Ph), 4.41 (1H, d, J 13.1Hz, NCH$_A$H$_B$Ph), 4.97 (2H, m, 2—CH$_2$), 6.42 (1H, br s, 4—CH=), 7.19 (2H, m, 3'-H, 4'-H), 7.41 (1H, dd, J 8.9, 2.5Hz, 4'-H), 7.50 (5H, br s, PhH), 8.01 (1H, s, 3"-H); m/z (ES+) 417 ([M+H]$^+$).

EXAMPLE 24

7-Benzyl-3-(2-methoxy-5-(5-trifluoromethyl-1H-1,2,4-triazol-1-yl)phenyl)-1-oxa-7-azaspiro[4,5]-dec-3-ene hydrogen oxalate Prepared in an analogous fashion to Example 1 using the bromide of Description 16.

$\delta_H$ (360MHz, D$_2$O) 1.78–2.12(4H, m), 3.03 (1H, m), 3.15 (1H, d, J 12.5Hz), 3.26 (1H, d, J 12.5Hz), 3.56 (1H, m), 3.96 (3H, s, ArOCH$_3$), 4.30 (1H, d, J 13.2 Hz, NCH$_A$H$_B$Ph), 4.42 (1H, d, J 13.2Hz, NCH$_A$H$_B$Ph), 4.98 (2H, m, 2—CH$_2$), 6.44 (1H, br s, 4—CH=), 7.22 (1H, d, J 8.9Hz, 3'-H), 7.31 (1H, d, J 2.6Hz, 6'-H), 7.51 (6H, m, ArH), 8.30 (1H, s, 3"-H); m/z (ES$^+$) 471 ([M+H]$^+$).

EXAMPLE 25

7-Benzyl-3-(2-methoxy-5-(N-methyltrifluoroacetamido)-1-oxa-7-azaspiro[4,5]dec-3-ene hydrochloride Prepared in an analogous manner to Example 1 using 2-bromo-5-(N-methyltrifluoroacetamido)anisole (Desc.17).

$\delta_H$ (360MHz, D$_2$O) 1.78–2.05 (4H, m), 3.01–3.19 (3H, m), 3.27 (3H, s, N—CH$_3$), 3.50 (1H, m), 3.88 (3H, s, ArOCH$_3$), 4.29 (1H, br d, NCH$_A$H$_B$Ph), 4.40 (1H, d, J 13.0Hz, NCH$_A$H$_B$Ph), 4.97 (2H, m, 2—CH$_2$), 6.37 (1H, br s, 4-H), 7.10 (1H, d J 8.9Hz, ArH), 7.15 (1H, m, ArH), 7.31 (1H, m, ArH), 7.48 (5H, br s, PhH); m/z (ES $^+$) 461 ([M+H]$^+$).

EXAMPLE 26

7-Benzyl-3-(2-isopropoxy-5-(2-trifluoromethyl-1H-imidazol-1-yl)phenyl)-1-oxa-7-azaspiro[4,5]dec-3-ene hydrochloride Prepared in an analogous fashion to Example 1 using 1-(3-bromo-4-isopropoxyphenyl)-2-trifluoromethyl-1H-imidazole (Desc. 18).

$\delta_H$ (360 MHz, D$_2$O) 1.23 (3H, d, J 5.9Hz), 1.24 (3H, d, J 5.9Hz), 1.80–2.06 (4H, m), 3.02–3.12 (3H, m), 3.57 (1H, m), 4.19 (1H, d, J 13.1 Hz, NCH$_A$CH$_B$Ph), 4.43 (1H, d, J 13.2 Hz, NCH$_A$CH$_B$Ph), 4.80–4.91 (2H, m, 2—CH$_2$), 6.28 (1H, s, 4-H), 7.00 (1H, d, J 9.0 Hz, 3'-H), 7.12 (1H, m, ArH), 7.18 (1H, d, J 1.15Hz, imidazole-H), 7.20–7.24 (2H, m, ArH, imidazole-H), 7.37–7.44 (5H, m, Ph-H); m/z (ES$^+$) 498 ([M+H]$^+$).

EXAMPLE 27

7-Benzyl-3-(2-methoxy-5-(5-trifluoromethyl-1H-tetrazol-1-yl)methylphenyl)-1-oxa-7-azaspiro[4,5]dec-3-ene hydrochloride Prepared in an analogous fashion to Example 1 using the bromide of Description 19.

$\delta_H$(360 MHz, D$_2$O) 1.72–2.14 (4H, m), 3.01–3.23 (3H, m), 3.56 (1H, m), 3.91 (3H, s, ArOCH$_3$), 4.25 (1H, d, J 13.2 Hz, NCH$_A$CH$_B$Ph), 4.40 (1H, d, J 13.2 Hz, NCH$_A$CH$_B$Ph), 4.88–4.97 (2H, m, 2-CH$_2$), 5.26–5.33 (2H, m), 6.39 (1H, s, 4-H), 7.18 (1H, d, 8.7 Hz, 3'-H), 7.29 (1H, d, J 2.1 Hz, 6'-H), 7.46 (5 H, s, Ph-H), 7.55 (1H, dd, J8.7, 2.1 Hz, 4'-H); m/z (ES$^+$) 486 ([M+H]$^+$).

EXAMPLE 28

(±)-(3R*, 5R*)-7-Benzyl-3-(2-methoxy-5-(2-trifluoromethyl-1H-imidazol-1-yl)phenyl)-1-oxa-7-azaspiro[4,5]decane hydrogen oxalate Prepared in an analogous fashion to Example 11 using the piperidine of Desprition 20 and benzyl bromide.

(Found: C, 59.38; H, 5.11; N, 7.12. C$_{26}$H$_{28}$F$_3$N$_3$O$_2$.C$_2$H$_2$O$_4$. 0.25H$_2$O requires C, 59.41; H, 5.43; N, 7.42%); $\delta_H$ (360 MHz, D$_2$O) 1.68 (1H, m), 1.80–2.07 (4H, m), 2.25 (1H, m), 2.98 (2H, m), 3.40 (1H, br d, J 12.6 Hz), 3.52 (1H, m), 3.76 (1H, m), 3.87 (1H, m), 3.89 (3H, s, ArOCH$_3$), 4.13 (1H, m), 4.29 (1H, d, J13.2 Hz, NCH$_A$H$_B$Ph), 4.41 (1H, d, J 13.2 Hz, NCH$_A$H$_B$Ph), 7.12 (1H, d, J 8.7 Hz, 3'-H), 7.23 (1H, d, J 1.1 Hz, imidazole H), 7.35 (3H, m, ArH), 7.54 (5H, m, PhH); m/z (ES$^+$) 472 ([M+H]$^+$).

EXAMPLE 29

(±)-(3R*, 5R*, 11R*/S*)-3-(2-Methoxy-5-(2-trifluoromethyl-1H-imidazol-1-yl)phenyl)-7-(1-phenyl)ethyl-1-oxa-7-azaspiro[4,5]decane hydrochloride Prepared in an analogous fashion to Example 11 using the piperidine of Description 20 and 1-bromoethylbenzene.

$\delta_H$(360 MHz, $D_2O$) 1.63–2.27 (8H, m), 2.80–2.95 (2H, m), 3.40–3.94 (7H, m), 4.18 (1H, m), 4.58 (1H, m), 7.15 (1H, dd J 8.7, 3.2 Hz, 4'-H), 7.26 (1H, d, J 1.2 Hz, imidazole-H), 7.37–7.41 (3H, m, ArH), 7.58 (5H, s, PhH): m/z (ES$^-$) 486 ([M+H]$^+$).

EXAMPLE 30

(±)-(3R*, 5R*)-3-(2-Methoxy-5-(2-trifluoromethyl-1H-imidazol-1-yl)phenyl)-7-(2-phenyl)ethyl-1-oxa-7-azaspiro[4,5]decane hydrochloride Prepared in an analogous fashion to Example 11 using the piperidine of Description 20 and 2-bromoethylbenzene.

$\delta_H$ (360 MHz, $D_2O$) 1.71–2.10 (5H, m), 2.27 (1H, m), 3.00–3.17 (4H, m), 3.39–3.55 (4H, m), 3.86–3.88 (2H, m), 3.92 (3H, s, ArOCH$_3$), 4.24 (1H, m), 7.14 (1H, m, ArH), 7.23 (1H, d, J 1.2 Hz, imidazole-H), 7.35 7.43 (8H, m, ArH); m/z (ES$^+$) 4.86 ([M+H]$^+$).

EXAMPLE 31

(±)-(3R*, 5R*)-3-(2-Methoxy-5-(2-trifluoromethyl-1H-imidazol-1-yl)phenyl)-7-phenylacetyl-1-oxa-7-azaspiro[4,5]decane Prepared in an analogous fashion to Example 10 using the piperidine of Description 20 and phenylacetyl chloride.

$\delta_H$(360 MHz, CDCl$_3$; mixture of rotamers) 1.18–1.80 (9H, m), 1.90–1.99 and 2.14–2.19 (1H, dd, J 12.4, 7.8 Hz), 3.21–4.27 (10H, m), 6.82 (1H, m), 7.03–7.25 (9H, m); m/z (ES$^+$) 500 ([M+H]$^+$).

EXAMPLE 32

(±)-3R*, 5R*)-7-(2-Oxo-2-phenyl)ethyl-3-(2-methoxy-5-(2-trifuloromethyl-1H-imidazol-1-yl)phenyl)-1-oxa-7-azaspiro[4,5]decane hydrogen oxalate Prepared in an analogous fashion to Example 11 using the piperidine of Description 20 and phenacyl bromide.

$\delta_H$(360 MHz, $D_2O$) 1.82 (2H, m), 1.93 (2H, m), 2.10 (1H, m), 2.22 (1H, m), 3.03 (1H, m), 3.22 (1H, m), 3.48 (1H, m), 3.68 (1H, m), 3.84 (4H, m), 3.97 (1H, m), 4.39 (1H, m), 4.81 (1H, d, J 17.9 Hz, NCH$_A$H$_B$COPh), 4.97 (1H, d, J 17.9 Hz, NCH$_A$H$_B$COPh), 7.07 (1H, d J9.4 Hz, 3'-H), 7.17 (1H, d, J 1.0 Hz, imidazole H), 7.33 (3H, m ArH), 7.54 (2H, m, ArH), 7.71 (1H, t, J 7.5 Hz, ArH), 7.93 (2H, d, J 7.5 Hz, ArH): m/z (ES$^+$) 500 ([M+H]$^+$).

EXAMPLE 33

(±)-(3R*, 5R*, 12S*/R*)-7-(2-Hydroxy-2-phenyl)ethyl-3-(2-methoxy-5-(2-trifluoromethyl-1H-imidazol-1-yl)phenyl)-1-oxa-7-azaspiro[4,5]decane hydrogen oxalate Sodium borohydride (12 mg, 0.32 mmol) was added to a solution of (±)-(3R*, 5R*)-7-phenacyl-3-(2-methoxy-5-(2-trifluoromethyl-1H-imidazol-1-yl)phenyl)-1-oxa-7-azaspiro[4,5]decane (105.9 mg, 0.212 mmol) in ethanol (2 ml) and the mixture stirred at room temperature for 4 hours. The mixture was poured into water (50 ml) and extracted with ethyl acetate (2×20 ml). The extracts were washed with brine (20 ml), combined, dried (MgSO$_4$) and concentrated. The residue was purified by flash chromatography, eluting with 5% then 7.5% methanol in dichloromethane to give (±)-(3R*, 5R*, 12S*/R*)-7-(2-hydroxy-2-phenylehtyl)-3-(2-methoxy-5-(2-trifluoromethyl-1H-imidazol-1-yl)phenyl)-1-oxa-7-azaspiro[4,5]decane (86.0 mg, 81%). The free base was dissolved in ether and treated with oxalic acid (15.7 mg) in ether. The resulting precipitate was collected under suction, washed with ether and dried in vacuo to afford the title compound (75.1 mg); (Found: C, 58.89; H, 5.11; N, 6.87. $C_{27}H_{30}F_3N_3O_3 \cdot C_2H_2O_4$ requires C, 58.88; H, 5.45; N, 7.10%; $\delta_H$ (360 MHz, $D_2O$) 1.72–2.37 (6H, m), 3.11 (2H, m), 3.34–3.96 (10H, m), 4.27 (1H, m), 5.25 (1H, m), 7.13 (1H, d, J 9.3 Hz, 3'-H), 7.22 (1H, br s, imidazole H), 7.36 (3H, m, ArH), 7.47 (5H, m, ArH); m/z (ES$^+$) 502 ([M+H]$^+$).

EXAMPLE 34

(±)-(3R*, 5R*, 11S*/R*)-3-(2-Methoxy-5-(2-trifluoromethyl-1H-imidazol-1-yl)phenyl)-7-(1-methyl-2-phenyl)ethyl-1-oxa-7-azaspiro[4,5]decane hydrochloride Prepared in an analogous fashion to Example 11 using the piperdine of Description 20 and 2-bromo-1-phenylpropane.

$\delta_H$ (360 MHz, $D_2O$) 0.74–0.81 (3H, m), 1.55 (1H, m), 1.79–2.31 (7H, m), 2.62–2.94 (2H, m), 3.40–3.60 (2H, m), 3.88–3.91 (5H, m), 4.11–4.28 (2H, m), 7.11–7.13 (1H, m), 7.22 (1H, d, J 1.2 Hz, imidazole-H), 7.33–7.37 (3H, m), 7.54 (5H, m): m/z (ES$^+$) 500 ([M+H]$^+$).

EXAMPLE 35

(±)-(3R*, 5R*)-7-(Indan-2-yl)-3-(2-methoxy-5-(2-trifluoromethyl-1H-imidazol-1-yl)phenyl)-1-oxa-7azaspiro[4,5]decane (±)-(3R*, 5R*)-3-(2-Methoxy-5-(2-trifluoromethyl-1H-imidazol-1-yl)phenyl)-1-oxa-7-azaspiro[4,5]-decane (free base of Desc.20; 180 mg, 0.47 mmol) and indan-2-one (75 mg, 0.57 mmol) were stirred at reflux in toluene (20 ml) for 18 hours, under Dean-Start conditions. The mixture was concentrated in vacuo then redissolved in methanol (30 ml) and glacial acetic acid (1 ml). Sodium cyanoborohydride (35 mg, 0.55 mmol) was added portionwise. The mixture was stirred at room temperature for 72 hours, concentrated in vacuo and the residue partitioned between 2N NaOH and ethyl acetate. The organic layer was separated, dried (MgSO$_4$), filtered and concentrated. Chromatography on silica gel eluting with 120:8:1 dichloromethane:methanol:ammonia gave the title compound as a tan solid (22 mg); $\delta_H$ (360 MHz CDCl$_3$) 1.58–1.95 (7H, m), 2.48 (4H, m), 2.99–3.22 (4H, m), 3.73–3.82 (2H, m), 3.91 (3H, s, ArOCH$_3$), 4.27 (1H, m), 6.90 (1H, d, J 8.6 Hz, 3'-H), 7.11–7.26 (8H, m, ArH); m/z (ES$^+$) 498 ([M+H]$^+$).

EXAMPLE 36

(3R, 5R, 11S)-7-(1-Methyl-2-phenyl)ethyl-3-(2-methoxy-5-(5-trifluoromethyl-1H-tetrazol-1-yl)phenyl)-1-oxa-7-azaspiro[4,5]decane hydrochloride and (3S, 5S, 11S)-7-(1-methyl-2-phenyl)ethyl-3-(2-methoxy-5-(5-trifluoromethyl-1H-tetrazol-1-yl)phenyl)-1-oxa-7-azaspiro[4,5]decane hydrochloride A mixture of (±)-(3R*, 5R*)-3-(2-methoxy-5-(5-trifluoromethyl-1H-tetrazol-1-yl)phenyl)-1-oxa-7-azaspiro[4,5]decane (Desc. 13; 167.0 mg, 0.436 mmol), (2R)-1-phenyl-2-(ρ-toluenesulfonyloxy)propane (Desc.21; 238.6 mg, 0.822 mmol) and potassium carbonate (186.8 mg, 1.35 mmol) in dimethylformamide (4 ml) was stirred at room temperature overnight (24 hours). Further portions of (2R)-1-phenyl-2-(ρ-toluenesulfonyloxy)propane (231.5 mg, 0.797 mmol) and potassium carbonate (182.1 mg, 1.32 mmol) were added and the mixture stirred at 60° C. for 24 hours. Finally, more (2R)-1-phenyl-2-(ρ-toluensulfonyloxy) propane (128.2 mg, 0.442 mmol) was added and the mixture stirred at 80° C. for 5 hours. The reaction mixture was poured into water (50 ml) and extracted with ethyl acetate (2×25 ml). The extracts were washed with brine (50 ml), combined, dried (MgSO$_4$) and concentrated. The residue was purified by flash chromatography, eluting with 1:2 then 1:1 ethyl acetate/hexane, to give a partial separation of the two diastereoisomers. These were further purified by preparative layer chromatography and the hydrochloride salts prepared to afford the title compounds, diastereoisomer A (20.1 mg); $[\alpha]_D$ −9° (c 1.0, MeOH); (found: C, 57.13; H, 5.69; N, 12.56 $C_{26}H_{31}ClF_3N_5O_2.0.5H_2O$ requires C, 57.09; H, 5.90; N, 12.80%); $\delta_H$ (500 MHz, $D_2O$) 1.30 (3H, d, J 6.7 Hz, CHCH$_3$), 1.82 (2H, m), 2.03 (3H, m), 2.39 (1H, m), 2.86 (1H, m), 3.21 (2H, m), 3.30 (1H, m), 3.51 (2H, m), 3.67 (1H, m), 3.95 (2H, m), 3.98 (3H, s, ArOCH$_3$), 4.28 (1H, m), 7.27 (1H, d, J 8.8 Hz, 3'-H), 7.38 (3H, m, ArH), 7.45 (2H, m, ArH), 7.55 (2H, m, ArH); m/z (ES$^+$) 502 ([M+H]$^+$) and diastereoisomer B (17.7 mg); $[\alpha]_D$+19° (c 1.0 MeOH); (Found: C, 56.25; H, 5:62; N, 12.16. $C_{26}H_{31}ClF_3N_5O_2.H_2O$ requires C, 56.16; H, 5.98; N, 12.60%); $\delta_H$ (500 MHz, $D_2O$) 1.14 (3H, d, J 6.7 Hz, CHCH$_3$), 1.66 (2H, m), 1.78 (1H, m), 1.91 (2H, m), 2.24 (1H, m), 2.84 (1H, m), 3.05 (3H, m), 3.22 (1H, br d, J 10.7 Hz), 3.35 (1H, d, J 12.4 Hz), 3.56 (1H, m), 3.79 (2H, m), 3.84 (3H, s, ArOCH$_3$), 4.13 (1H, m), 7.12 (1H, d, J 8.8 Hz, 3'-H), 7.24 (3H, m, ArH), 7.31 (2H, m, ArH), 7.49 (2H, m, ArH); m/z (ES$^+$) 502 ([M+H]$^+$).

EXAMPLE 37

(3R, 5R, 11R)-7-(1-Methyl-2-phenyl)ethyl-3-(2-methoxy-5-(5-trifluoromethyl-1H-tetrazol-1-yl)phenyl)-1-oxa-7-azaspiro[4,5]decane hydrochloride and (3S, 5S, 11R)-7-(1-methyl-2-phenyl)ethyl-3-(2-methoxy-5-(5-trifluoromethyl-1H-tetrazol-1-yl)phenyl)-1-oxa-7-azaspiro[4,5]decane hydrochloride Prepared in an analogous manner to Example 36, using (2S)-1-phenyl-2-(ρ-toluenesulfonyloxy)propane (prepared as Description 21).

Diastereoisomer A: $[\alpha]_D$ +10° (c 1.0, MeOH); (Found: C, 57.22; H, 5.57; N, 12.64. $C_{26}H_{31}ClF_3N_5O_2.0.5H_2O$ requires C, 57.09; H, 5.90; N, 12.80%); $\delta_H$ (360 MHz, CD$_3$OD) 1.26 (3H, d, J 6.2 Hz, CHCH$_3$), 1.76 (1H, m), 1.89 (2H, m), 2.04 (1H, m), 2.17 (1H, m), 2.38 (1H, m), 2.73 (1H, m), 3.19 (2H, m), 3.30–3.56 (4H, m), 3.96 (2H, m), 3.99 (3H, s, ArOCH$_3$), 4.31 (1H, m), 7.23–7.38 (6H, m, ArH), 7.52 (2H, m, ArH): m/z (ES$^+$) 502 ([M+H]$^+$).

Diastereoisomer B: $[\alpha]_D$ −16° (c 1.0, MeOH); (Found: C, 56.71; H 5.78; N, 12.41. $C_{26}H_{31}ClF_3N_5O_2.0.7H_2O$ requires C, 56.71; H, 5.93; N. 12.72%): $\delta_H$ (500 MHz, CD$_3$OD) 1.26 (3H, d, J 6.4 Hz, CHCH$_3$), 1.77 (1H, m), 1.92 (2H, m), 2.07 (1H, m), 2.26 (1H, m), 2.42 (1H, m), 2.94 (1H, m), 3.21 (3H, m), 3.36 (1H, m), 3.51 (1H, m), 3.61 (1H, m), 3.98 (2H, m), 4.02 (3H, s, ArOCH$_3$), 4.35 (1H, m), 7.27 (1H, d, J 8.7 Hz, 3'-H), 7.33 (3H, m, ArH), 7.39 (2H, m, ArH), 7.54 (1H, dd, J 8.7, 2.6 Hz, 4'-H), 7.58 (1H, d, J 2.6 Hz, 6'-H); m/z (ES$^+$) 502 ([M+H]$^+$).

EXAMPLE 38

(±)-(3R*, 5R*)-7-Benzyl-3-(2-methoxy-5-(3-trifluoromethyl-4H-1,2,4-triazol-4-yl)phenyl)-8-oxo-1-oxa-7-azaspiro[4,5]decane A mixture of (±)-(3R*, 5R*)-3-(2-methoxy-5-(3-trifluoromethyl-4H-1,2,4-triazol-4-yl)phenyl)-1-oxa-7-azaspiro[4,5]decane and (±)-(3R*, 5R*)-3-(2-methoxy-5-(3-trifluoromethyl-4H-1,2,4-triazol-4-yl)phenyl)-1-oxa-7-azaspiro[4,5]dec-3-ene [1.5:1 ratio; prepared by hydrogenation 7-benzyl-3-(2-methoxy-5-(3-trifluoromethyl-4H-1,2,4-triazol-4-yl)phenyl)-1-oxa-7-azaspiro[4,5]-dec-3-ene (Ex. 7) in an analogous manner to Desc. 12] (295.9 mg, 0.706 mmol) in dichloromethane (10 ml) was treated with triethylamine (0.30 ml, 2.15 mmol) and acetyl chloride (0.06 ml, 0.84 mmol). The mixture was stirred at room temperature for 20 hours, diluted with dichloromethane (10 ml) and washed with 1 M hydrochloric acid (40 ml) then saturated sodium hydrogen carbonate (40 ml). The dichloromethane phase was dried (MgSO$_4$) and concentrated in vacuo to afford a crude mixture of acetyl piperidines; m/z (ES$^+$) 425 ([M+H]$^+$). This mixture was dissolved in ethyl acetate (10 ml) and treated with 10% aqueous sodium periodate (10 ml) and ruthenium (IV) oxide hydrate (10 mg). The reaction mixture was stirred at room temperature for 4.5 hours, the phases separated and the aqueous phase extracted with ethyl acetate (10 ml). The organic extracts were combined and stirred with 2-propanol (10 ml) for 3 hours. The mixture was filtered and concentrated in vacuo. The residue was dissolved in ethyl acetate (20 ml), diluted with hexane (10 ml) and stirred with basic alumina overnight. The mixture was filtered and the alumina washed with dichloromethane followed by 10% methanol in dichloromethane. The filtrate was evaporated and the residue purified by preparative layer chromatography, eluting with 5% methanol in dichloromethane, to afford a mixture of piperidones (34.6 mg); m/z (ES$^+$) 397 ([M+H]$^+$). This material was dissolved in THF (5 ml) and treated successively with 1.0 M sodium bis(trimethylsilyl)amide in THF (0.11 ml, 0.11 mmol) and benzyl bromide (12 μl, 0.10 mmol). The mixture was stirred at roo temperature for 3 hours, at reflux for 2 hours and then at room temperature overnight. The reaction mixture was poured into water (50 ml) and extracted with ethyl acetate (2×25 ml). The extracts were combined, dried (MgSO$_4$), concentrated and the residue purified by preparative layer chromatography, eluting five times with 2.5% methanol in dichloromethane, to afford the title compound (14.2 mg); $\delta_H$ (360 MHz, CDCl$_3$) 1.83 (1H, dd, J 12.8, 8.8 Hz, 4-H$_a$), 1.95 (2H, m, 10-H$_a$, 10-H$_b$), 2.22 (1H, dd, J 12.8, 8.2 Hz, 4-H$_b$), 2.48 (1H, dt, J 17.8, 6.1 Hz, 9-H$_a$), 2,75 (1H, m, 9-H$_b$), 3.18 (1H, d, J12,4 Hz, 6-H$_a$), 3.27 (1H, d, J 12.4 Hz, 6-H$_b$), 3.71 (1H, m, 3-H), 3.82 (1H, apparent t, J 8 Hz, 2-H$_a$), 3.89 (3H, s, ArOCH$_3$), 4.12 (1H, dd, J 8.7, 7.1 Hz, 2-H$_b$), 4.57 (1H, d, J 14.8 Hz, NCH$_A$H$_B$Ph), 4.66 (1H, d, J 14.8 Hz, NCH$_A$H$_B$Ph), 6.95 (1H, d, J 8.5 Hz, 3'-H), 7.18–7.36 (7H, m, ArH), 8.29 (1H, s, triazole H); m/z (ES$^+$) 487 ([M+H]$^+$).

What is claimed is:

1. A compound of the formula (I):

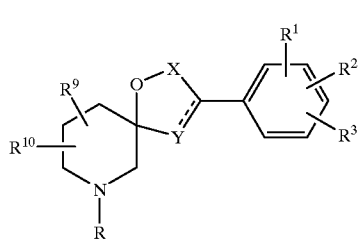

(I)

wherein

R represents $C_{1-6}$alkyl, $C_{2-6}$alkenyl, $C_{2-6}$alkynyl, $C_{3-7}$cycloalkyl, $C_{3-7}$cycloalkyl$C_{1-4}$alkyl, which groups are optionally substituted by a group selected from hydroxy, $C_{1-4}$alkoxy or NR$^a$R$^b$, where R$^a$ and R$^b$ each independently represent hydrogen or $C_{1-4}$alkyl;

or R represents a $C_{1-4}$alkyl group substituted by the group Ar, and optionally further substituted by one or both of the groups R$^4$ and R$^5$;

R$^1$ represents hydrogen, hydroxy, $C_{1-6}$alkyl, $C_{2-6}$alkenyl, $C_{2-6}$alkynyl, $C_{3-7}$cycloalkyl, $C_{3-7}$cycloalkyl$C_{1-4}$alkyl, $C_{1-6}$alkoxy, fluroro$C_{1-6}$alkyl, fluoro$C_{1-6}$alkoxy, hydroxy$C_{1-4}$alkyl, $C_{1-6}$alkoxy$C_{1-4}$alkyl, $C_{1-6}$alkoxy$C_{1-4}$alkoxy, fluoro$C_{1-6}$alkoxy$C_{1-4}$alkyl, $C_{2-6}$alkenyloxy, $C_{3-7}$cycloalkoxy, $C_{3-7}$cycloalkyl$C_{1-4}$alkoxy, phenoxy, benzyloxy, cyano, halogen, trimethylsilyl, nitro, $NR^aR^b$, $SR^a$, $SOR^a$, $SO_2R^a$, $OSO_2R^a$, $COR^a$, $CO_2R^a$, $CONR^aR^b$, $SO_2NR^aR^b$, or $OC_{1-4}$alkyl$NR^aR^b$, where $R^a$ and $R^b$ each independently represent hydrogen, $C_{1-4}$alkyl or fluoro$C_{1-4}$alkyl;

$R^2$ represents hydrogen, halogen, $C_{1-6}$alkyl or $C_{1-6}$alkoxy;

or when $R^2$ is adjacent to $R^1$, they may be joined together such that there is formed a 5- or 6-membered saturated or unsaturated ring containing one or two atoms selected from nitrogen, oxygen and sulphur, which ring is optionally substituted by a group selected from $C_{1-4}$alkyl, $CF_3$, =O or =S;

$R^3$ represents hydrogen, halogen, $C_{1-6}$alkyl, $C_{2-6}$alkenyl, $C_{2-6}$alkynyl, fluoro$C_{1-6}$alkyl, $C_{1-6}$alkoxy, fluoro$C_{1-6}$alkoxy, $C_{3-7}$cycloalkyl, $C_{3-7}$cycloalkyl$C_{1-4}$alkyl, hydroxy, phenoxy, benzyloxy, trimethylsilyl, nitro, cyano, $SR^a$, $SOR^a$, $SO_2R^a$, $NR^aR^b$, $COR^a$, $CO_2R^a$, $CONR^aR^b$, $SO_2NR^aR^b$, $OC_{1-4}$alkyl$NR^aR^b$, $NR^aCOR^d$, or $C_{1-4}$alkyl substituted by a $C_{1-4}$alkoxy, hydroxy, cyano or $CO_2R^a$ group, where $R^a$ and $R^b$ are as previously defined and $R^d$ is $C_{1-6}$alkyl, $C_{1-6}$alkoxy, fluoro$C_{1-6}$alkyl or phenyl;

or $R^3$ represents a 5-or 6-membered aromatic heterocyclic group containing 1, 2, 3 or 4 heteroatoms, selected from nitrogen, oxygen and sulphur, which group is optionally substituted by one or two groups selected from $C_{1-6}$alkyl, $C_{1-6}$alkoxy, $C_{3-7}$cycloalkyl, $C_{3-7}$cycloalkyl$C_1$_alkyl, trifuloromethyl, $OCF_3$, $NO_2$, CN, $SR^a$, $SOR^a$, $SO_2R^a$, $COR^a$, $CO_2R^a$, phenyl, $—(CH_2)_rNR^aR^b$, $—(CH_2)_rNR^aCOR^b$, $—(CH_2)_rCONR^aR^b$, or $CH_2C(O)R^a$, where $R^a$ and $R^b$ are each independently hydrogen or $C_{1-4}$alkyl and r is zero, 1 or 2;

$R^4$ and $R^5$ each independently represent hydroxy, $C_{1-4}$alkyl, $C_{1-4}$alkoxy$C_{1-4}$alkyl, hydroxy$C_{1-4}$alkyl, or $C_{1-4}$alkyl$NR^aR^b$ where $R^a$ and $R^b$ are each independently hydrogen or $C_{1-4}$alkyl, or together $R^4$ and $R^5$ represent an oxo group or when $R^4$ and $R^5$ are attached to the same carbon atom, they may be joined together to form a $C_{3-5}$cycloalkyl ring;

Ar represents phenyl optionally substituted by one or two substituents selected from halogen, $C_{1-6}$alkyl, $C_{1-6}$alkoxy, $CF_3$, $OCF_3$, $NO_2$, CN, $SR^a$, $SOR^a$, $SO_2R^a$, $COR^a$, $CO_2R^a$, $(CH_2)_rCONR^aR^b$, $(CH_2)_rNR^aR^b$ or $(CH_2)_rNR^aCOR^b$, where $R^a$ and $R^b$ are independently hydrogen or $C_{1-4}$alkyl and r is zero, 1 or 2;

or Ar represents a 5-membered or 6-membered heterocyclic ring containing 1, 2 or 3 nitrogen atoms optionally substituted by =O or =S and optionally substituted by a group of the formula $ZNR^7R^8$ where Z is $C_{1-6}$alkylene or $C_{3-6}$cycloalkyl;

$R^7$ is hydrogen or $C_{1-4}$alkyl, $C_{3-7}$cycloalkyl, $C_{3-7}$cycloalkyl$C_{1-4}$alkyl, or $C_{2-4}$alkyl substituted by $C_{1-4}$alkoxy or hydroxyl;

$R^8$ is hydrogen or $C_{1-4}$alkyl, $C_{3-7}$cycloalky, $C_{3-7}$cycloalkyl$C_{1-4}$alkyl, or $C_{2-4}$alkyl substituted by $C_{1-4}$alkoxy, hydroxyl or a 4, 5 or 6 membered heteroaliphatic ring containing one or two heteroatoms selected from N, O and S;

or $R^7$, $R^8$ and the nitrogen atom to which they are attached form a heteroliphatic ring of 4 to 7 ring atoms, optionally substituted by one or two groups selected from hydroxy or $C_{1-4}$alkoxy optionally substituted by a $C_{1-4}$alkoxy or hydroxyl group, and optionally containing a double bond, which ring may optionally contain an oxygen or sulphur ring atom, a group S(O) or $S(O)_2$ or a second nitrogen atom which will be part of a NH or $NR^c$ moiety where $R^c$ is $C_{1-4}$alkyl optionally substituted by hydroxy or $C_{1-4}$alkoxy;

or $R^7$, $R^8$ and the nitrogen atom to which they are attached form a non-aromatic azabicyclic ring system of 6 to 12 ring atoms;

or Z, $R^7$ and the nitrogen atom to which they are attached form a heteroalphatic ring to 4 to 7 ring atom which may optionally contain an oxygen ring atom;

$R^9$ and $R^{10}$ each independently represent hydrogen, halogen, $C_{1-6}$alkyl, $CH_2OR^e$, oxo, $CO_2R^a$ or $CONR^aR^b$ where $R^a$ and $R^b$ are as previously defined and $R^e$ represents hydrogen, $C_{1-6}$alkyl or phenyl;

X represents $—CH_2$, or $—CH_2CH_2—$;

Y represents $—CH=$, $—CH_2—$, $—CH_2CH=$ or $—CH_2CH_2—$, with the proviso that the sum total of carbon atoms in X+Y is 2 or 3; and when Y is $—CH=$ or $—CH_2CH=$, the broken line represents a double bond;

or a pharmaceutically acceptable salt thereof.

2. A compound as claimed in claim 1 wherein $R^1$ is hydrogen, $C_{1-6}$alkyl, $C_{1-6}$alkoxy, fluoro$C_{1-6}$alkoxy, $C_{3-7}$cycloalkoxy, halogen or $NR^aR^b$.

3. A compound as claimed in claim 1 wherein $R^2$ is a hydrogen, fluorine or chlorine atom.

4. A compound as claimed in claim 1 wherein $R^3$ is halogen, $C_{1-6}$alkyl, flupor$C_{1-6}$alkyl, $C_{1-6}$alkoxy, fluoro$C_{1-6}$alkoxy, cyano or a 5-membered aromatic heterocyclic group as defined in claim 1.

5. A compound as claimed in claim 1 wherein R represents a $C_{1-4}$alkyl group substituted by the group Ar, and optionally substituted by one or both of the groups $R^4$ and $R^5$.

6. A compound as claimed in claim 1 wherein $R^4$ is $C_{1-4}$alkyl, or $R^4$ and $R^5$ together represent an oxo group.

7. A compound as claimed in claim 1 wherein Ar represents a phenyl ring, optionally substituted by one or two halogen atoms or $C_{1-4}$alkoxy, or Ar represents a pyridyl group.

8. A compound as claimed in claim 1 wherein $R^9$ and $R^{10}$ are both hydrogen atoms.

9. A compound as claimed in claim 1 wherein X is $—CH_2—$, and Y is $—CH_2—$ or $—CH=$.

10. A compound as claimed in claim 1 of the formula (Ib) or a pharmaceutically acceptable salt thereof:

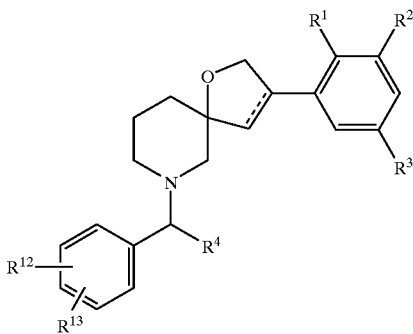

(Ib)

wherein, $R^1$, $R^2$, $R^3$ and $R^4$ are as defined in in claim 1, the broken line is an optional double bond, and $R^{12}$ and $R^{13}$ are each independently hydrogen, halogen or $C_{1-6}$alkoxy.

11. A compound as claimed in claim 1 of the formula (Ic) or a pharmaceutically acceptable salt thereof:

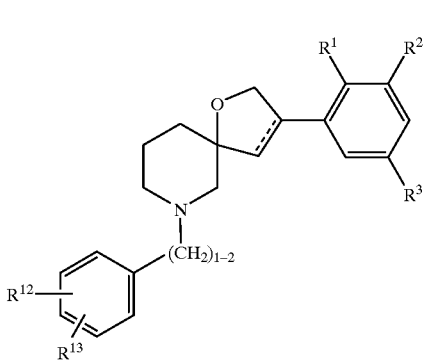

(Ic)

wherein $R^1$, $R^2$ and $R^3$ are defined in claim 1, the broken line is an optional double bond, and $R^{12}$ and $R^{13}$ are each independently hydrogen, halogen or $C_{1-6}$alkoxy.

12. A compound as claimed in claim 1 wherein

R represents $C_{1-6}$alkyl, $C_{3-7}$cycloalkyl or $C_{3-7}$cycloalkyl$C_{1-4}$alkyl;

or R represents a $C_{1-4}$alkyl group substituted by the group Ar, and optionally further substituted by one or both of the groups $R^4$ and $R^5$;

$R^1$ represents $C_{1-6}$alkoxy, fluoro$C_{1-6}$alkoxy, $C_{1-6}$alkoxy$C_{1-4}$alkoxy, $C_{2-6}$alkenyloxy, $C_{3-7}$cycloalkoxy or $C_{3-7}$cycloalkyl$C_{1-4}$alkoxy;

$R^2$ represents hydrogen;

$R^3$ represents hydrogen, $C_{1-6}$alkoxy, fluoro$C_{1-6}$alkoxy, phenoxy, benzyloxy, cyano, or $NR^aCOR^d$, where $R^a$ and $R^b$ each independently represent hydrogen, $C_{1-4}$alkyl or fluoro$C_{1-4}$alkyl and $R^d$ is $C_{1-6}$alkyl, $C_{1-6}$alkoxy, fluoro$C_{1-6}$alkyl or phenyl;

or $R^3$ represents a 5-membered aromatic heterocyclic group containing 2, 3 or 4 nitrogen atoms, which group is optionally substituted by a group selected from $C_{1-6}$alkyl or trifluoromethyl;

$R^4$ and $R^5$ each independently represent hydroxy, $C_{1-4}$alkyl, or together $R^4$ and $R^5$ represent an oxo group;

Ar represents phenyl optionally substituted by one or two substituents selected from halogen, $C_{1-4}$alkyl, $C_{1-6}$alkoxy or $CF_3$;

or Ar represents a 5-membered or 6-membered heterocyclic ring containing 1, 2 or 3 nitrogen atoms optionally substituted by a group of the formula $ZNR^7R^8$:

$R^7$ is hydrogen or $C_{1-4}$alkyl;

$R^8$ is hydrogen or $C_{1-4}$alkyl;

$R^9$ and $R^{10}$ each represent hydrogen;

X represents —$CH_2$;

Y represents —CH═, or —$CH_2$—;

Z is $C_{1-3}$alkylene; and when Y is —CH═ the broken line represents a double bond:

or a pharmaceutically acceptable salt thereof.

13. A compound selected from:

7-benzyl-3-(2-methoxyphenyl)-1-oxa-7-azaspiro[4,5]dec-3-ene;

7-benzyl-3-(2-methoxy-5-(5-trifluoromethyl-1H-tetrazol-1-yl)phenyl)-1-oxa-7-azaspiro[4,5]dec-3-ene;

7-benzyl-3-(2-methoxy-5-(1H-tetrazol-1-yl)phenyl)-1-oxa-7-azaspiro[4,5]dec-3-ene;

7-benzyl-3-(2-methoxy-5-(4-pyridyl)phenyl)-1-oxa-7-azaspiro[4,5]dec-3-ene;

7-benzyl-3-(2-methoxy-5-cyanophenyl)-1-oxa-7-azaspiro[4,5]dec-3-ene;

7-benzyl-3-(2-methoxy-5-trifluoromethoxyphenyl)-1-oxa-7-azaspiro[4,5]dec-3-ene;

7-benzyl-3-(2-methoxy-5-(3-trifluoromethyl-4H-1,2,4-triazol-4-yl)phenyl)-1-oxa-7-azaspiro[4,5]-dec-3-ene;

7-benzyl-3-(2-methoxy-5-(2-trifluoromethyl-1H-imidazol-1-yl)phenyl)-1-oxa-7-azaspiro[4,5]-dec-3-ene;

7-benzyl-3-(2-methoxy-5-benzyloxyphenyl)-1-oxa-7-azaspiro[4,5]dec-3-ene;

7-benzoyl-3-(2-methoxy-5-(5-trifluoromethyl-1H-tetrazol-1-yl)phenyl)-1-oxa-7-azaspiro[4,5]dec -3-ene;

7-(3,4-dichlorobenzyl)-3-(2-methoxy-5-(5-trifluoromethyl-1H-tetrazol-1-yl)phenyl)-1-oxa-7-azaspiro[4,5]dec-3-ene;

7-(4-pyridiyl)-3-(2-methoxy-5-(5-trifluoromethyl-1H-tetrazol-1-yl)phenyl)-1-oxa-7-azaspiro[4,5]dec-3-ene;

7-(2-pyridyl)-3-(2-methoxy-5-(5-trifluoromethyl-1H-tetrazol-1-yl)phenyl)-1-oxa-7-azaspiro[4,5]dec-3-ene;

7-(2-methoxybenzyl)-3-(2-methoxy-5-(5-trifluoromethyl-1H-tetrazol-1-yl)phenyl)-1-oxa-7-azaspiro[4,5]dec-3-ene;

7-(1-phenylethyl)-3-(2-methoxy-5-(5-trifluoromethyl-1H-tetrazol-1-yl)phenyl)-1-oxa-7-spiro[4,5]dec-3-ene;

7-(2-phenylethyl)-3-(2-methoxy-5-(5-trifluoromethyl-1H-tetrazol-1-yl)phenyl)-1-oxa-7-azaspiro[4,5]dec-3-ene;

7-cyclohexylmethyl-3-(2-methoxy-5-(5-trifluoromethyl-1H-tetrazol-1-yl)phenyl)-1-oxa-7-azaspiro[4,5]dec-3-ene;

7-(5-dimethylaminomethyl-1H-1,2,3-triazol-4-yl)methyl-3-(2-methoxy-5-(5-trifluoromethyl-1H-tetrazol-1-yl)phenyl)-1-oxa-7-azaspiro[4,5]dec-3-ene;

(±)-(3R*, 5R*)-7-benzyl-3-(2-methoxy-5-(5-trifluoromethyl-1H-tetrazol-1-yl)phenyl)-1-oxa-7-azaspiro[4,5]decane;

(±)-(3S*, 5R*)-7-benzyl-3-(2-methoxy-5-(5-trifluoromethyl-1H-tetrazol-1-yl)phenyl)-1-oxa-7-azaspiro[4,5]decane;

(±)-(3R*, 5R*)-7-benzoyl-3-(2-methoxy-5-(5-trifluoromethyl-1H-tetrazol-1-yl)phenyl)-1-oxa-7-azaspiro[4,5]decane;

(±)-(3R*, 5R*)-7-(2-phenylethyl)-3-(2-methoxy-5-(5-trifluoromethyl-1H-tetrazol-1-yl)phenyl)-1-oxa-7-azaspiro[4,5]decane;

7-benzyl-3-(2-methoxy-5-(5-methyl-1H-1,2,4-triazol-1-yl)phenyl)-1-oxa-7-azaspiro[4,5]-dec-3-ene;

7-benzyl-3-(2-methoxy-5-(5-trifluoromethyl-1H-1,2,4-triazol-1-yl)phenyl)-1-oxa-7-azaspiro[4,5]-dec-3-ene;

7-benzyl-3-(2-methoxy-5-(N-methyltrifluoroacetamido)-1-oxa-7-azaspiro[4,5]-dec-3-ene;

7-benzyl-3-(2-isopropoxy-5-(2-trifluoromethyl-1H-imidazol-1-yl)phenyl)-1-oxa-7-azaspiro[4,5]dec-3-ene;

7-benzyl-3-(2-methoxy-5-(5-trifluoromethyl-1H-tetrazol-1-yl)methylphenyl)-1-oxa-7-azaspiro[4,5]dec-3-ene;

(±)-(3R*, 5R*)-7-benzyl-3-(2-methoxy-5-(2-trifluoromethyl-1H-imidazol-1-yl)phenyl)-1-oxa-7-azaspiro[4,5]decane;

(=)-(3R*, 5R*, 11R*/S*)-3-(2-methoxy-5-(2-trifluoromethyl-1H-imidazol-1-yl)phenyl)-7-(1-phenyl)ethyl-1-oxa-7-azaspiro[4,5]decane;

(±)-(3R*, 5R*)-3-(2-methoxy-5-(2-trifluoromethyl-1H-imidazol-1-yl)phenyl)-7-(2-phenyl)ethyl-1-oxa-7-azaspiro[4,5]decane;

(±)-(3R*, 5R*)-3-(2-methoxy-5-(2-trifluoromethyl-1H-imidazol-1-yl)phenyl)-7-phenylacetyl-1-oxa-7-azaspiro[4,5]decane;

(±)-(3R*, 5R*)-7-(2-oxo-2-phenyl)ethyl-3-(2-methoxy-5-(2-trifluoromethyl-1H-imidazol-1-yl)phenyl)-1-oxa-7-azaspiro[4,5]decane;

(±)-(3R*, 5R*, 12S*/R*)-7-(2-hydroxy-2-phenyl)ethyl-3-(2-methoxy-5-(2-trifluoromethyl-1H-imidazol-1-yl)phenyl)-1-oxa-7-azaspiro[4,5]decane;

or a pharmaceutically acceptable salt thereof.

14. A compound as claimed in claim 1 wherein $R^1$ is at the 2'-position, $R^3$ is at the 5'-position and $R^9$ and $R^{10}$ are at the 8- and 9-positions.

15. A pharmaceutical composition comprising a compound as claimed in claim 1 in association with a pharmaceutically acceptable carrier or excipient.

16. A method for the treatment or prevention of physiological disorders associated with an excess of tachykinins, which method comprises administration to a patient in need thereof of a tachykinin reducing amount of a compound according to claim 1.

17. A method according to claim 16 for the treatment or prevention of pain or inflammation.

18. A method according to claim 16 for the treatment or prevention of migraine.

19. A method according to claim 16 for the treatment or prevention of emesis.

20. A method according to claim 16 for the treatment or prevention of postherpetic neuralgia.

21. A process for the preparation of a compound as claimed in claim 1 which comprises:

(A.1), where X is —CH$_2$— and Y is —CH$_2$ or —CH$_2$CH$_2$—, reducing a compound of formula (IIA)

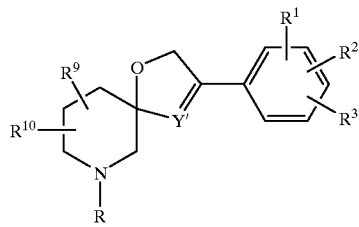

(IIA)

wherein Y' is —CH= or —CH$_2$CH=; or (A.b 2), where X is —CH$_2$— and Y is —CH$_2$CH$_2$—, reducing a compound of formula (IIB)

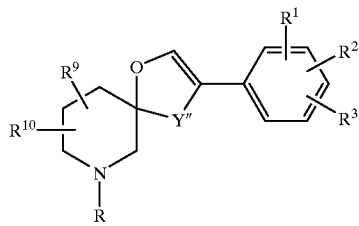

(IIB)

wherein Y" is —CH$_2$— or —CH$_2$CH$_2$—; or (B), where X is —CH$_2$— and Y is —CH= or —CH$_2$CH= and the broken line is a double bond, reacting of a compound of formula (III)

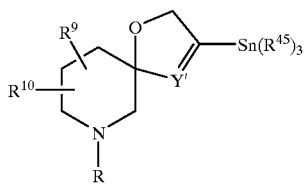

(III)

wherein Y' is —CH= or —CH$_2$CH= and each $R^{45}$ is a $C_{1-4}$alkyl group, with a compound of formula (IV)

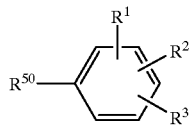

(IV)

wherein $R^{50}$ is a leaving group; or (C) reacting a compound of formula (V)

(V)
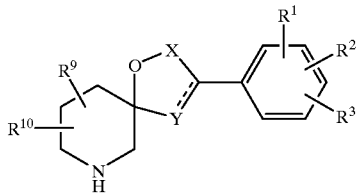

with a compound of formula (VI):

LG—R² (VI)

where $R^Z$ is a group of the formula R as defined in claim 1 or a precursor therefor and LG is a leaving group; and, if $R^Z$ is a precursor group, converting it to a group R; or (D) interconversion of a compound of formula (I) to give another compound of formula (I); or (E), where $R^3$ is a tetrazol-1-yl group, reacting an intermediate of formula (VII)

(VII)
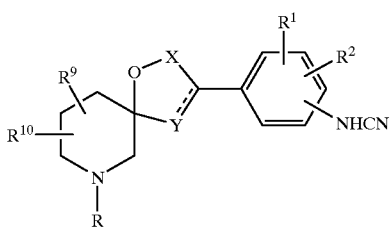

with ammonium chloride and sodium azide at elevated temperature; or (F) a coupling reaction between a compound of formula (VIII) and (IX)

(VIII)
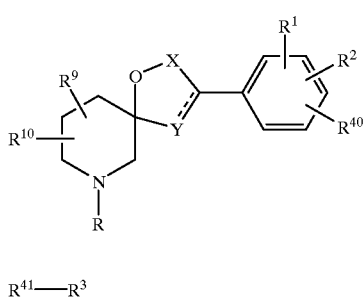

$R^{41}$—$R^3$ (IX)

wherein one of $R^{40}$ and $R^{41}$ is $B(OH)_2$ or $Sn(alkyl)_3$ or a derivative thereof, and the other is a leaving group; or (G) cyclising a compound of formula (X)

(X)
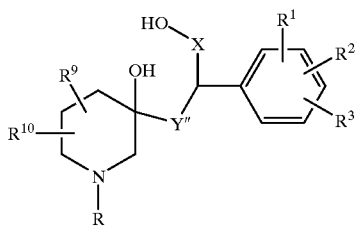

wherein Y" is —$CH_2$— or —$CH_2CH_2$—, by an acid catalysed intramolecular cyclisation reaction or by a dehydration reaction; or (H) reacting compound of formula (XX)

(XX)
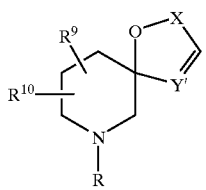

with a compound of formula (IV), under the conditions of a reductive Heck reaction; or (J), where $R^1$ is $C_{1-6}$alkoxy, fluoro$C_{1-6}$alkoxy, $C_{2-6}$alkenoxy, $C_{3-7}$cycloalkoxy, $C_{3-7}$cycloalkyl$C_{1-4}$alkoxy or benzyloxy, reacting a compound of formula (XXVI)

(XXVI)
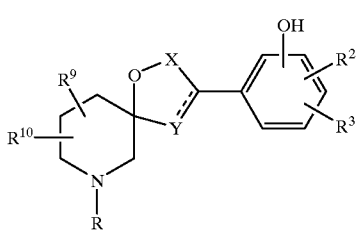

with an appropriate alkyl-, fluoroalkyl-, alkenyl-, cycloalkyl-, cycloalkylalkyl- or aralkyl-halide, in the presence of a base; or (K), where Y is —CH= or —$CH_2CH$=, dehydrating of a compound of formula (XXVII)

(XXVII)
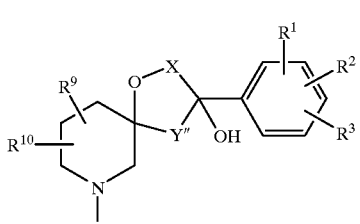

using an acid such as trifuloroacetic acid; or (L) reacting a compound of formula (XXVIII)

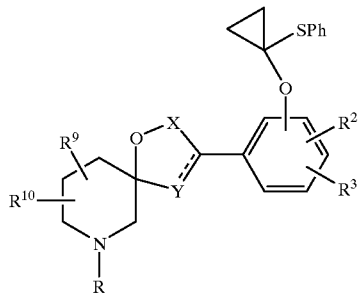

with lithium naphthalenide;

each process being followed, where necessary, by the removal of any protecting group where present;

and when the compound of formula (I) is obtained as a mixture of enantiomers or diastereoisomers, optionally resolving the mixture to obtain the desired enantiomer;

and/or, if desired, converting the resulting compound of formula (I) or a salt thereof, into a pharmaceutically acceptable salt thereof.

* * * * *